US005797515A

United States Patent [19]
Liff et al.

[11] Patent Number: 5,797,515
[45] Date of Patent: Aug. 25, 1998

[54] METHOD FOR CONTROLLING A DRUG DISPENSING SYSTEM

[75] Inventors: Harold J. Liff, Lexington; Brian T. Hart, Bedford; Robert L. Wallace, Pepperell, all of Mass.; Arthur A. Berube, Hampstead, N.H.

[73] Assignee: ADDS, Inc., N. Billerica, Mass.

[21] Appl. No.: 642,484

[22] Filed: May 3, 1996

Related U.S. Application Data

[63] Continuation-in-part of Ser. No. 544,623, Oct. 18, 1995, Pat. No. 5,713,485.

[51] Int. Cl.$^6$ ............................................. G07F 11/00
[52] U.S. Cl. ............................ 221/2; 221/129; 364/479.11
[58] Field of Search ................................... 221/3, 2, 7, 15, 221/123, 124, 122, 131; 364/479.01, 479.11, 479.07

[56] References Cited

U.S. PATENT DOCUMENTS

| | | | |
|---|---|---|---|
| 3,917,045 | 11/1975 | Williams et al. | 194/4 |
| 4,546,901 | 10/1985 | Buttarazzi | 221/10 |
| 4,655,026 | 4/1987 | Wigoda | 53/55 |
| 4,695,954 | 9/1987 | Rose et al. | 364/413 |

(List continued on next page.)

FOREIGN PATENT DOCUMENTS

95/25423  9/1995  WIPO .

OTHER PUBLICATIONS

R$_x$obot, "The Safe Solution for Medication Management", Automated Healthcare Inc., Pharmacy Robotics, 261 Kappa Drive, 1994, 15238–2873 (Publication).

Meditrol, "Automation Systems", Fact Sheet, 9800 Centre Parkway, Suite 600, Houston, Tx. 77036 (Publication).

Omnicell, "Omnicell See & Touch" Supply System, Omnicell Technologies, Inc., 1101 East Meadow Drive, Palo Alto, CA 94303 (1994) (Brochure).

R$_x$obot™, "The Safe Solution for Medication Management", Automated Healthcare, Inc., Pharmacy Robotics, 261 Kappa Drive, Pittsburgh, PA 15238–2873 (Brochure).

Omnicell, ™"Omnicell See & Touch™ Supply System", Omnicell Technologies, Inc., 1101 East Meadow Drive, Palo Alto, CA 94303 (1994) (Brochure).

Meditrol™ Automation Systems, "Fact Sheet", Meditrol Automation Systems, 9800 Centre Parkway, Suite 600, Houston, TX 77036 (Brochure).

Vangard Labs, Inc., "Reverse Number 4×25 for Controlled Substances", VanGard Labs, Inc., 890 L. Rogers Wells Blvd., Glasgow, KY 42141 (Apr. 1993) (Brochure).

Baxter, "Elevate Your Capacity to Perform—Begin With Productivity Systems," Baxter Healthcare Corporation, I.V. Systems Division, Productivity Systems, Route 120 & Wilson Road, Round Lake, IL 60073 (Dec. 1993) (Brochure).

Primary Examiner—Kenneth Noland
Attorney, Agent, or Firm—Hamilton, Brook, Smith & Reynolds, P.C.

[57] ABSTRACT

An automated drug dispensing system includes a cabinet adapted to store a variety of prepackaged pharmaceuticals in a plurality of bins for filling patient prescriptions. Each bin stores a particular variety of packaged multiple-dose pharmaceutical. Each variety of pharmaceutical is associated with a particular code. A controller receives request signals and in response generates dispense signals. Each bin includes a dispenser coupled to the controller for dispensing the packaged pharmaceuticals therefrom in response to a dispense signal sent from the controller. After a package is dispensed, a code reader determines the code of the dispensed package and verifies whether the code on the dispensed package matches the code of the requested package.

27 Claims, 55 Drawing Sheets

U.S. PATENT DOCUMENTS

| | | | |
|---|---|---|---|
| 4,717,042 | 1/1988 | McLaughlin | 221/3 |
| 4,732,411 | 3/1988 | Siegel | 283/75 |
| 4,766,542 | 8/1988 | Pilarczyk | 364/413 |
| 4,785,969 | 11/1988 | McLaughlin | 221/2 |
| 4,818,850 | 4/1989 | Gombrich et al. | 235/494 |
| 4,837,719 | 6/1989 | McIntosh et al. | 364/569 |
| 4,847,764 | 7/1989 | Halvorson | 364/413.02 |
| 4,911,327 | 3/1990 | Shepherd et al. | 221/3 |
| 4,918,604 | 4/1990 | Baum | 364/413.01 |
| 4,967,928 | 11/1990 | Carter | 221/2 |
| 4,980,292 | 12/1990 | Elbert et al. | 435/289 |
| 4,991,740 | 2/1991 | Levasseur | 221/129 |
| 5,014,875 | 5/1991 | McLaughlin et al. | 221/2 |
| 5,047,948 | 9/1991 | Turner | 364/479 |
| 5,292,029 | 3/1994 | Pearson | 221/2 |
| 5,314,243 | 5/1994 | McDonald et al. | 312/215 |
| 5,337,919 | 8/1994 | Spaulding et al. | 221/2 |
| 5,348,061 | 9/1994 | Riley et al. | 141/104 |
| 5,390,796 | 2/1995 | Kerfoot, Jr. | 206/534 |
| 5,404,384 | 4/1995 | Colburn et al. | 377/6 |
| 5,431,299 | 7/1995 | Brewer et al. | 221/2 |

+ RCD DISPENSING - [SCR # 1100 - NEW PRESCRIPTION FOR: RUST, MARY ANNE]

FIG. 14B

+ RCD DISPENSING  [SCR #1100 - NEW PRESCRIPTION FOR: RUST, MARY ANNE]

| Profile | Patient | Payor & Subscriber | Verify | Drug | Signa |

323B

— Payor Information —
Prescription Card Service

● ○
○ Charge
○ Cash

Group # 56565656
Card # 17171717
Last Name: RUSH
Rel Code: 1
Per Code: 21
———— Testing Data ————
Pharm # 770414
Proc Ctl 9999999999

— Prescription Information —
Select Prescriber   504A

ID #
DEA #        501
State Lic #
Phone
Fax

— Pharmacist Information —
Select Pharmacist   504B

+ RCD DISPENSING [SCR# 1100-NEW PRESCRIPTION FOR: RUST, MARY ANNE]

323F

519

Patient | Payor & Subscriber | Drug | Signa

Profile | Verify

— Patient Information
Rust, Mary Anne
156 Main St Suite B
Portland, OR 012345
Home (888) 888-8888
Work (888) 888-8888

SSNo: 812439876
ID: RUSTMA001
DOB: 9/15/65

— Payor
Prescription Card Service

— Prescriber
Dr. Jones, Ralph

— ICD-9
Diagnostics on Brain

— Drug
Brand: Procardia tab 10mg
Generic: Nifedipinet tab 10mg
In Bottle, 120  NDC00069-2600-1
In Stock, 33
Trouble Shooting
Column 1    Cabinet 1

— Signa
Take 1 Tablet 3 Times Daily w/Meals

— Adjucation Information
Dispense as written Code 1
Location Code 07
Origin Code 2
Compound Code 2

DUR RESPONSE INTERVENTION

DUR 1 | DUR 2 | DUR 3

DUR Response Data 1

Conflict: HD/High Dose Alert    Sig
Pharm Ind: 0
Prescr Ind: 0                    DBI
Prev Qty 00000  Prev Date 00000000
Minimum Dose 5.00 Units/Day Intervention
Outcome
Comments

525

RX Number: 9157

DONE

SKIP

```
PHARMACY                          Keep all doctor's
Roc 9157 Fill: 05-02              visits and lab
TAKE 1 TABLET AT BEDTIME          appointments Protropin Tab 10mg                                    John Doe
Somatrem Tab 10mg/

Count: 4  Lot#: 123456            Roc 9157            Roc 9157
Expiry: 12/99  Claim Auth:        John Doe            John Doe
               Price:             Take 1 Tablet       Take 1 Tablet
                                  at Bedtime          at Bedtime
88 Refills left
To Refill call 800-4 Refill       Protropin Tab 10mg  Protropin Tab 10mg
PC 2000 DEMO 0/34/JQS             Refills: 88         Refills: 88
Dr. Jones, Ralph
```

Patient Education Monograph          Rx 9157    Date: 05-02-1996
Somatrem Injection                   JOHN DOE Uses:                                TAKE 1 TABLET AT BEDTIME How to Use This Medication:          Dr Jones, Ralph
                                     Protropin Tab 10 mg Count: 4  Lot# 123456
                                     Claim Auth:
Side Effects:                        Expiry: 12/99        Price:

Precautions:

Drug Interactions:

Notes:

Missed Dose:

Storage

FIG. 15

METHOD FOR CONTROLLING A DRUG DISPENSING SYSTEM

RELATED APPLICATIONS

This application is a Continuation-in-Part of U.S. Ser. No. 08/544,623, filed Oct. 18, 1995 Now U.S. Pat. No. 5,713,485, the entire contents of which is incorporated herein by reference.

BACKGROUND OF THE INVENTION

Automated pharmaceutical delivery systems have been in use for over thirty years. The initial purpose of such systems was to reduce the high rates of medication errors associated with manual distribution. In modern times, automated systems present more sophisticated advantages. These include: further reduction of errors, lower costs associated with pharmaceutical distribution, reduction of personnel, inventory control, substance control, automated documentation, and relieving professional pharmacists of many tasks.

The current state of the art of automated pharmaceutical delivery systems, otherwise known as medication management devices generally fall under three categories: automated devices in the central pharmacy area; automated devices in the patient care unit; and point-of-care information systems.

The primary goal of centrally-located devices is to replace or improve the current manual process for filling unit dose carts. These devices offer the advantage of a single, centralized inventory and a lower overall inventory. Disadvantages of such devices include their large size, high cost, and reliance on efficient delivery systems.

Patient care unit-based devices replace the traditional manual unit dose cart filling and delivery system and provide increased control over floor stock. Advantages of such systems include their smaller size and lower cost relative to centrally-located devices, immediate access to medications, and automated documentation of medication administration. Disadvantages include application to unit dose levels only, increased costs due to the maintenance of multiple inventories in multiple units, additional time required to restock multiple devices, and larger inventory.

Point-of-care systems are designed to enable immediate exchange of patient data at the bedside. Such systems allow for rapid access to patient information, fast documentation, integration of hospital information systems, and immediate verification of drug administration. Primary disadvantages of point-of-care systems include high cost associated with placing hardware in each room, networking the system, and security issues associated with personal data access.

The above-described systems offer solutions for medication management in large hospitals where the large expense associated with large centrally-located pharmacy systems, decentralized patient care units, and point-of-care systems at the bedside are justifiable for unit-dose dispensing and verification. These systems fail to address efficient and economical medication management at medium size facilities, for example health maintenance organizations which cannot justify the expenses associated with the large and costly aforementioned systems. Furthermore, while the above systems provide a solution for unit-dose dispensing for individual patients, they fail to address the issue of filling weekly or monthly prescriptions in a cost-effective manner.

SUMMARY OF THE INVENTION

The present invention combines computer hardware and software, a telecommunications capability, and a medication container dispensing cabinet to form a complete in-office dispensing system. This enables drug prescription dispensing in volume by a physician, pharmacist, or other licensed practitioner directly to the patient at a clinic, group practice, or other location outside a pharmacy or hospital. The system provides a convenient, safe, automated, and low cost drug delivery system for the patient.

The present invention is directed to an apparatus and method for automated dispensing of packaged pharmaceuticals. The apparatus of the invention includes a cabinet housing for storing a variety of packaged pharmaceuticals in a plurality of bins. Each bin stores a particular variety of packaged pharmaceutical where each package typically contains a plurality of unit doses as normally provided in a pharmacy filled prescription. Each variety of pharmaceutical is associated with a particular code marked on the package. When the packaged items are loaded into the system, the loader scans each bar coded package with a bar code reader so that the data base for the unit properly reflects the packages contained in the unit. For dispensing a controller receives request signals and in response generates dispense signals. Each bin includes a dispenser coupled to the controller for dispensing a packaged pharmaceutical therefrom in response to a dispense signal sent from the controller. When the package is dispensed, a code reader determines the code of the dispensed package and verifies whether the code of the dispensed package matches the code of the requested package.

The dispensing process can be initiated by an authorized user at a computer terminal connected to the cabinet controller. Alternatively, a computer can be used to program a card or slip with patient information, with the cabinet being adapted for receiving the card, for automatic dispensing directly to the patient.

A plurality of the cabinet housings can be installed in a modular or daisy-chained configuration in which a single controller operates a plurality of housings. In a preferred embodiment of the apparatus of the invention, the bins are in the shape of vertically-disposed columns shaped to store a plurality of bottles stacked vertically. Each bottle is sealed and contains a selected number of doses prior to being dispensed. Pharmaceutical packages are laid on top of each other within each column and are fed by gravity from the top of the column and exit at the bottom of the column on a first-in-first-out basis. Each column includes a replaceable label containing a code which matches the code disposed on the packages placed in that column. Package coding is preferably accomplished by bar code which can include the drug identification number, dosage expiration date and number of tablets. The controller is preferably a computer. In an automated system, sensors mounted in the bins monitor the inventory of the packages in each bin and detect jammed bins.

The cabinet is preferably mounted on a wall or on a supporting cart as a stand alone unit. A ramp delivers a dispensed pharmaceutical to a drop point. The ramp is preferably sloped so that gravity delivers the dispensed pharmaceutical without the need for other conveying means. A label printer is coupled to the controller for printing a patient specific prescription label for attaching to a dispensed pharmaceutical package. The prescription label can include a printed picture of the pharmaceutical contained in the package. A document printer is likewise coupled thereto for printing instructions specific to the dispensed pharmaceutical for use by the patient or medical practitioner. In a preferred embodiment, the printers are inhibited until the bar-code reader verifies that proper dispensing of the pharmaceutical has occurred.

A preferred method of using the invention for a clinical trial includes dispensing a pharmaceutical and a placebo in different packages and monitoring use thereof. Clinical trials are commonly used in the evaluation of the safety and effectiveness of drug protocols in the pharmaceutical industry. These trials can typically take the form of distributing the drug being tested and a placebo to a selected patient population and then monitoring the outcome to determine the drug's effectiveness. The dispensing system of the present invention is particularly well suited to aid in the controlled distribution of both the drug (or drugs) under test and the placebo used in these clinical trials. Due to the accurate labelling, record keeping and remote distribution capabilities, and the ability to dedicate specific units to a particular trial the conduct of these trials can be done more safely and accurately.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 15 is a printout of a patient monograph to be administered to the patient along with labels for adherence to the dispensed pharmaceutical in accordance with the present invention.

DETAILED DESCRIPTION OF PREFERRED EMBODIMENTS

The present invention provides safe pharmaceutical prescription dispensing directly by physicians, pharmacists, and other licensed practitioners operating in small to medium size locations in a cost-effective manner. Prepackaged pharmaceuticals are stocked at nearby municipal service centers and distributed to the health care locations as needed. The inventory is continually and automatically monitored by a host computer at the location. Inventory is ordered on a just-in-time basis by the computer. In this manner, prepackaged multiple-dose pharmaceuticals are available to practitioners at the health-care facility for immediate filling of patient prescriptions.

The present invention offers significant advantages to physician group practices. The system improves customer service and enhances the image of the group practice. Drug theft is prevented by securing the pharmaceuticals in a closed system and inventory is kept low. The system meets state pharmacy, safety, and regulatory compliance laws, whereas many manual dispensing systems do not. A pharmaceutical distributor can handle all inventory planning, financing, maintenance, and ordering with minimal interaction with group practitioners. Disruptive telephone calls to the physician from pharmacists are minimized. Further, physicians can gain immediate access to a patient's pharmacy records currently unavailable to him.

Managed care providers, for example, Health Maintenance Organizations and Pharmacy Benefits Managers also realize significant advantages from the present invention. The invention increases the likelihood that a patient will receive the required treatment, because the pharmacy is available at the doctor's office. Labor costs for in-house pharmacies are reduced, allowing staff reductions or reassignments. In-house drug dispensing can be extended to physician-staffed satellite clinics and other locations not suitable economically for conventional pharmacies. The system enables automated patient compliance enhancing programs, drug utilization analysis, and the use of other emerging pharmacy management opportunities to reduce costs and improve patient compliance and wellness. Drug costs are reduced by formulary control, thereby encouraging generic substitution of name brand drugs. Inventory is tracked automatically by the drug distributor headquarters, thus preserving professional time for patient care.

The present invention also offers significant advantages to the patients. Drugs are provided immediately at the physician's office, avoiding an inconvenient trip to a pharmacy. This is particularly important to mobility-impaired patients and eliminates a major source of drug non-compliance. Electronic third-party payor cards can be used for drug purchases at the doctor's office. The patient can obtain prescription drugs at prices competitive with retail discounters. The physicians are able to track prescription compliance which can result in faster recovery.

Figure 1:
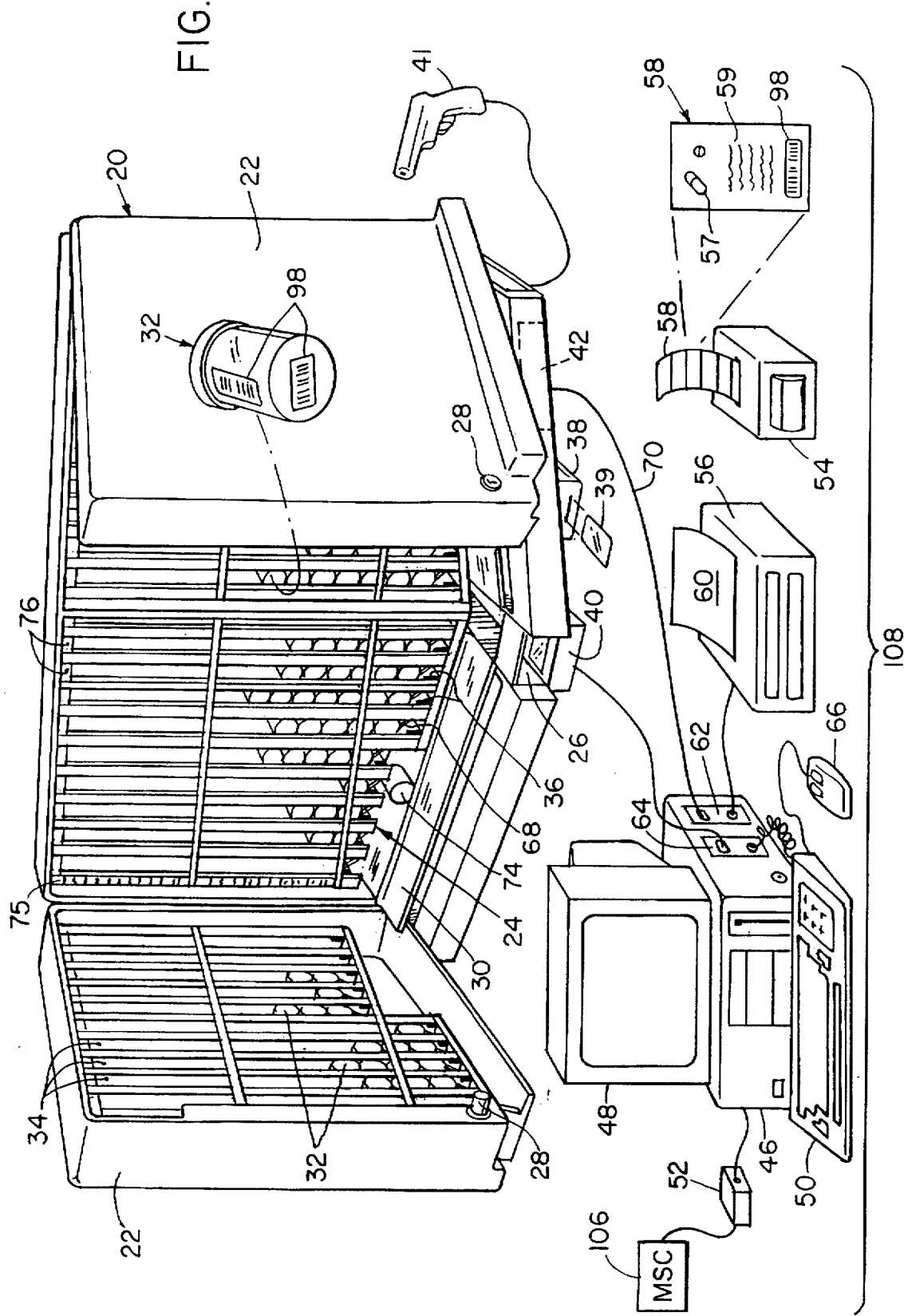
FIG. 1 is a diagram of preferred embodiment of an automated drug dispensing system in accordance with the present invention.

The apparatus of a preferred embodiment of the invention will now be described. FIG. 1 is a diagram of an automated drug dispensing system in accordance with the present invention. The primary components of the system include a remote control dispenser (RCD) cabinet 20, a host computer 46, a modem 52, a document printer 56, and a label printer 54. The cabinet 20 includes a rack 24 comprising a plurality of bins, preferably in the shape of columns 34. Packages 32 such as drug bottles, containing pharmaceuticals of various types are distributed among the columns 34, each column 34 containing a separate type of pharmaceutical. Four racks 24 are enclosed in the cabinet 20 chamber, two in the main cabinet 20 and two on the doors 22. The doors are secured by locks 28.

A licensed user, for example, a doctor, pharmacist, nurse, or other medical practitioner qualified to fill patient prescriptions, operates the system at the host computer 46, using a keyboard 50 and mouse 66 for input and receiving visual feedback at a monitor 48. Using the keyboard 50, a user enters a command to request dispensing of a particular packaged pharmaceutical variety 32 for a particular patient. The computer 46 transmits the request via an interface 70 to a controller 42 located on the RCD cabinet 20. The controller 42 interprets the command sent from the computer 46 and enables a dispensing actuator 68 in the appropriate column 34. The lowest package 32 in the appropriate column 34 is released from the column 34 and ejected onto a ramp 30. The released package 74 slides down the ramp 30 into an opening 26, where the released package 74 is made available to the dispensing party for transfer to the patient. A bar code reader 40, located near the dispensing opening 26, reads a code 98 on the dispensed package 74 and transmits the bar code information to the computer 46, which informs the user whether the code 98 on the dispensed package 74 matches that which was requested by the user. The bar code 98 can be disposed on the side, top, and/or bottom of the package 32. In an automated embodiment of the system, sensors 36 located on each column 34 monitor the dispensing process and notify the controller 42 of any package jams. The sensors 36 also monitor inventory of the columns 34 and notify the computer 46 through controller 42 that a particular column is empty or near empty.

Alternatively, the prescription can be dispensed directly to the patient. A card reader 38, mounted directly on or near the cabinet, is adapted to receive a card 39 from a patient. The card is programmed with patient information by a licensed practitioner. The patient inserts the card 39 in the card reader 38 and receives his medication automatically from the cabinet. The medication bottle 32 may be filled with a single dose of medication for a particular patient, or can include weekly or monthly doses. This embodiment is especially useful in large institutions, such as prisons, where many individuals require medication on a regular basis.

Upon validating the bar-code 98 of the dispensed package 74, the computer generates a label 58 containing prescription information at a label printer 54 to be placed on the package, and generates a document 60 at a document printer 56 containing additional instructions for the patient or practitioner. A modem 52 enables periodic or continuous communication between the host computer 46 and other computers in the network so that a complete inventory and status of each remote control dispenser cabinet is available at all times. Several remote control dispenser cabinets 20 can be integrated into a single installation operated by a single computer 46. The cabinets 20 can each be individually connected to the host computer 46, or may be daisy-chained, with only one cabinet 20 in the chain connected to the host 46.

Figure 3:
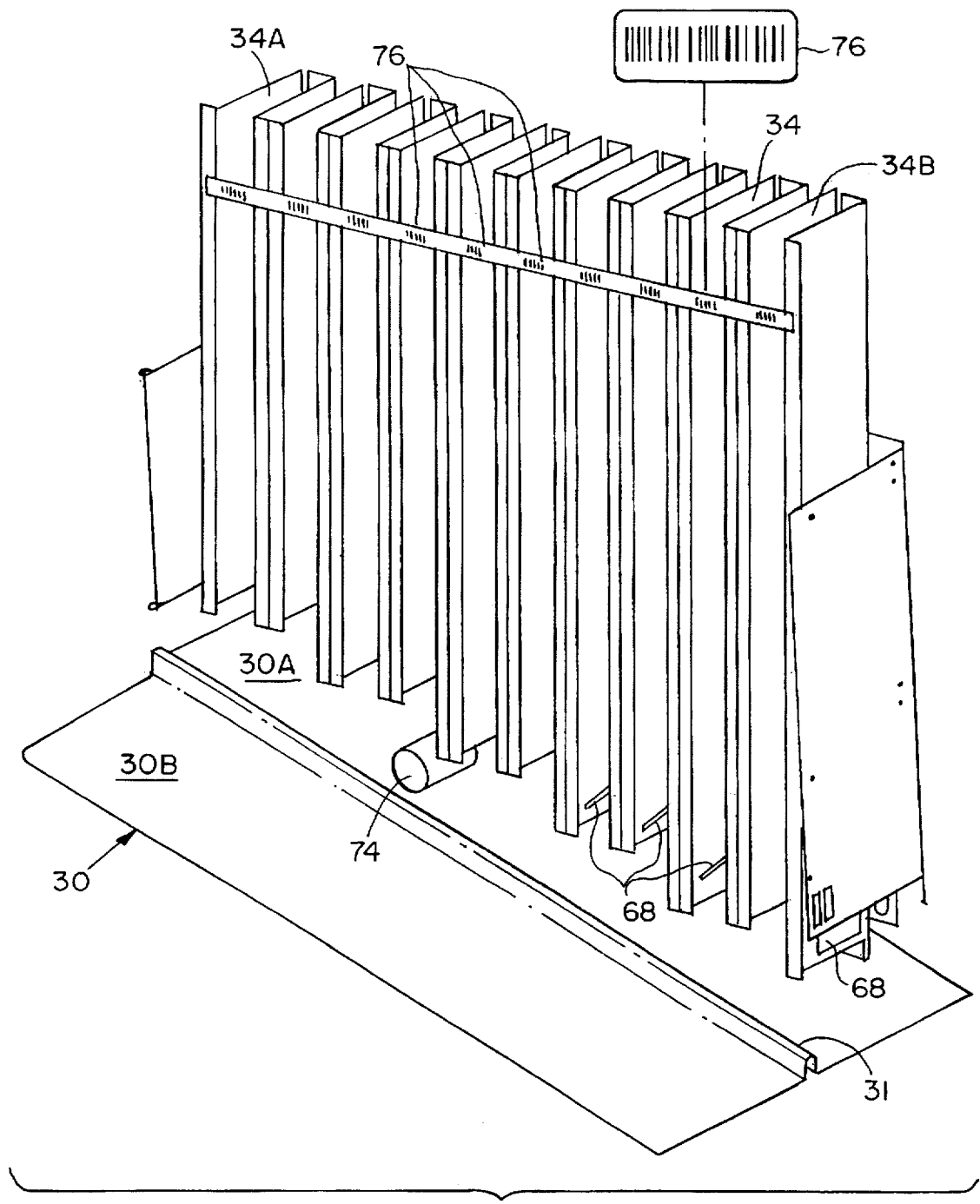
FIG. 3 is a block diagram of a preferred embodiment of a cabinet rack in accordance with the present invention.

A typical remote control dispenser cabinet 20 contains forty columns 34 for holding and dispensing the prepackaged pharmaceuticals. Each rack 24 includes ten columns 34, as shown in FIG. 3. Two racks are disposed on each side of the cabinet, one in the main cabinet area 20, and one on the door 22, such that when the door 22 is closed, the racks 24 face each other. A typical column will hold up to 13 packages of a given pharmaceutical. The columns at the ends of the cabinet 34A are shorter than the columns nearest the center of the cabinet 34B to accommodate the sloped ramp 30. The ramp 30 receives a dispensed pharmaceutical package, and directs it toward the dispensing area 26 in the center of the cabinet 20. A raised ramp divider 31 divides the ramp 30 into two sections 30A, 30B, each section for dispensing pharmaceutical packages from each rack. At the top of each column 34 is a replaceable bar code label 76 which identifies the pharmaceutical contained in that column and the appropriate column number. At the time of loading the cabinet, the column bar code label 76 is matched against the package label 98 to be loaded to verify that the correct pharmaceutical package 32 is placed in each column.

Referring back to FIG. 1, the RCD controller 42 receives commands from and transmits status information to the host computer 46 via the controller interface 70. A request command sent from the host computer 46 identifies the pharmaceutical package 32 to be dispensed. In response, the RCD controller 42 activates the appropriate dispenser 68, thereby releasing a single package of the variety requested. A parallel or serial I/O interface 62 at the host computer 46 provides a sufficient communication channel. The simplest interface is a unidirectional channel from the host computer 46 to the controller 42. A full duplex implementation allows the controller 42 to transfer status information back to the host 46. Status information may include errors such as package jams, empty columns, or other cabinet status. Availability of such information prevents inconsistencies in the database and provides the operator with recovery procedures. This would require adequate sensors 36 to be mounted in appropriate positions on the RCD cabinet 20.

The bar-code reader 40 can be mounted directly on the unit or can comprise a hand-held unit 41. It verifies proper loading of the RCD cabinet 20 and proper dispensing of each pharmaceutical package 32. Before a column 34 is loaded with packages 32, the column bar code label 76 is compared with the bar code label 98 of each package 32 inserted into the column 34. Each time a package 74 is dispensed from the cabinet 20, the package bar code label 98 is scanned by the bar code reader 40 to verify that the correct pharmaceutical has been dispensed. The bar code reader 40 is interfaced to the host computer 46 through a standard keyboard wedge 64. The wedge 64 makes the bar code reader 40 input via the bar code interface 72 appears to be coming from the keyboard 50. Such an interface is a simple and reliable interface to the pharmacy software operating on the computer 46. The bar code reader 40 must be highly reliable and provide a high first read rate. Label printing on the pharmaceutical packages 32 must be of high quality to accommodate this. During loading, the bottles are loaded into each column up to a certain height, the highest bottle in the column is positioned adjacent a bar coded column label 75 running along each column. Thus, the number of bottles in each column can be recorded at loading and tracked during use.

The host computer 46 runs the pharmacy software, provides a user interface, and supports the RCD controller 42, bar code reader 40, and modem 52. A standard off-the-shelf personal computer and operating system are sufficient to meet these requirements. As described above, the keyboard 50 and mouse 66 receive input from the user and the monitor 48 provides visual feedback. The document printer 56 prints documentation 60 such as detailed instructions and a label printer 54 prints package labels 58, for example, prescription information 59 for adherence to the dispensed package 74. The prescription label 58 may also include a printed picture of the pharmaceutical 57 contained on the bottle to provide additional security.

The modem 52 provides a communication link between the municipal service center (MSC) 106 and the remote control dispenser 108. Through this link, inventory of each RCD cabinet 20 is automatically monitored and updated in the MSC 106 computer. The modem link also serves as a medium to issue restock orders, update pharmacy software running on the host computer 46, and provide remote diagnostics. The modem can be compatible with standard telephone lines and can be capable of transferring data at sufficient rates.

The pharmacy software operating on the host computer 46 is a standard commercial software package which provides standard administrative and accounting capabilities. The pharmacy software also supports the unique features of the remote control dispenser system. These include: data communication with the RCD controller 42 via parallel or serial I/O interface 62; data communication with the bar code reader 40 via keyboard wedge 64; data communication with the municipal service center via modem 52; printing of labels 58 with the label printer 54 and printing of documentation 60 with the document printer 56. The software is described in further detail below in conjunction with FIGS. 7A and 7B.

The cabinet 20 and rack 24 are preferably fabricated from aluminum, stainless steel, or plastic to be fully compatible with a clinical setting. The rack 34 can be modified to provide for a diversity of packages including various box and bottle sizes, unit-of-use packaging, liquids, syringes, and various non-prescription products, for example, medical supplies.

The computer 46 can comprise a portable terminal, a notebook computer, or a hand-held personal digital assistant. Voice recognition or voice prompted software can be employed using a telephone or wireless local area network. Voice recognition systems can use a generic or a user-customized system and can include voice signatures. The objective is to maximize system flexibility and ease of use for the doctor and staff without compromising safety. The remote control dispenser system can be utilized as a free-standing system, as a local network integrated with physician office computers, or as a centralized network in conjunction with product release at a remote location.

Figure 4:
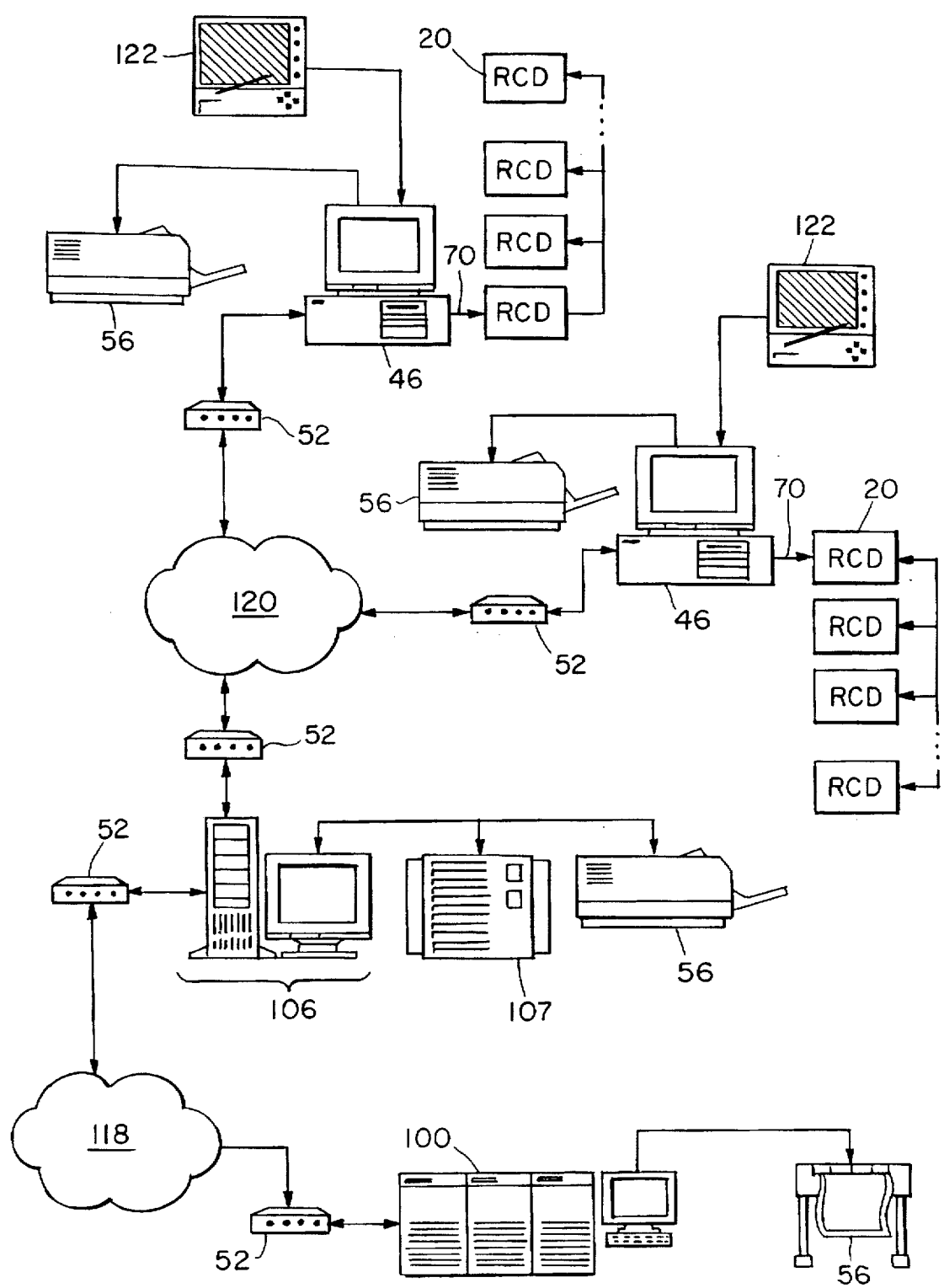
FIG. 4 is a block diagram of an automated drug dispensing system having daisy-chained remote control dispenser cabinets in accordance with the present invention.

FIG. 4 is a block diagram of a remote control dispensing configuration having daisy-chained remote drug dispensing units 20. A computer 100 at distribution headquarters is connected through a modem 52 to a bidirectional communication link 118. A computer 106, including disk storage 107 and a printer 56, at the municipal service center 106 communicates with headquarters 100 and with a plurality of remote control dispenser workstations 46 via modems 52. The RCD workstations 46 include a printer 56 and may include personal data assistants 122. The workstation 46 is connected via a controller interface 70 to remote control dispenser cabinets 20. The cabinets 20 can be daisy-chained as shown or may each be individually connected to the workstation 46. The computer 100 can also be linked by modem to all or selected remote dispensers so that each dispenser can be remotely controlled.

Figure 5:
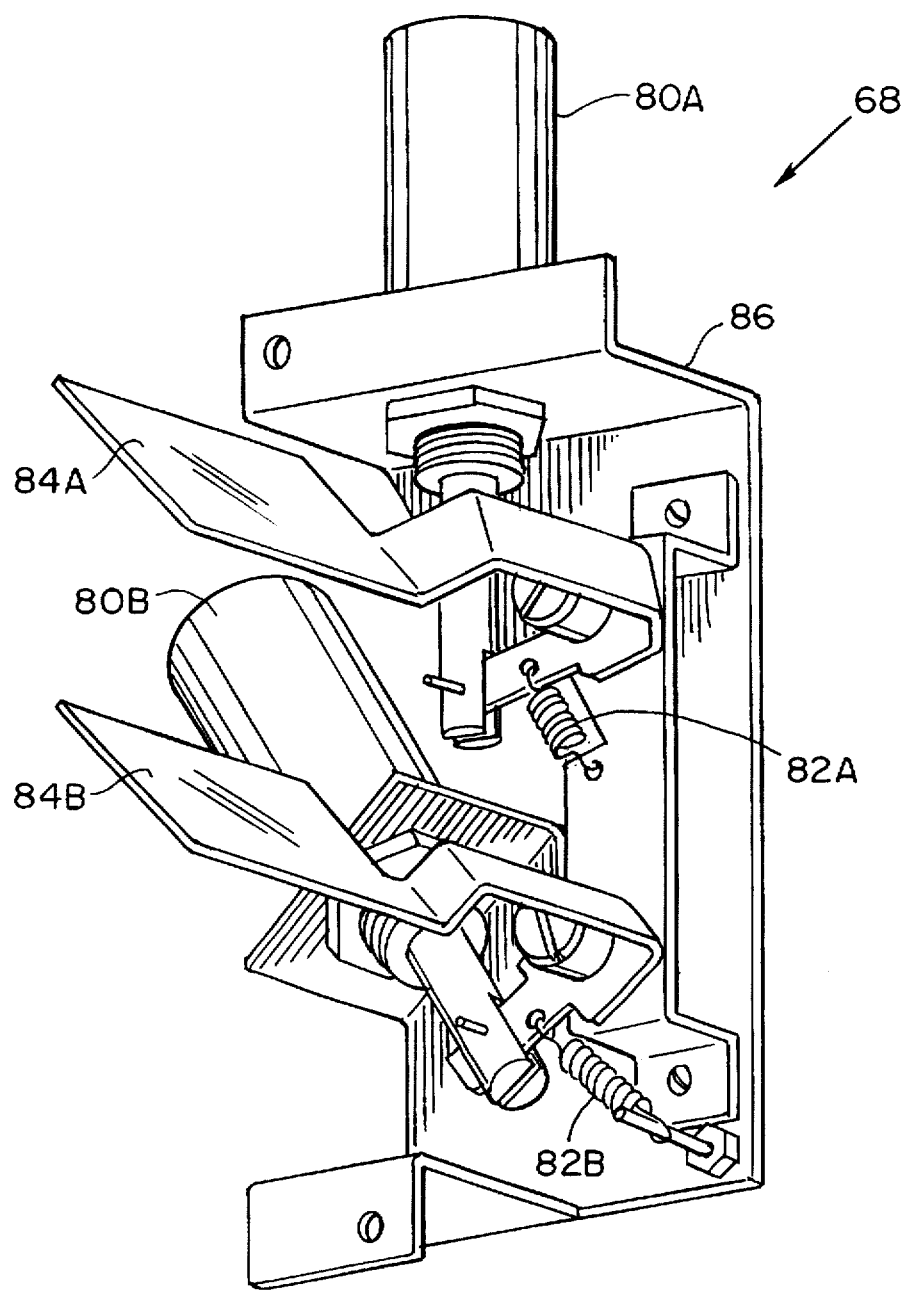
FIG. 5 is a perspective view of a dual-valve dispenser in accordance with the present invention.

FIG. 5 is a perspective view of a dual-valve dispenser 68. As shown in FIGS. 1 and 3, each column 34 includes a dispenser unit 68. The dispenser unit 68 is located at the bottom of each column for dispensing a single bottle 32 when commanded by the user. A preferred dispenser 68 includes an upper solenoid 80A and a lower solenoid 80B. Each solenoid 80A, 80B engages a corresponding dispenser valve 84A, 84B. The dispenser valves 84A, 84B are biased in a closed position by return springs 82A, 82B. All dispenser components are mounted to a housing 86.

Figures 6A, 6B, 6C:
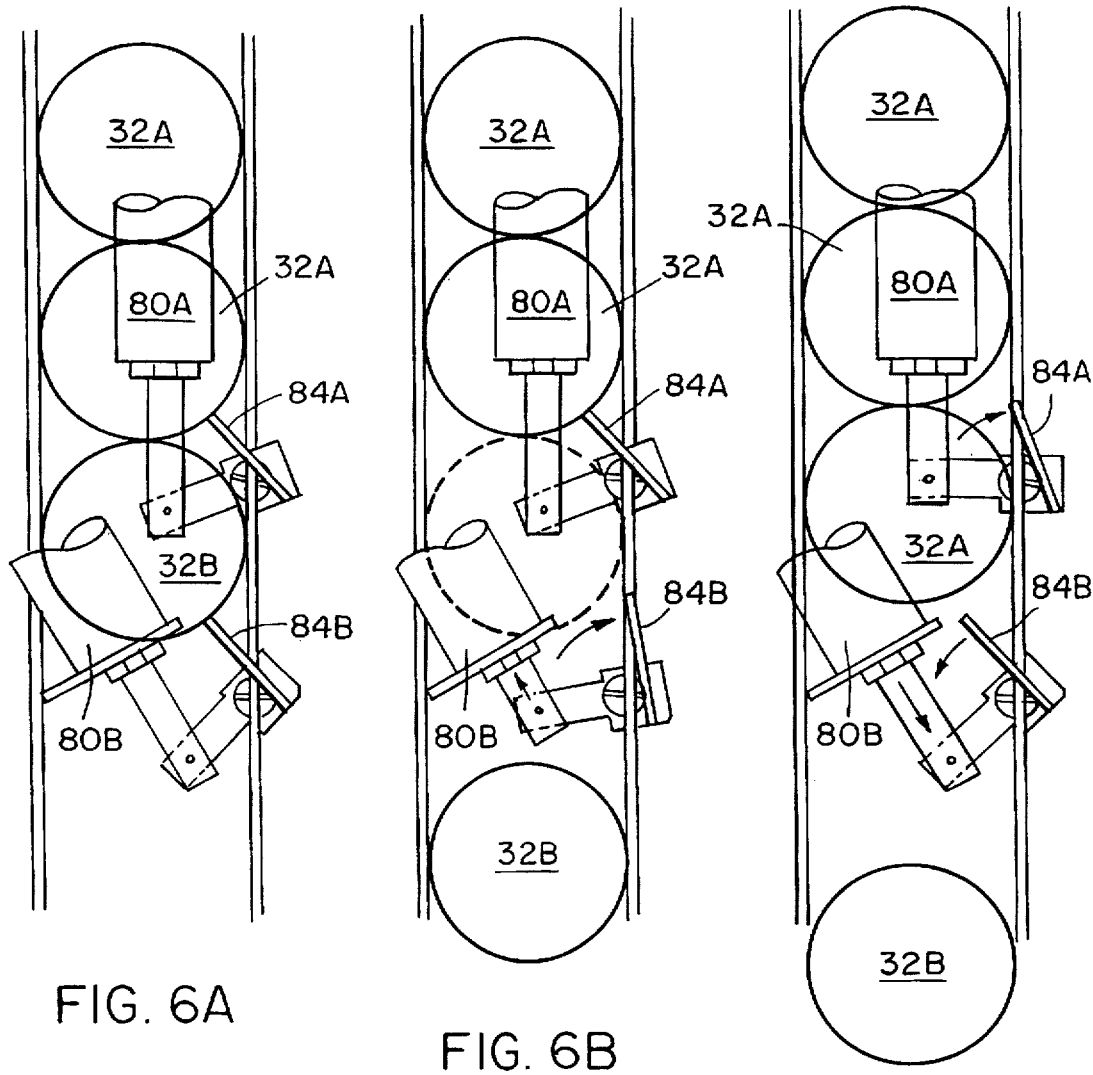
FIGS. 6A–6C are sequential illustrations of the operation of the dual-valve dispenser.

FIGS. 6A–6C illustrate operation of the dispenser valve during a dispensing sequence. In FIG. 6A, a gravity-fed column of bottles 32 is held in place by a bottle rack 24. A lower bottle 32B is retained by lower solenoid 80B and lower valve 84B and held in place between the valve 84B and the wall of the rack 24. The remaining bottles in the column 32A are retained by the upper solenoid 80A and upper valve 84A.

In FIG. 6B, the lower solenoid 80B retracts, preventing the lower valve 84B from interfering with the lower bottle 32B. This allows the lower bottle 32B to be released and dispensed. The upper bottles 32A continue to be held in position by upper valve 84A.

In FIG. 6C, the lower solenoid 80B is reactivated and lower valve 84B again interferes with the rack 24. The upper solenoid 80A is then retracted, disengaging the valve 84A from the upper bottles 32A. This allows the column 32A to fall and the lowest bottle engages the lower valve 84B. The upper solenoid 80A next closes the upper valve 84A, causing it to engage the next bottle 32A in the column. In this manner, a single bottle 32B is dispensed, the remaining bottles 32A all descend one position, and the dispenser 68 is again ready to dispense as shown in FIG. 6A.

Figure 7A:
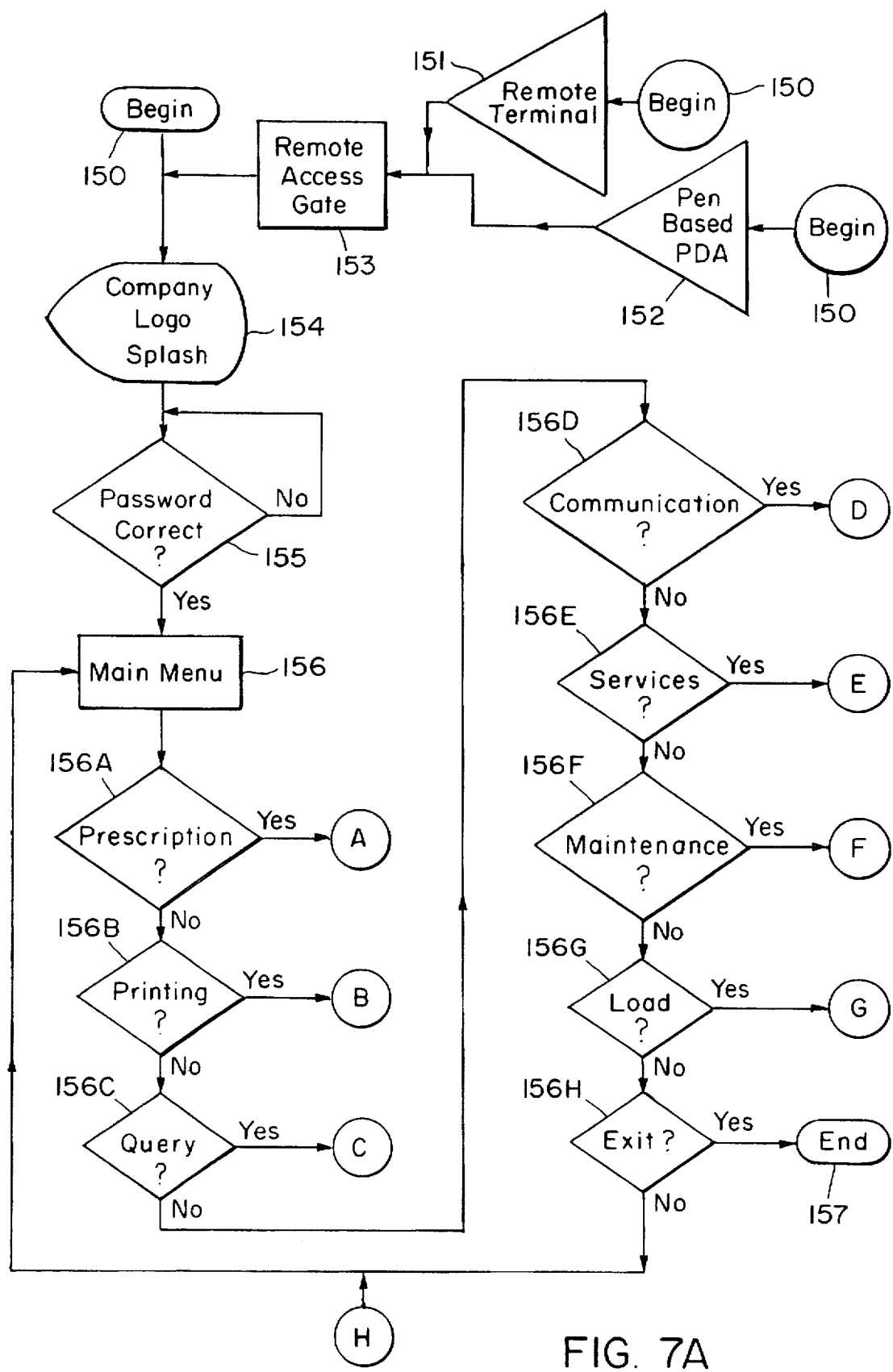
FIG. 7A is a flow diagram of the main menu software.
Figure 7B:
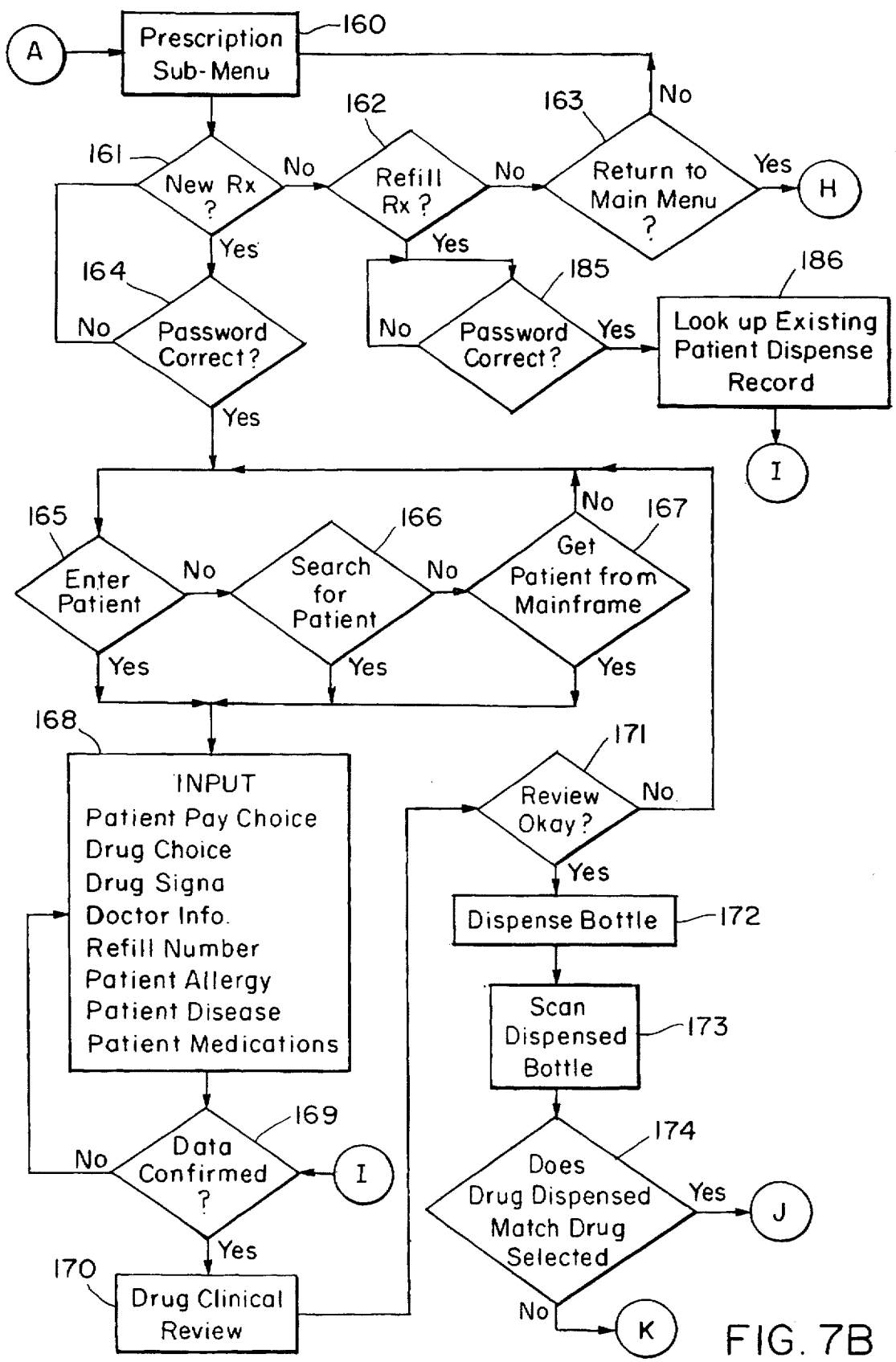
FIG. 7B is a flow diagram of the prescription menu software.

FIGS. 7A and 7B are flow diagrams of the computer 46 software. The software is preferably in a user-friendly windows format. In a standard format, the software is accessed on the host computer. Alternatively, the software is accessible by a remote terminal 151 or a pen-based personal data assistant 152 through a remote access gate 153. A splash screen 154 containing the company name, for example is output on the screen and the user is queued for a password 155. If the password is entered correctly, a main menu 156 is generated requesting the user to: access a prescription 156A; print a report or label 156B; investigate the database 156C; communicate with a remote location 156D; service the database 156E; maintain the cabinet 156F; load additional software 156G; and exit 156H. If exit 156H is selected, the program ends 157.

FIG. 7B is a flow diagram of the prescription submenu 160. The computer queues the user as to whether he would like to enter a new prescription 161, refill an existing prescription 162, or return to the main menu 163. If the user selects the new prescription 161 option, he is queued for a password 164. The user is next asked to enter the patient name 165. If the name is not known, then a search program 166 can search for the patient name or download the patient name from a mainframe 167. When the patient name is known, the user enters various prescription information and confirms that the data entered is correct 169. Next, the software runs a clinical review 170 and determines whether the prescription is proper 171.

If the prescription is proper, a bottle is dispensed 172 and the bar code of the dispensed bottle is scanned 173. If the bar code does not match that which was expected 174, then a warning is displayed 175, a communication link is set up with headquarters 176 and headquarters is warned 177 of the incorrect dispensing. If the proper medication was dispensed 174, then the computer prints a bottle label 178, generates a clinical review report 179 and conducts OBRA patient education monographs 180. The bottle is then administered to the patient 181 and the computer checks inventory 182 and if inventory is low, the computer communicates with headquarters 183 and orders new inventory 184. The computer then returns to the main menu 156.

If the user selected the "refill prescription" option 162 at the prescription submenu 160, then the password is checked 185 and the current patient record is displayed 186. The practitioner confirms the data 169 and dispensing takes place in the manner described above.

Figure 2:
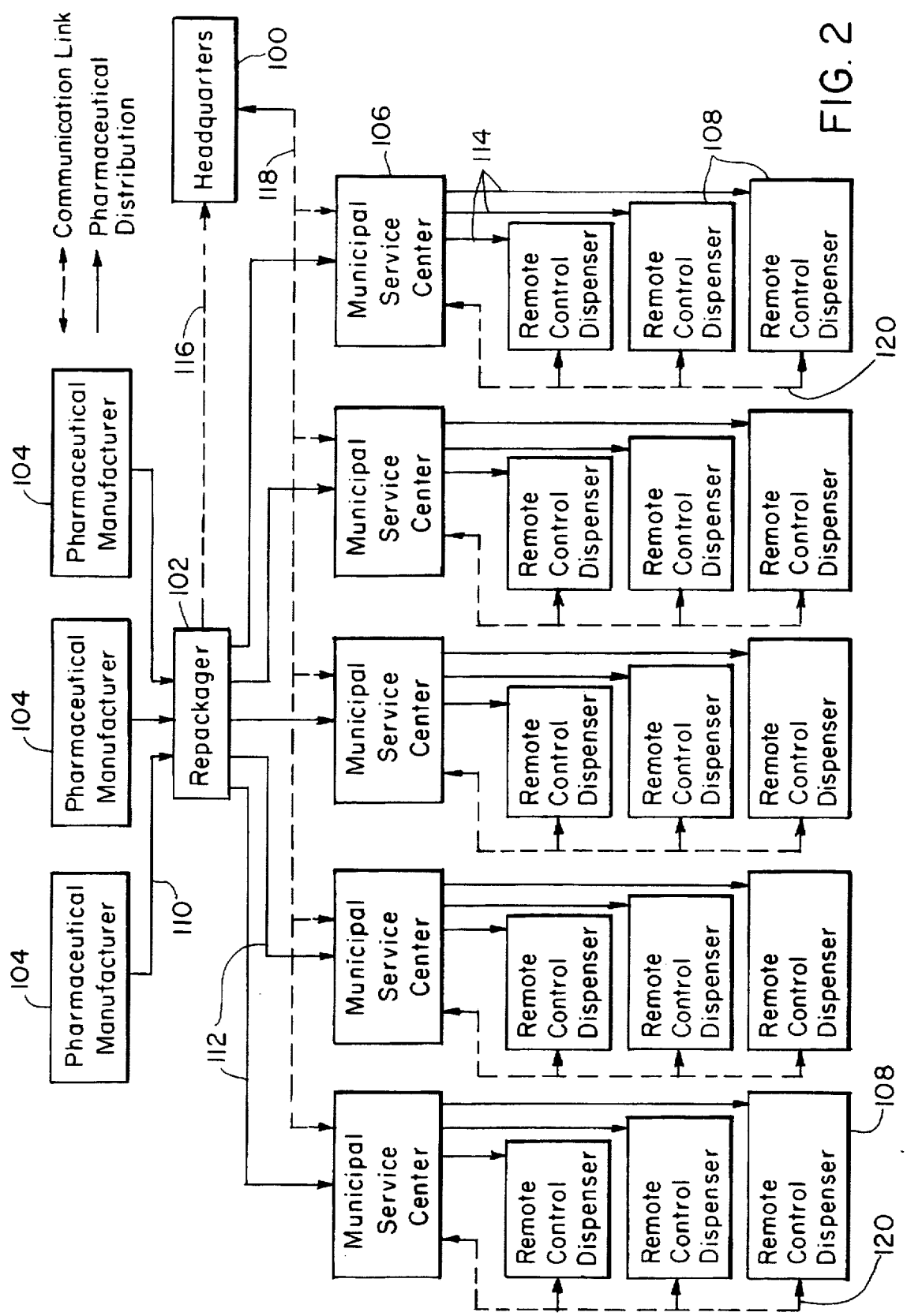
FIG. 2 is a block diagram of an automated system for pharmaceutical distribution and inventory management in accordance with the present invention.

FIG. 2 is a block diagram of an automated drug distribution system for maintaining the inventory of the RCD sites 108 in accordance with the present invention. The various RCD sites 108 are stocked with prepackaged pharmaceuticals obtained on a just-in-time (JIT) inventory basis from an FDA-approved drug repackager 102. The repackager 102 obtains unit-dose pharmaceuticals from various manufacturers 104, and repackages the unit-doses into a package containing multiple, prescription-sized doses. The packages must be suitable for use in the remote control dispenser units 108. The drugs are then distributed 112 to municipal service centers 106 which operate as regional distribution facilities in major urban areas. In turn, each municipal service center 106 redistributes 114 the packaged pharmaceuticals to each remote control dispenser 108 in its region.

The entire system is linked by a communication network 116, 118, 120. The inventory status of each remote control dispenser 120 is communicated to the corresponding municipal service center through a standard telephone link 120. Restocking requests and other inventory information are communicated 118 from the municipal service center 106 to headquarters 100 or any desired combination thereof. Headquarters 100 communicates 116 inventory requirements to the repackager 102. In response, the repackager 102 fills the order and ships the stock to the appropriate municipal service center 106. In this manner, headquarters 100 maintains an automated and continually-updated inventory of all remote control dispensers 108 on a JIT basis.

The system is further capable of monitoring patient records and billings and can format electronic third party billings for processing by the health care provider. With expanded software, patient records can be accessed on an integrated basis allowing for monitoring of drug side-effects and compliance.

In a preferred distribution system, a computer at the distributor headquarters 100 sends a restocking request via communication link 116 to the FDA-approved repackager 102. The repackager 102 fills the order and sends it by overnight air courier to the designated municipal service center 106. At the municipal service center, the drugs are distributed to drivers for specific remote control dispensers 108 in the local community. A driver delivers the drugs and restocks the remote control dispenser 108. As drugs are dispensed from the remote control dispenser 108, the inventory, sales, and restocking requirements are updated and transmitted via telephone link 120 to the computer at the municipal service center 106. The municipal service center computer is linked 118 to a similar computer at the distributor headquarters 100, completing the communication loop.

Pharmaceuticals are preferably bar-coded at the repackager 102. The pharmaceuticals are tracked using bar code information through each step of the process to the point of sale at the customer. In this way, all transactions are recorded and communicated in real-time to headquarters 100. This integrates accounting, accounts receivable, and inventory management systems, which allows the distributor headquarters to operate with minimal staffing. Each step of the process is self-contained and modular allowing rapid and flexible geographic expansion.

Each remote control dispenser is preferably placed on an inventory replenishment schedule. The number of weekly supply visits is a function of the rate of inventory usage. A computer record is maintained of prescriptions dispensed and product remaining. If there is a sudden increase in inventory activity, for example if a particular variety of medication is running low, an emergency call is initiated by the remote control dispenser 108 to the municipal service center 106 indicating the need for rapid inventory replenishment. The inventory preferably consists of the most frequently prescribed products used by physicians utilizing the unit. The variety can be adjusted at any time and will vary from location to location.

Figure 8:
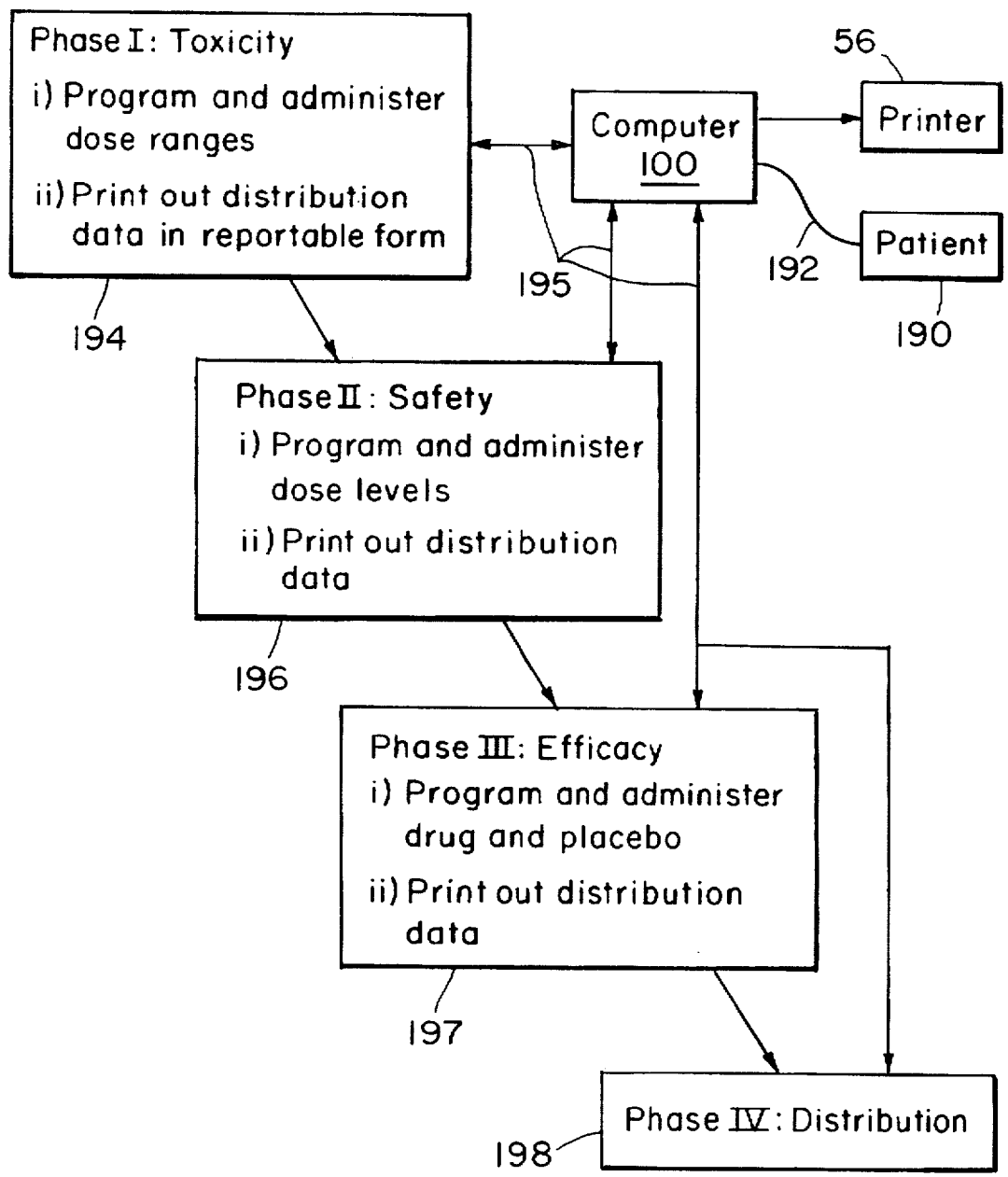
FIG. 8 is a schematic diagram illustrating the administration of a clinical trial in accordance with the invention.

A software module can be added to optimize use of the drug dispensing system for the administration of a clinical trial. As shown schematically in FIG. 8, clinical trials under current FDA regulations can be conducted in three phases; Phase I at 194 is to access toxicity; Phase II at 196 is to assess safety; Phase III at 197 is to assess efficacy, and possible Phase IV studies 198 for limited distribution. It is highly desirable to automate these procedures as the prompt and accurate evaluation of new treatments for safety and efficacy can lead to expedited regulatory review and approval.

The software is formatted to provide for administration of these three phases including the administration of the drug and a placebo in a so-called "double blind" procedure and to print out reports suitable for submission to the regulatory authority which include detailed data on distribution and dose. The computer records which packages contain placebos and which patients receive them. The computer 100 can record and execute various functions 195 in connection with these studies including printing of reports at printer 56, or communications along telephone line 192 for void activated or voice prompted follow up with the patient 190. These can include contacting the physician to report side effects or other information. A monogram on drug compliance is provided to each patient including drug interaction, side effects or dietary instructions.

Figure 9:
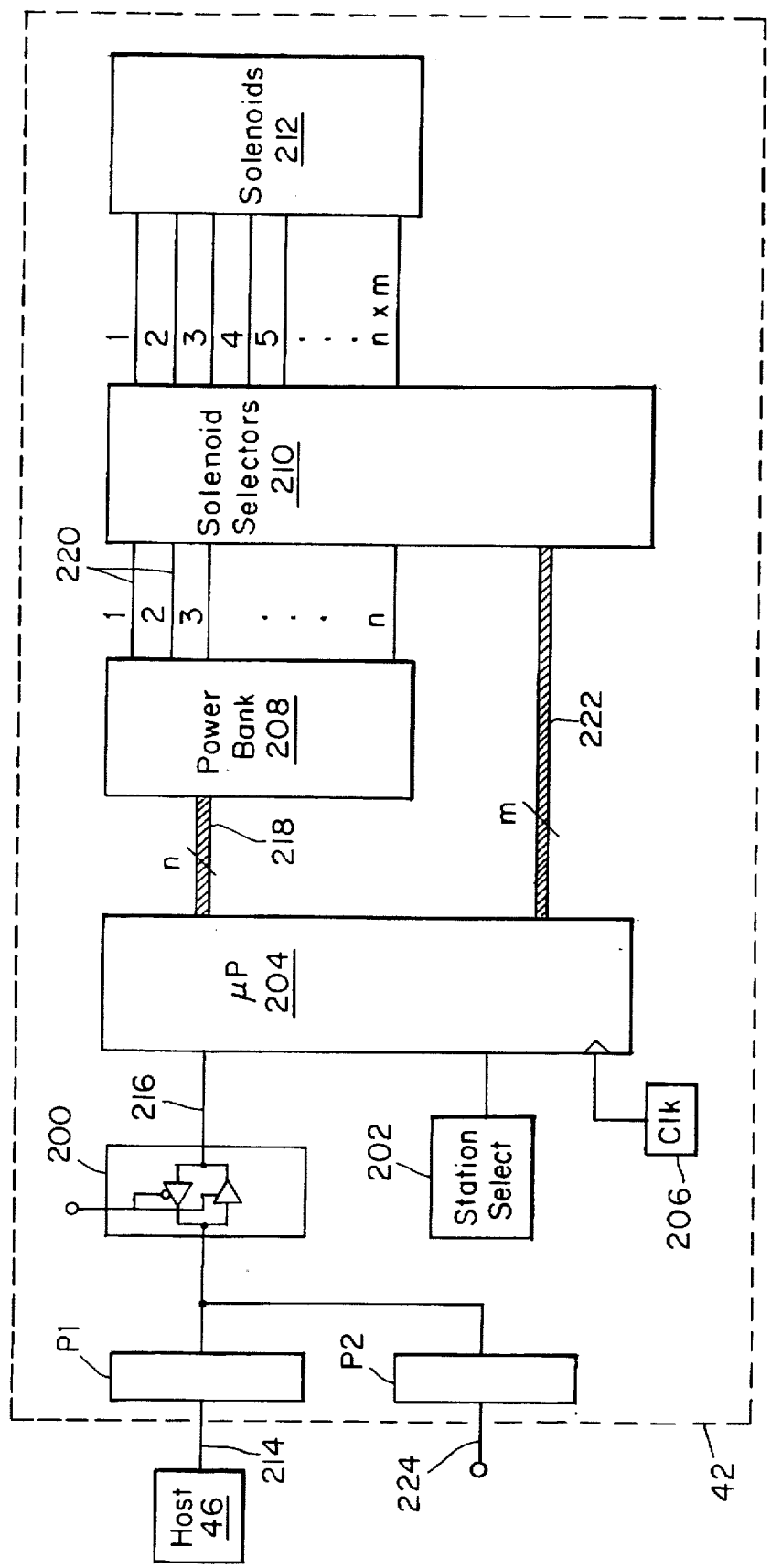
FIG. 9 is a schematic diagram of a circuit board using a controller for a drug dispensing system in accordance with the present invention.

FIG. 9 is a schematic block diagram of an RCD controller in accordance with the present invention. The host computer 46 is coupled to the RCD controller 42 via a standard serial interface, for example, an RS-232 interface. A port P1 receives the serial signal 214 and distributes it to a bidirectional tristate buffer 200. The buffered signal 216 enters a microprocessor 204 where it is decoded.

The microprocessor 204 decodes the serial signal 216 and activates an individual power blank line 218 and an individual solenoid line 222. The solenoids 212 are partitioned into n power banks 208, one power bank for each rack 24 in the cabinet. Each power bank 208 is activated by a data bus 218 output from the microprocessor 204. The power bank lines 220 are distributed to an array of solenoid selectors 210. The solenoid selectors combine the power bank signals 220 and solenoid signals 222 into an addressable array. If a power bank signal 220 is enabled, then power to the corresponding rack is activated. The solenoid signal 222 enables a particular solenoid 212 in the activated rack for dispensing. The solenoid signal bus 222 is m bits wide for selecting one of the m solenoids in the rack 24.

As stated above, the RCD cabinets can be daisy-chained so that a plurality of cabinets 20 are controlled by the same host computer 46. A second port P2 on the controller board 42 passes the serial signal 214 to the next board in the chain 224. A station-select switch 202 provides additional decoding so the controller 42 has knowledge of its address in the chain.

Figure 10:
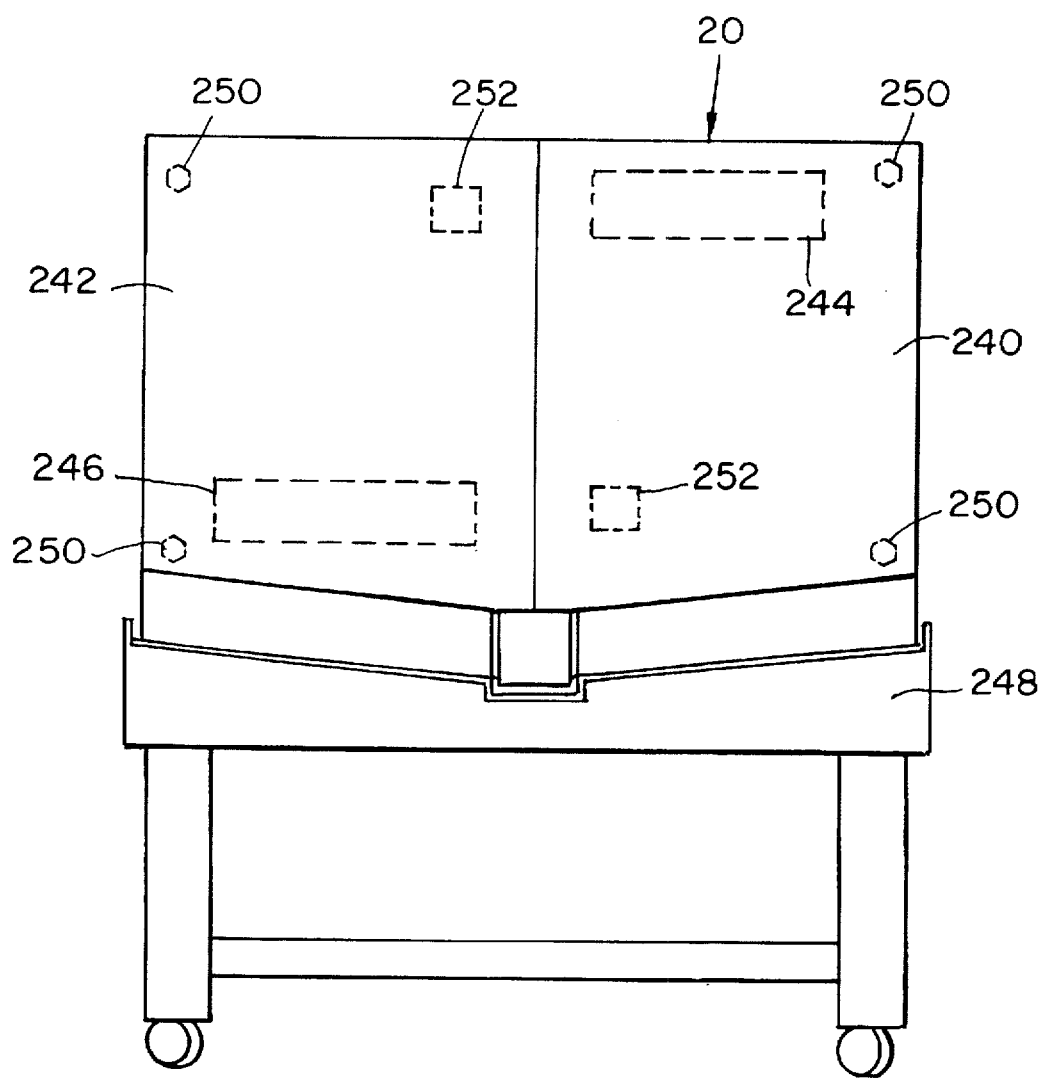
FIG. 10 is front view of a dispensing system on a rollable cart in accordance with the invention.

Another preferred embodiment of the invention is illustrated in connection with FIG. 10 where a dispensing cabinet 20 is positioned on a cart 248 having wheels and operable as a stand alone unit. The cart 248 can be used to support the unit relative to a wall surface in conjunction with bolts 250 or other suitable housing support mechanism. The housing support elements 250 can be used to support the cabinets 20 relative to the supporting surface without any other means for support.

Each cabinet 20 can also be insulated and provided with a cooling system 244 and/or a heating system 246. As illustrated, the cooling system 244 can be contained within the housing 20 on the frame of door panel 240. The heating systems can be used in the same panel 240 or in the adjoining panel 242. This system provides for the heating and/or cooling of selected drugs that require temperature regulation for storage. Many antibiotics, for example, must be maintained at a temperature of between 40°–50° F. to remain viable. One or more temperature sensors 252 can be positioned in the housing to monitor temperatures which can be regulated by controller and be recorded in computer 100 memory.

The remote pharmacist concept is an extension of the remote control dispensing capabilities of the present invention. A computer workstation is provided to assist a technician or other registered pharmacist in the filling of prescriptions. In general, this comprises several steps which are listed below:

1) retrieve the patient inquiry data—this defines the patient for whom the prescription is intended; the allergy, drug, and disease states of the patient; and the insurance payor(s) of the patient;

2) select the drug, signa, and other prescription-related parameters such as "refills authorized", "dispense as written", "compound code", etc.;

3) select the prescriber identification number;

4) verify information in steps 1, 2, and 3 against the prescription;

5) perform drug utilization review (DUR);

6) submit claim to payor;

7) dispense and verify drug package;

8) print and attach patient label to drug package;

9) verify correct label attached to drug package;

10) provide patient with label drug package and associated documentation such as receipt, patient counseling text, refill instructions, etc.;

11) provide patient with oral counseling when required or appropriate.

In traditional practice, a registered pharmacist physically located at the dispensing site performs all of the above steps. In some contemporary situations, a pharmacy technician may perform steps 1, 2, 3, 6, and 7, and the registered pharmacist will perform steps 4, 5, 8, 9, 10, and 11. In this situation, both the pharmacy technician and the registered pharmacist are located at the dispensing site, where one registered pharmacist may serve several pharmacy technicians.

In some states it is required by law that a registered pharmacist performs steps 4, 5, 9, and 11. In these states, the registered pharmacist provides cognitive or consultative service and leaves the mechanical tasks associated with filling and dispensing the drug to the pharmacy technician. This allows the registered pharmacist to enhance his contribution to the medical care process by affording the pharmacist with more time to focus on those steps which best utilize the pharmacists training and expertise. The remote pharmacist (RRPH) concept of the present invention enables a registered pharmacist to provide the above-cognitive/consultative services without being physically located at the dispensing site. This is accomplished through use of modern telecommunications technology in conjunction with a computer-based pharmacy workstation. In this manner, the expertise of a registered pharmacist operating an RPH can be shared among a large number of pharmacy technicians, increasing the level of medical care provided in a cost-effective manner.

Figure 11A:
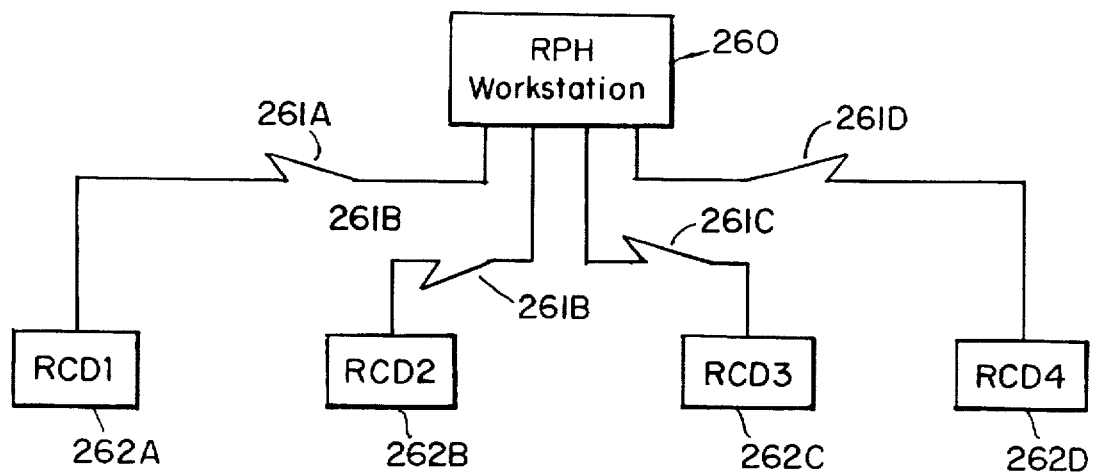
FIGS. 11A and 11B are block diagrams of system configurations in accordance with the present invention.

The RPH apparatus and method of the present invention is effective in several configurations. A first configuration is shown in the block diagram of FIG. 11A wherein an RPH 260 services several distinct RCD locations 262A–D. Each RCD 262A–D is at a distinct physical location and is connected to an RPH workstation 260 via a telecommunications link 261A–D, for example, a computer modem. This configuration is appropriate, for example, for servicing several low-volume clinics or emergency rooms where it is not economical to place a pharmacist. The mechanical tasks associated with dispensing the drug can be handled by an RCD pharmacy technician or by a qualified member of the medical or administrative staff. A pharmacist based at the RPH provides the pharmacy expertise needed for an effective dispensing process.

Figure 11B:
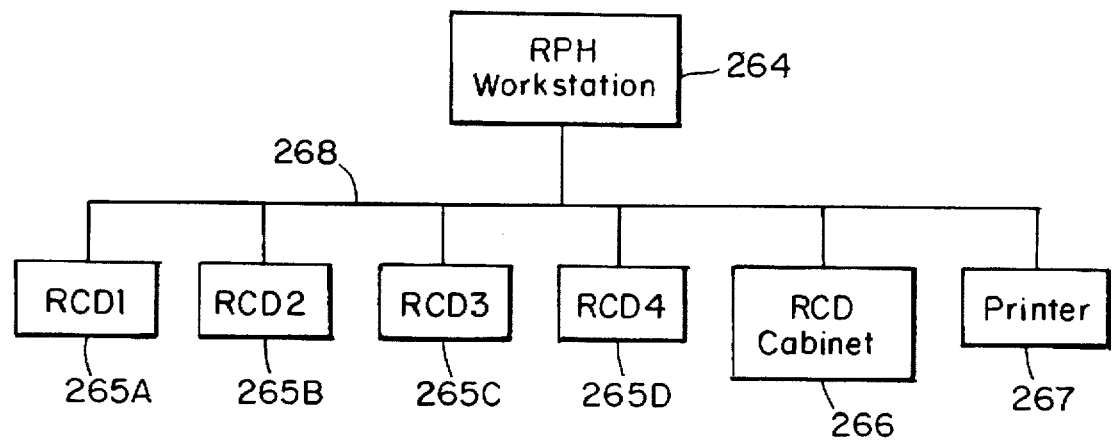

The configuration of FIG. 11B is applicable in a large volume clinic where several pharmacy technicians operating several remote control dispensers (RCD) units 265A–265D perform the mechanical tasks of steps 1–3 and 7–10 outlined above and a pharmacist operating an RPH workstation 264 performs the cognitive or consultative steps 4–6. In this configuration, the RPH workstation 264 can be, but need not be, located in the same facility as the RCD units 265A–265D. If they are in the same facility, the RPH workstation 264 can be linked to the RCD units 265A–D and an RCD cabinet 266 via a local area network (LAN) 268. In this configuration, a patient presents a prescription to a technician at one of the available RCD terminals 265A–265D. At this terminal, a pharmacy technician performs steps 1–3. The results are transmitted over the network to the RPH workstation, and the pharmacist at the RPH performs steps 4–6. After the pharmacist approves the transaction, the technician at the RCD unit performs steps 7–10. In high-volume situations, dispensing is performed at separate RCD cabinets 266 adapted for dispensing large quantities of pharmaceuticals. A label is printed at a printer 267 and attached to a pharmaceutical package, for example, a bottle. The bar code reader compares the bar codes of the bottle and label to ensure that the proper prescription has been dispensed. If so, the patient is presented the bottle and corresponding documentation.

Figure 12:
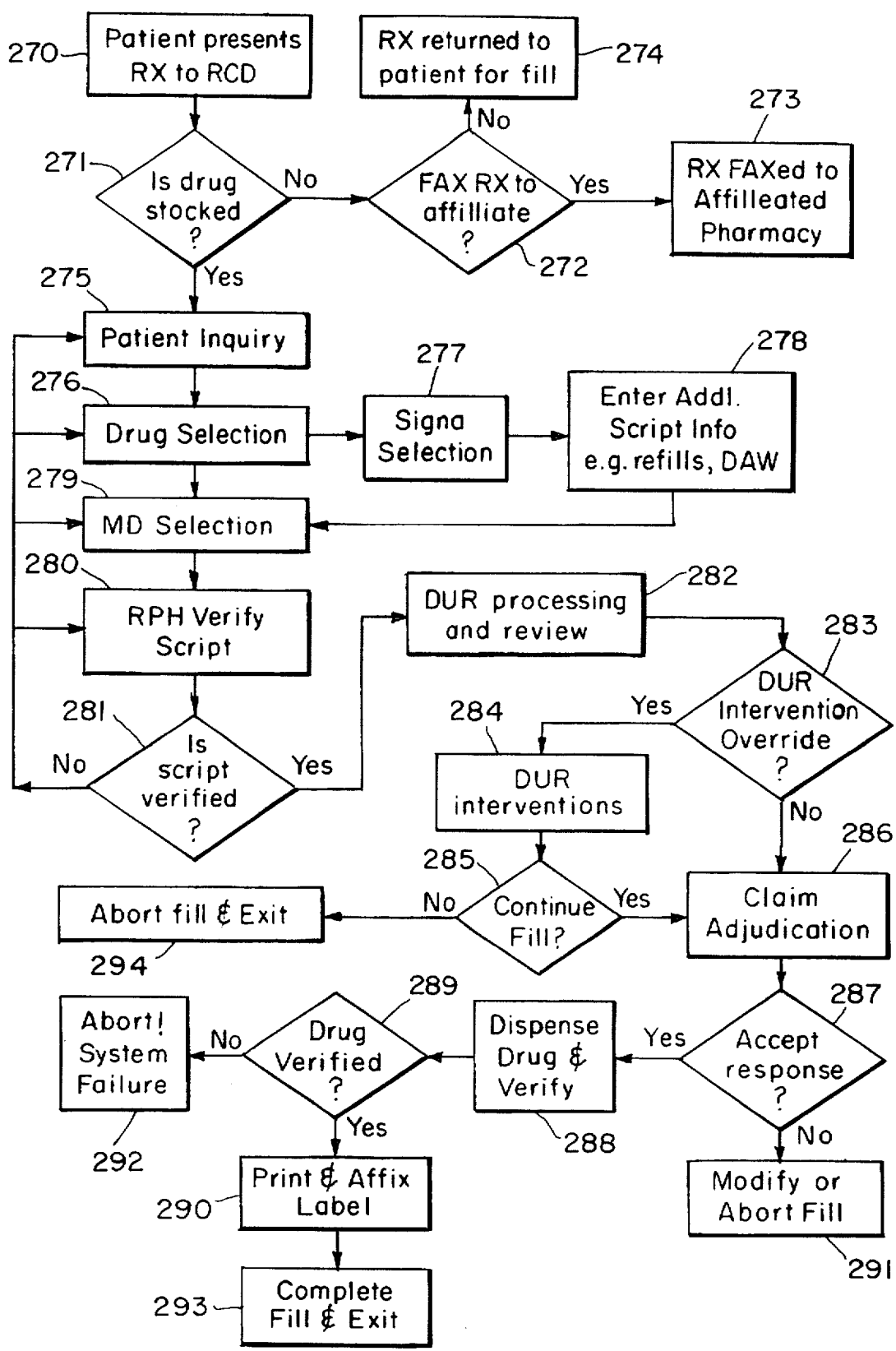
FIG. 12 is a flow diagram representing the processes performed by the pharmacy technician at an RCD and a registered pharmacist at an RPH in accordance with the present invention.

FIG. 12 is a flow diagram representing the processes performed by the pharmacy technician at an RCD and a registered pharmacist at the RPH in accordance with the present invention. Initially, a patient presents a prescription to a technician at an RCD unit 270. The technician determines whether the drug is stocked in the RCD unit 271. If the pharmaceutical is not stocked, then the technician decides whether to electronically transfer via facsimile, email, or otherwise, the prescription to an affiliate 272. If the prescription is transferred to the affiliated pharmacy, 273, the patient may travel to that pharmacy to receive the pharmaceutical. Otherwise, the prescription is returned to the patient 274 to be filled at another RCD unit or by another pharmacist of the patient's choosing.

If the drug is stocked at the RCD unit, then patient data is retrieved 275, the drug is selected 276, the prescription signa is selected 277 and additional scripts may be entered 278. Following this, the identification number of the prescriber is entered 279 and all data is transmitted to the RPH workstation 280. At the RPH workstation, the pharmacist verifies the prescription 281 and performs a drug utilization review 282. If issues arise during the review, the pharmacist is immediately made aware of the conflict and given an opportunity to review and, if appropriate, override 283 the interventions 284. If the pharmacist decides at this point to discontinue the dispensing 285, the process is aborted 294. If the pharmacist decides to continue the dispensing anyway 284 or there were no interventions 283 in the first place, then claim adjudication is performed 286. During adjudication 286, a patient's insurance information is automatically verified to determine whether the insurer will pay for the prescription, and if so, if any co-payment is required from the patient. If a negative response is received 287, drug dispensing is aborted 291. Otherwise, the drug is dispensed and verified with a bar code reader 288. If an improper drug was dispensed, the technician is notified to abort the process as a system failure has occurred 292. Upon system failure electronic notification is performed. Distribution headquarters or a regional dispensing location or agent can be notified by the RCD system of an incorrect dispense is shown. Electronic notification can take the form of a fax, email, file transfer, pager notification, or any other electronic transfer protocol. If verification is positive, a label is printed and affixed to the bottle 290, and the prescription is dispensed to the patient by the technician 293.

Figure 13A:
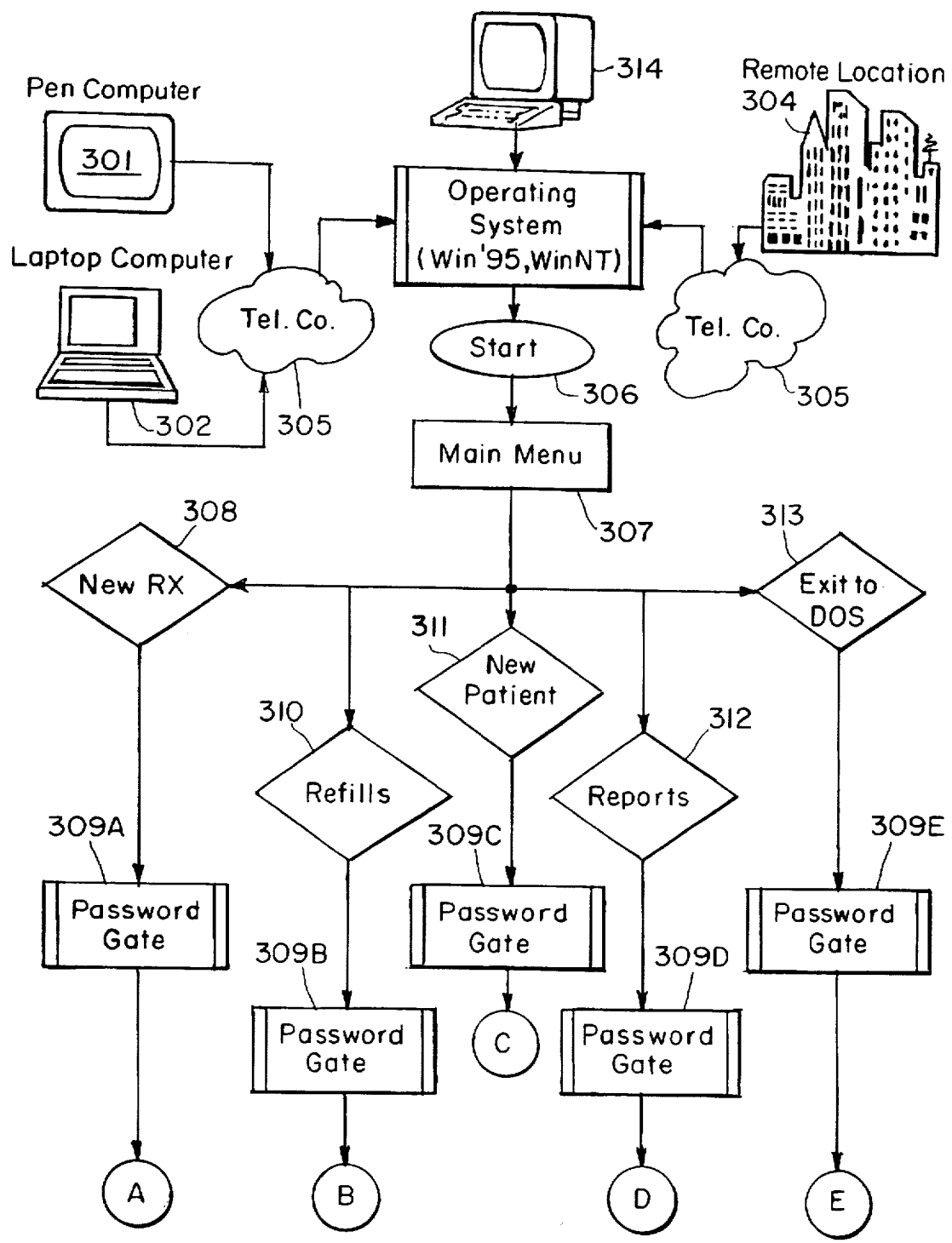
FIGS. 13A–13Q are flow diagrams representing the software operating on the remote pharmacist (RRPH) workstations.
Figure 13B:
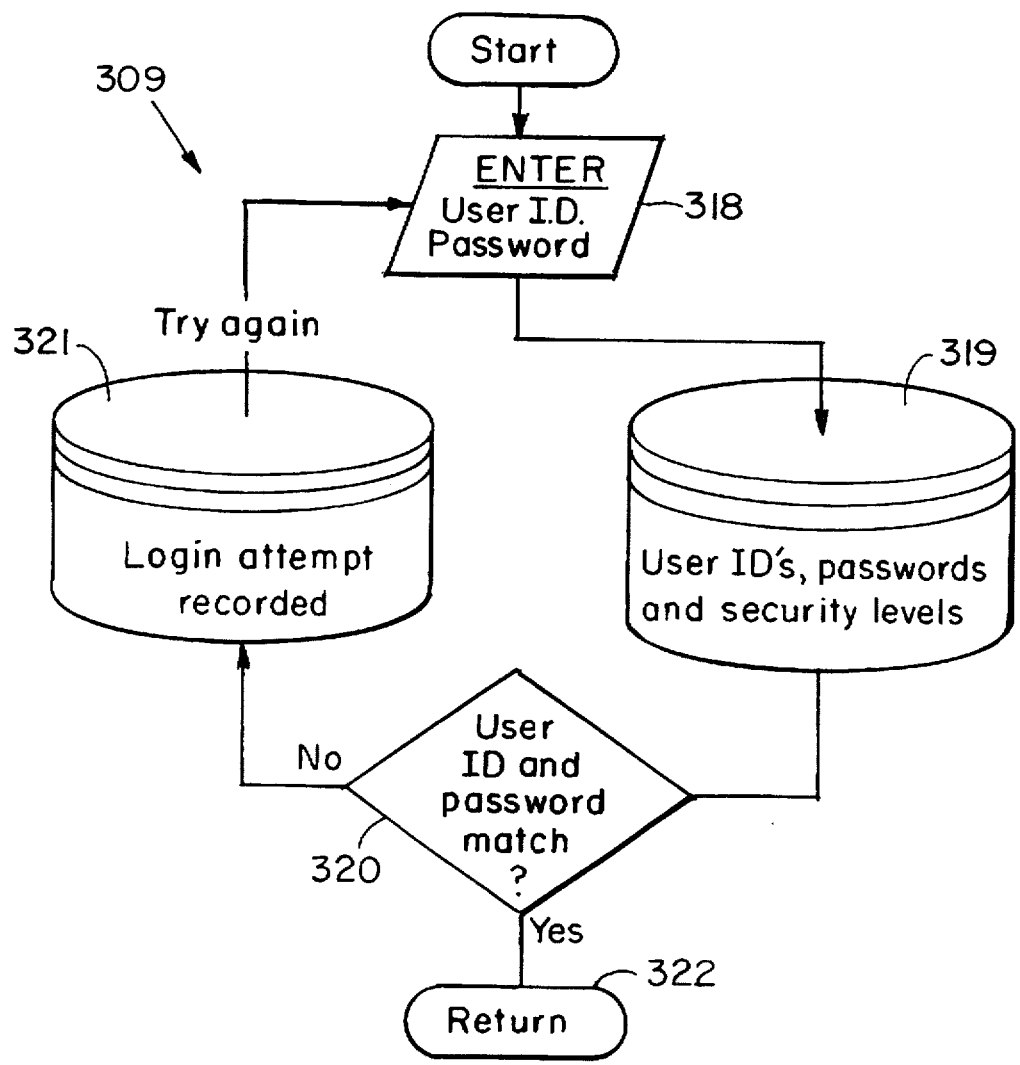
Figure 13C:
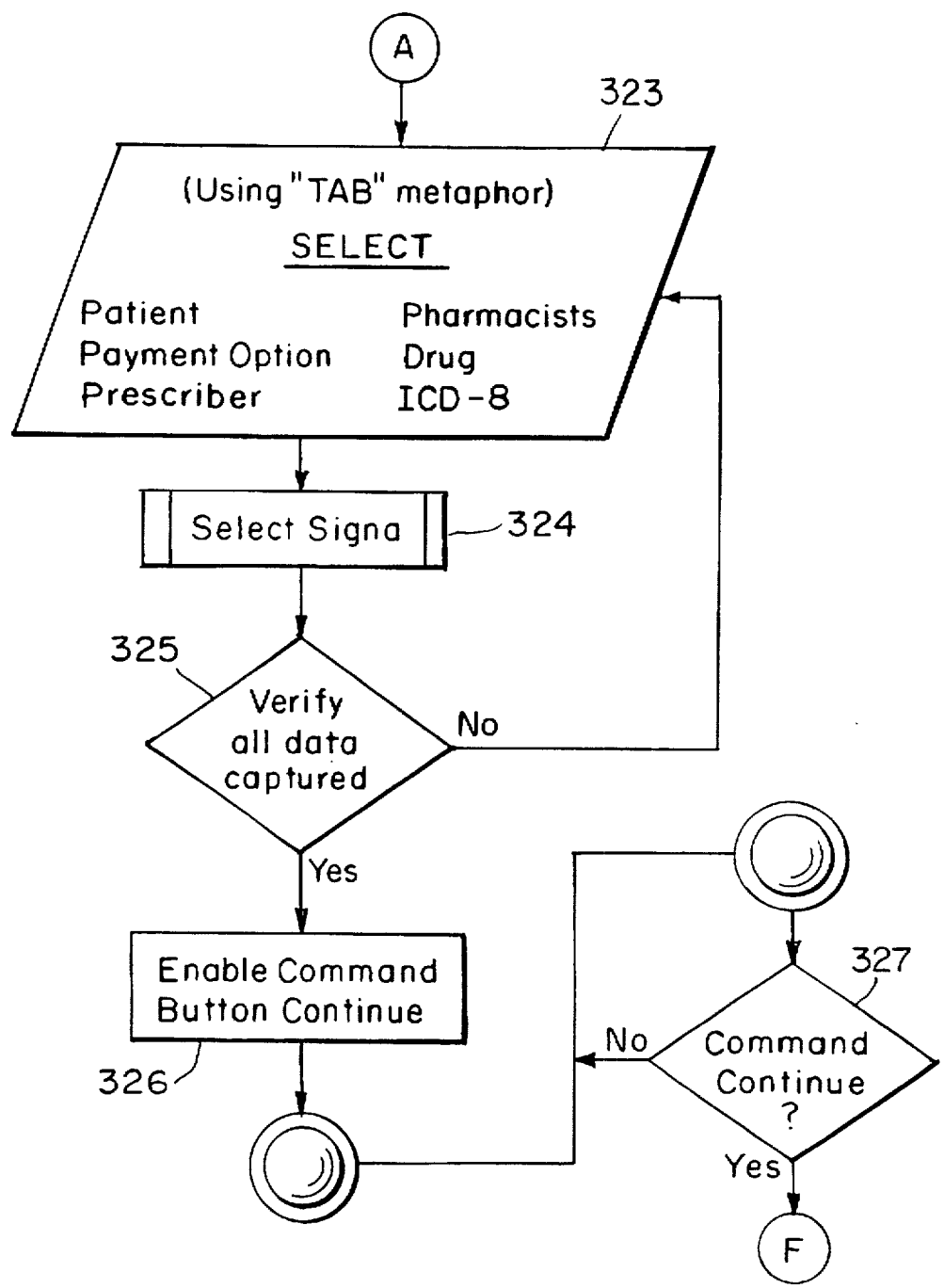
Figure 13D:
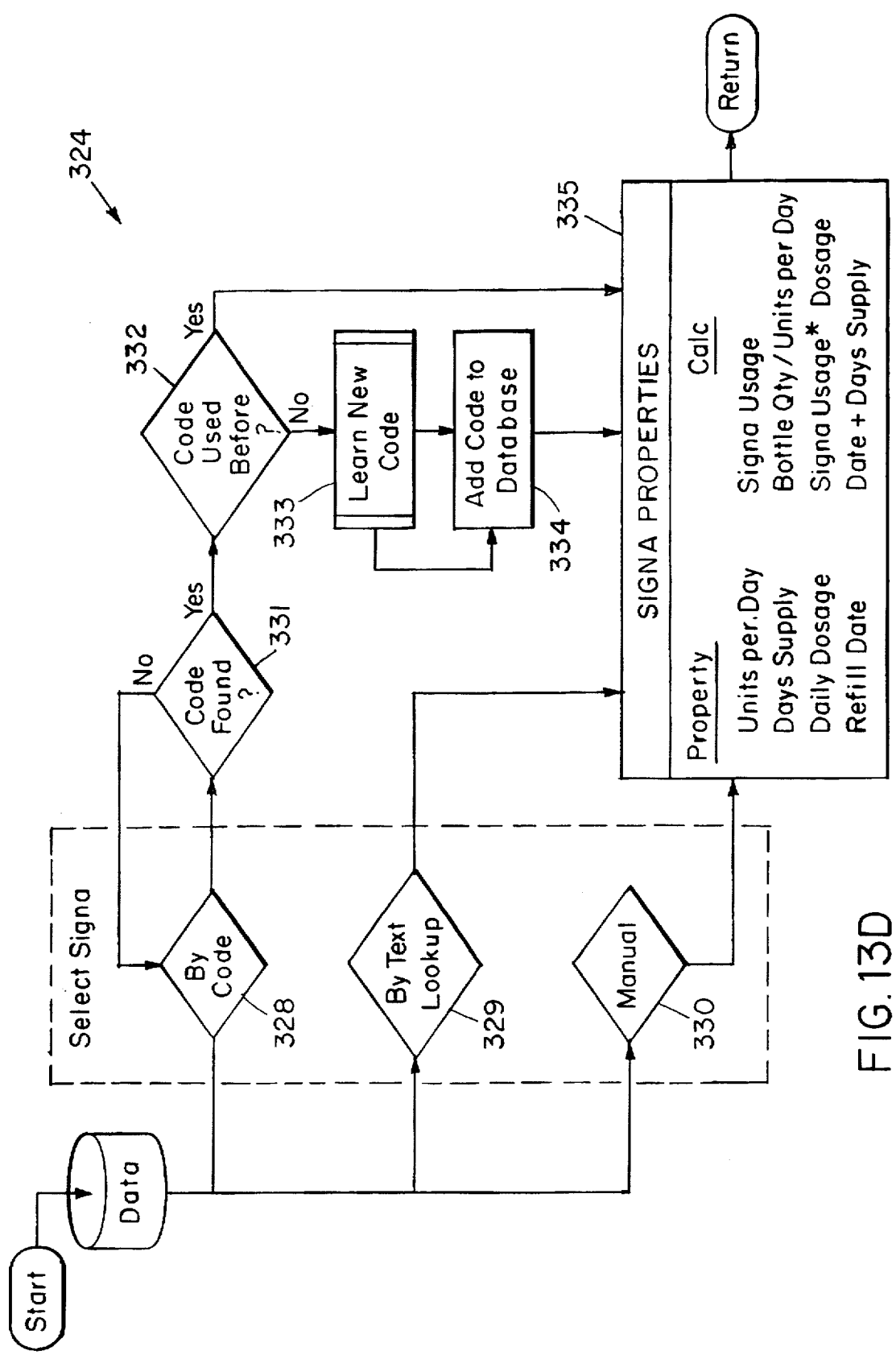
Figure 13E:
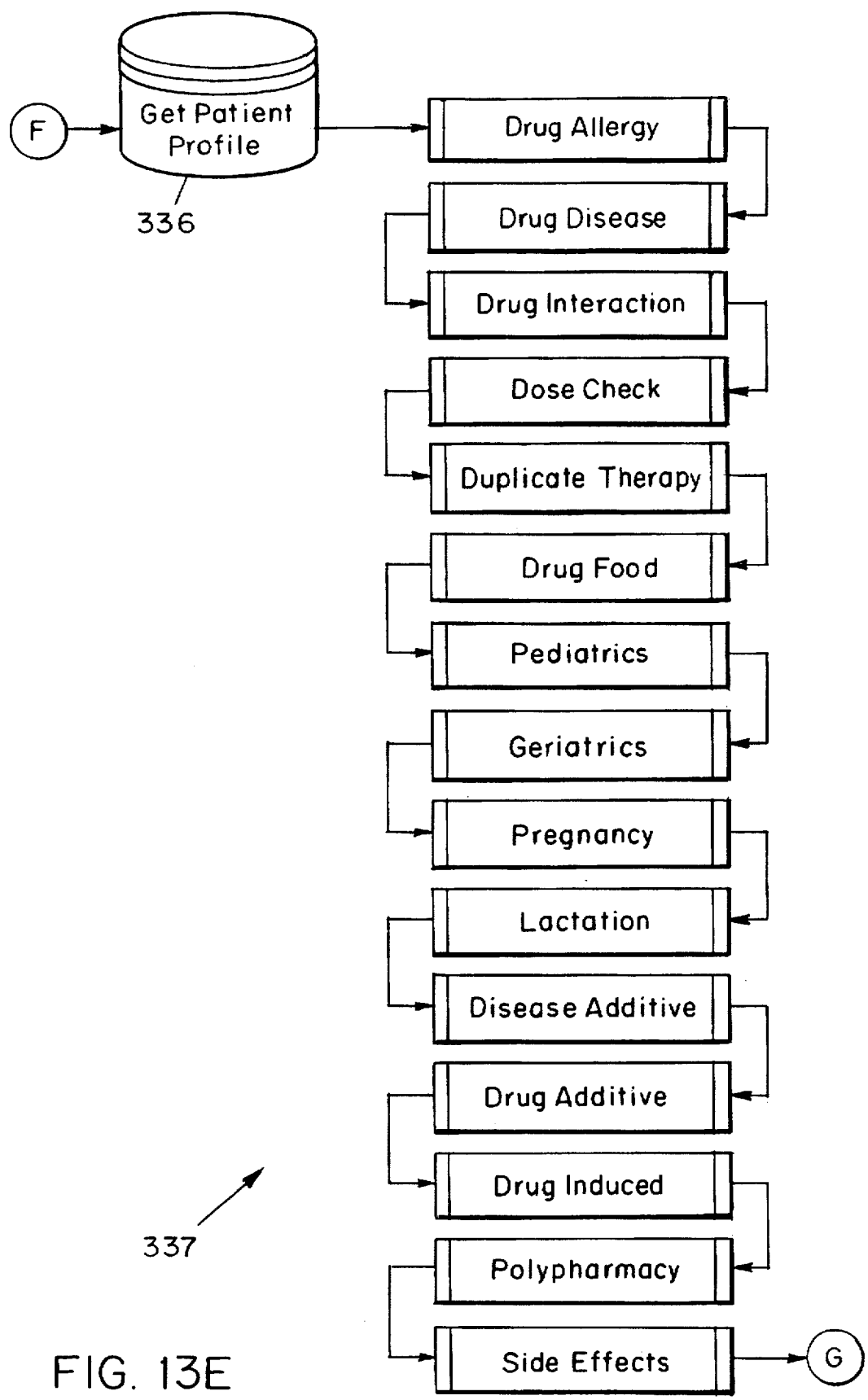
Figure 13F:
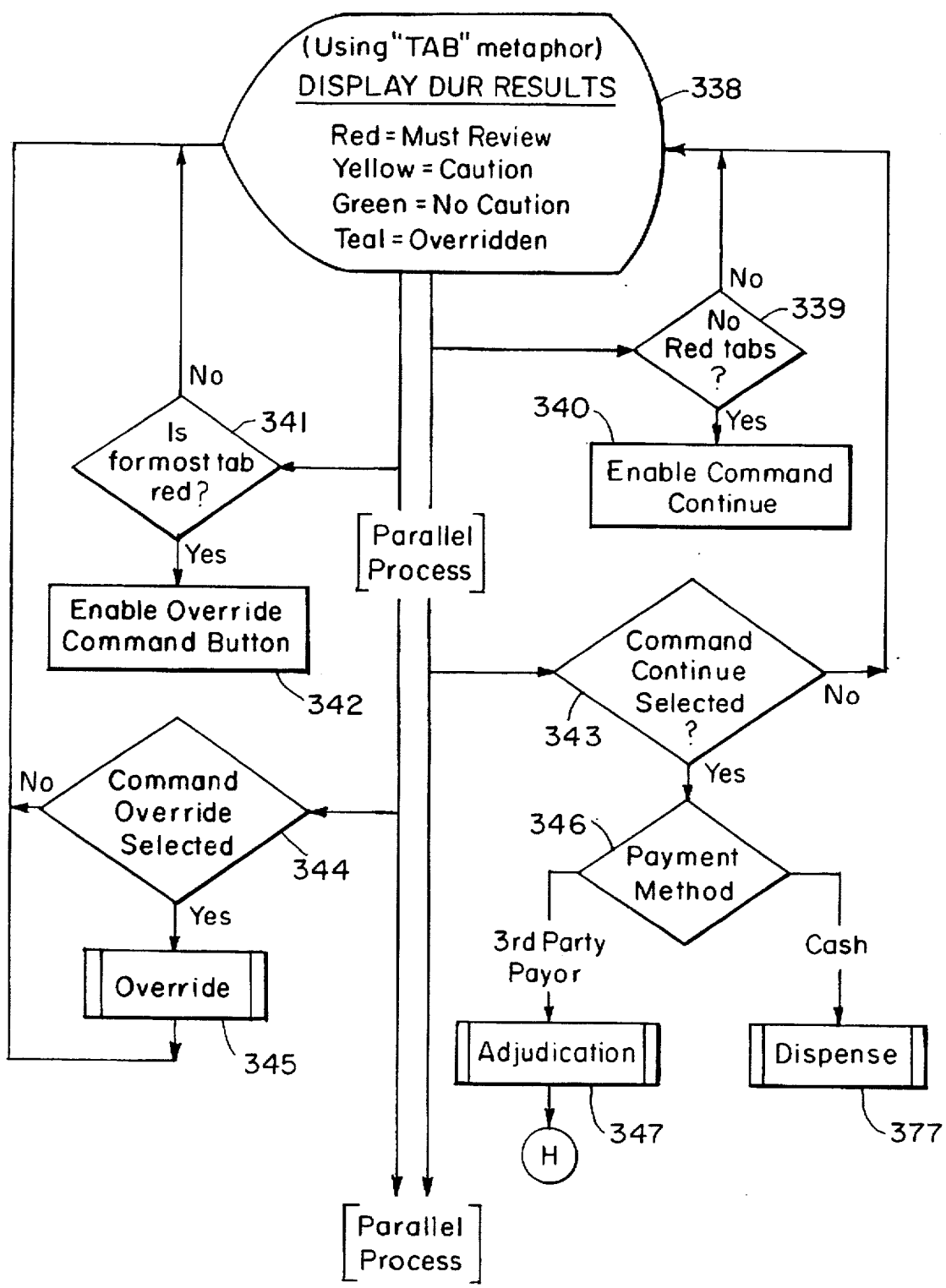
Figure 13G:
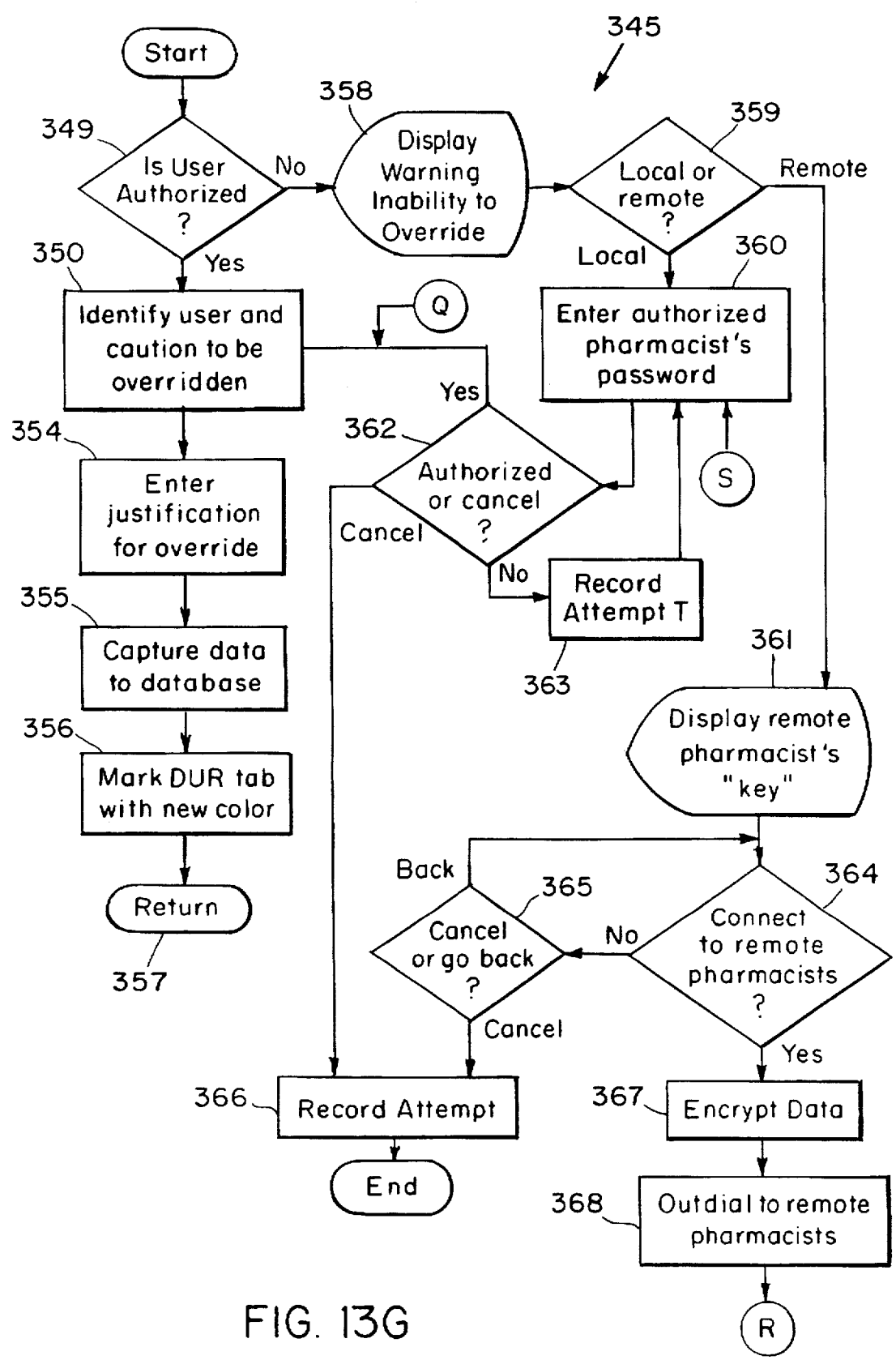
Figure 13H:
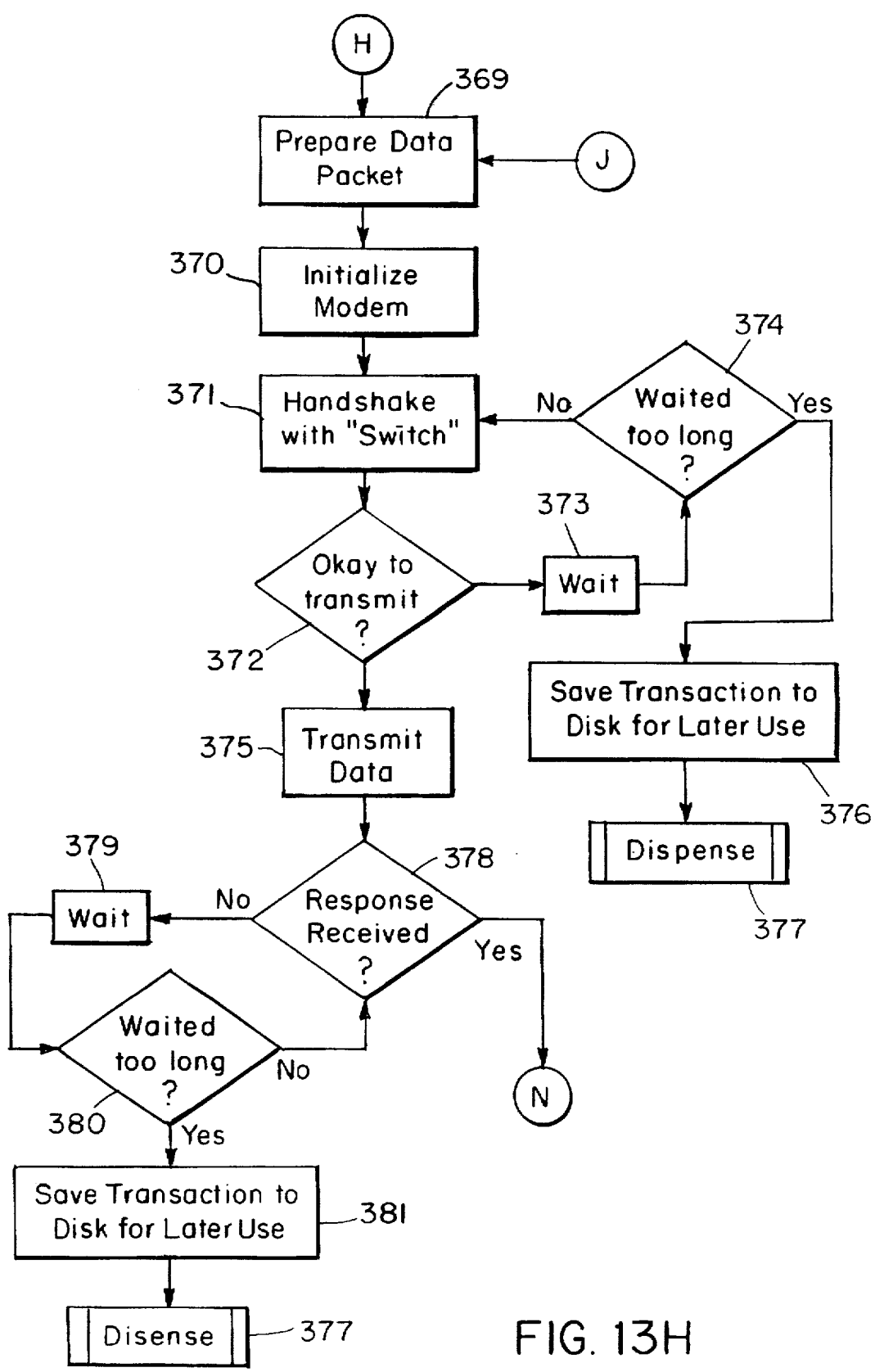
Figure 13I:
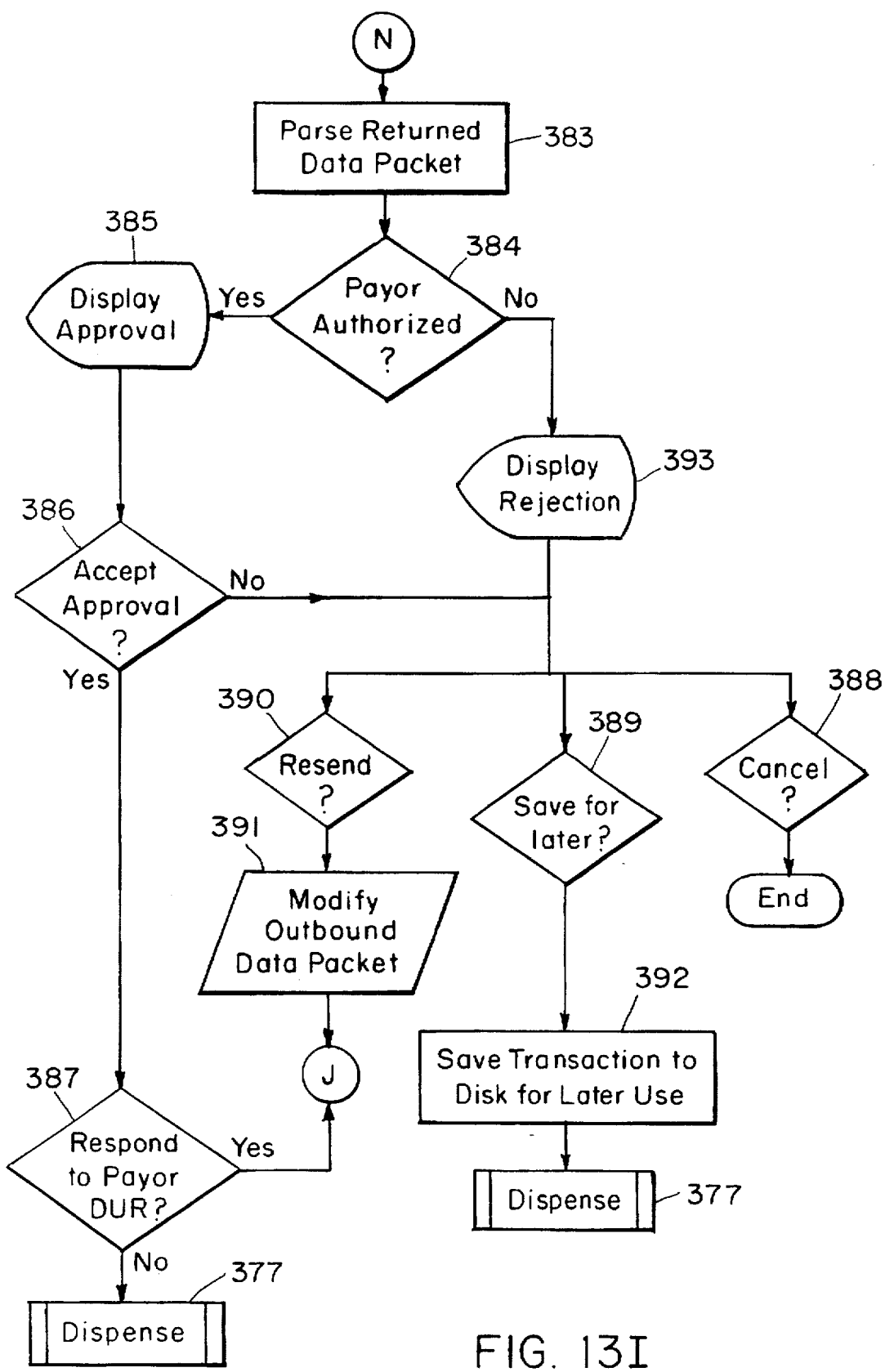
Figure 13J:
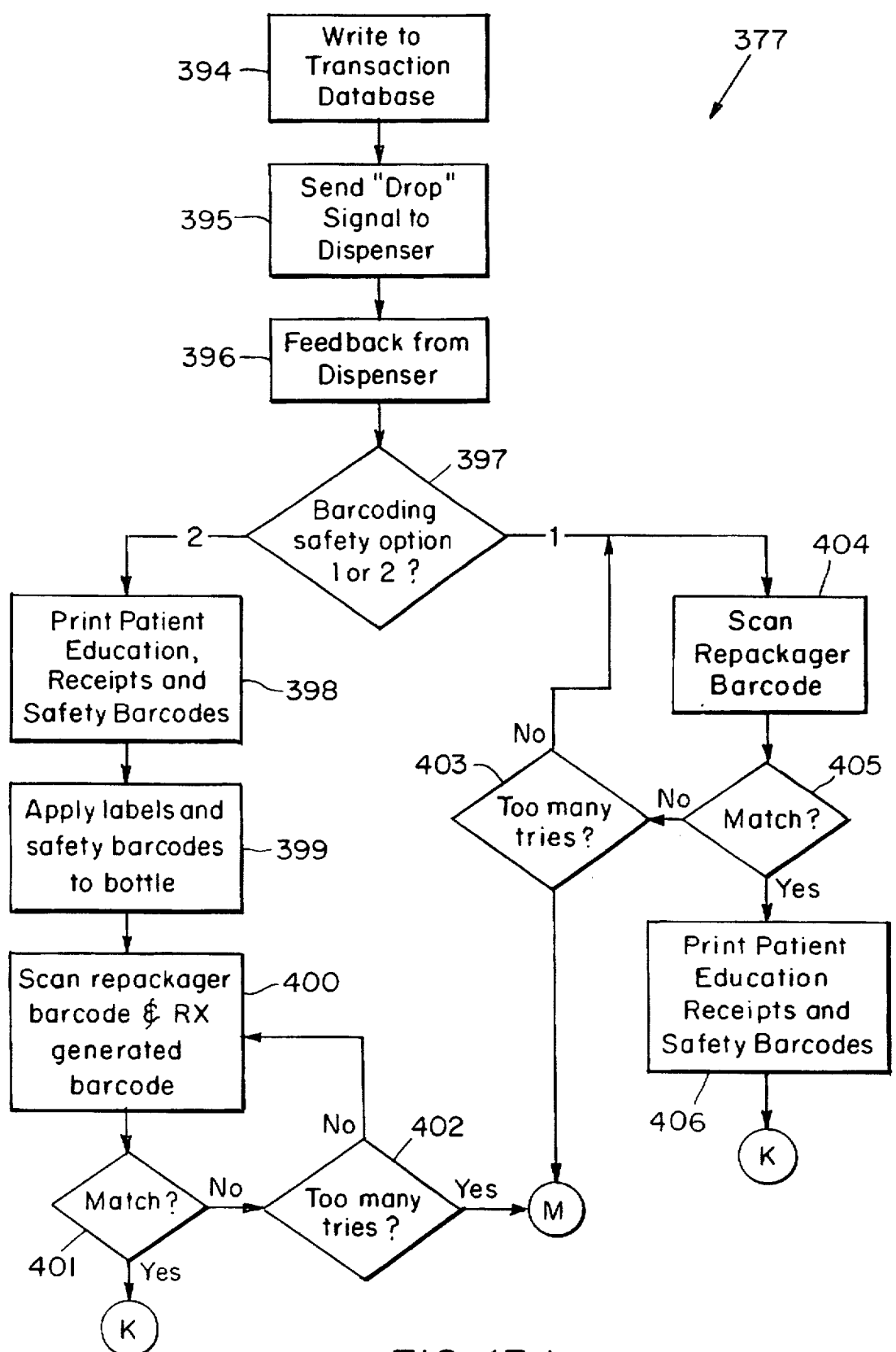
Figure 13K:
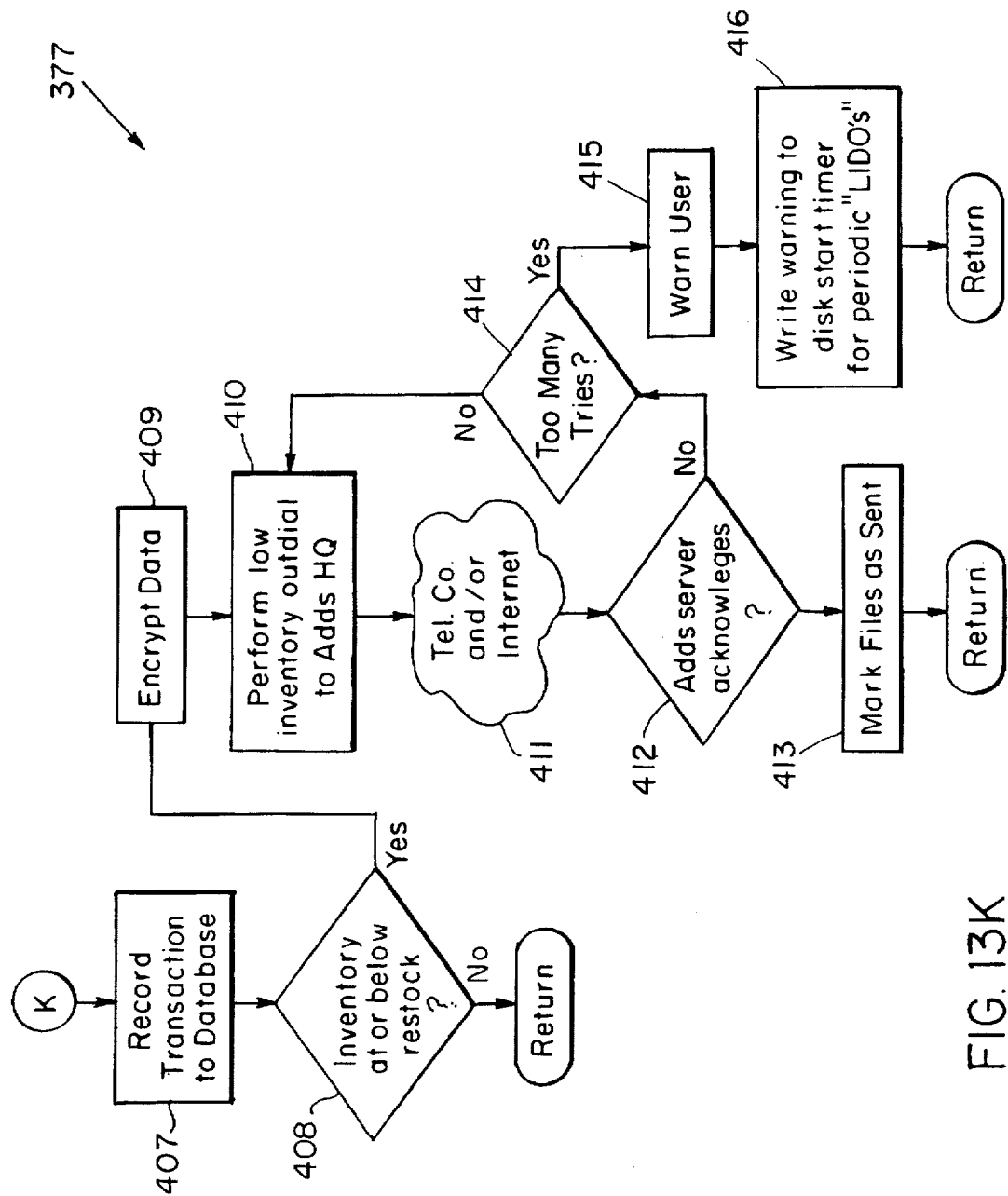
Figure 13L:
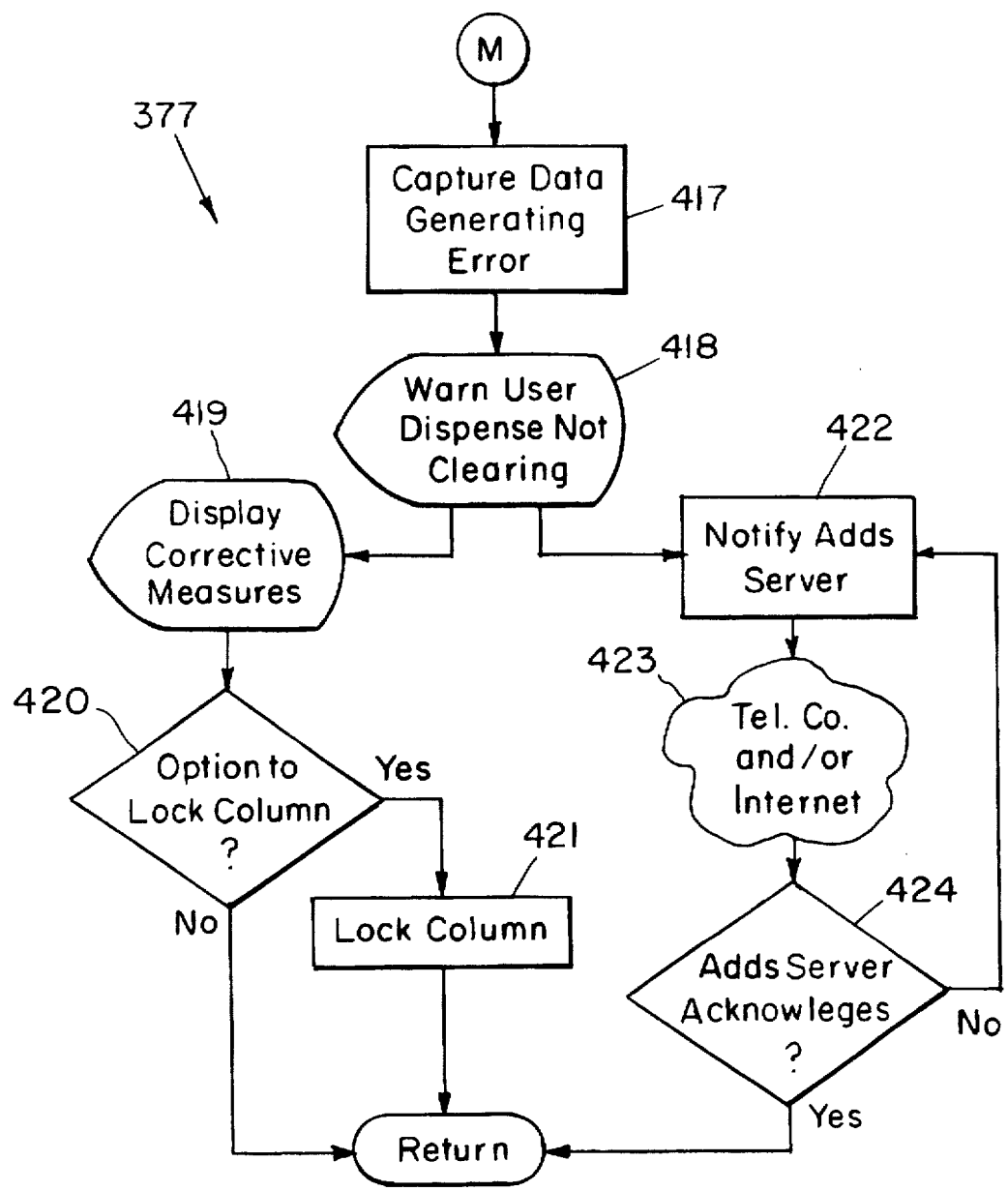
Figure 13M:
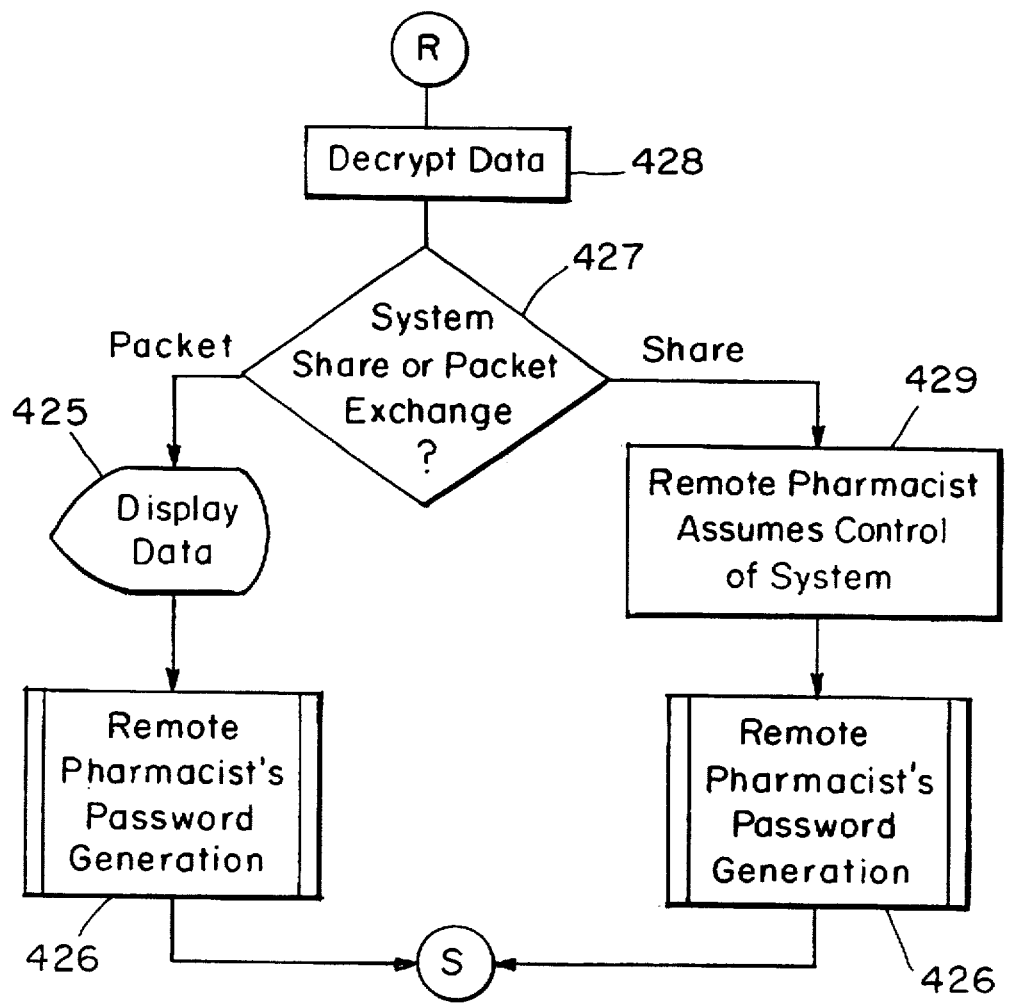
Figure 13P:
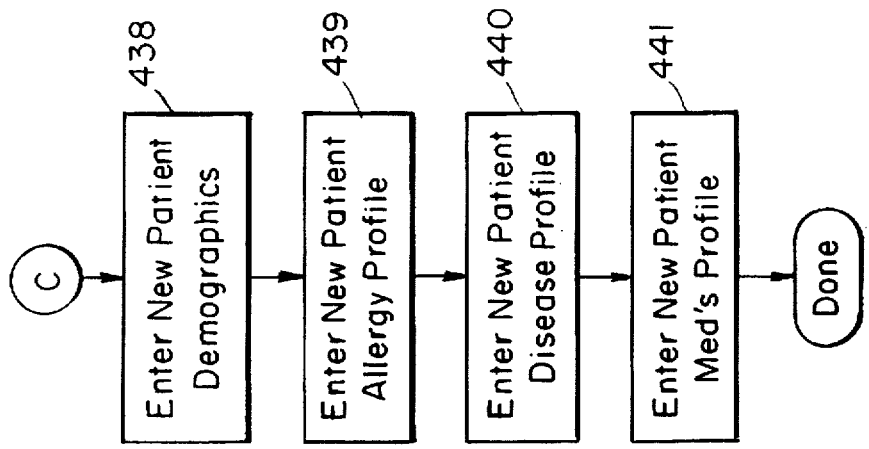
Figure 13O:
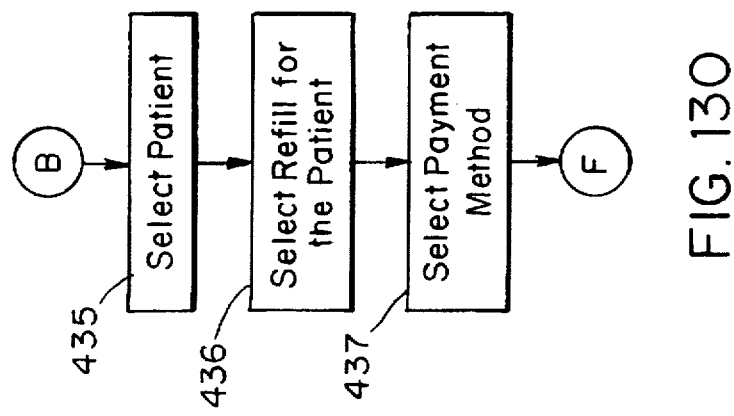
Figure 13N:
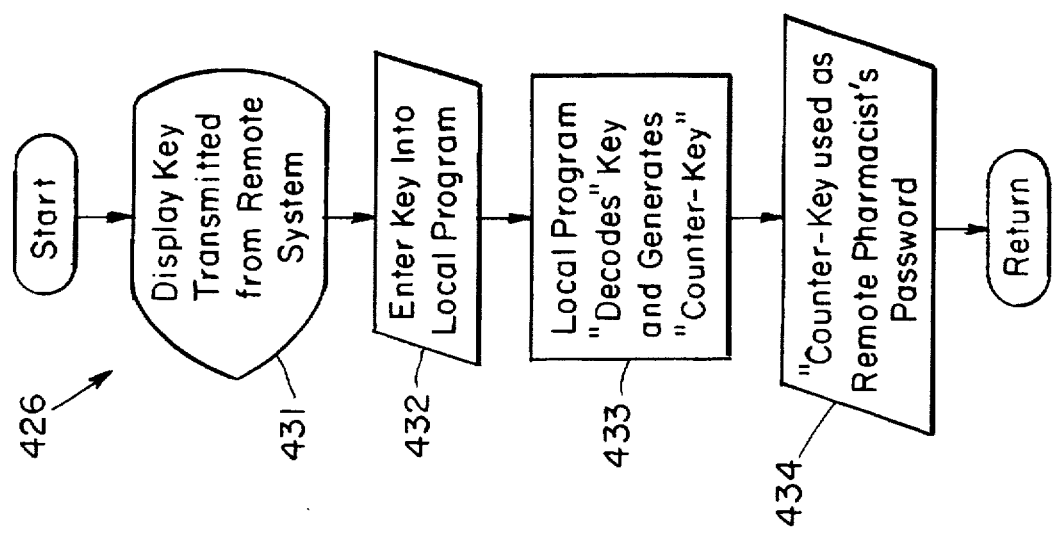
Figure 13Q:
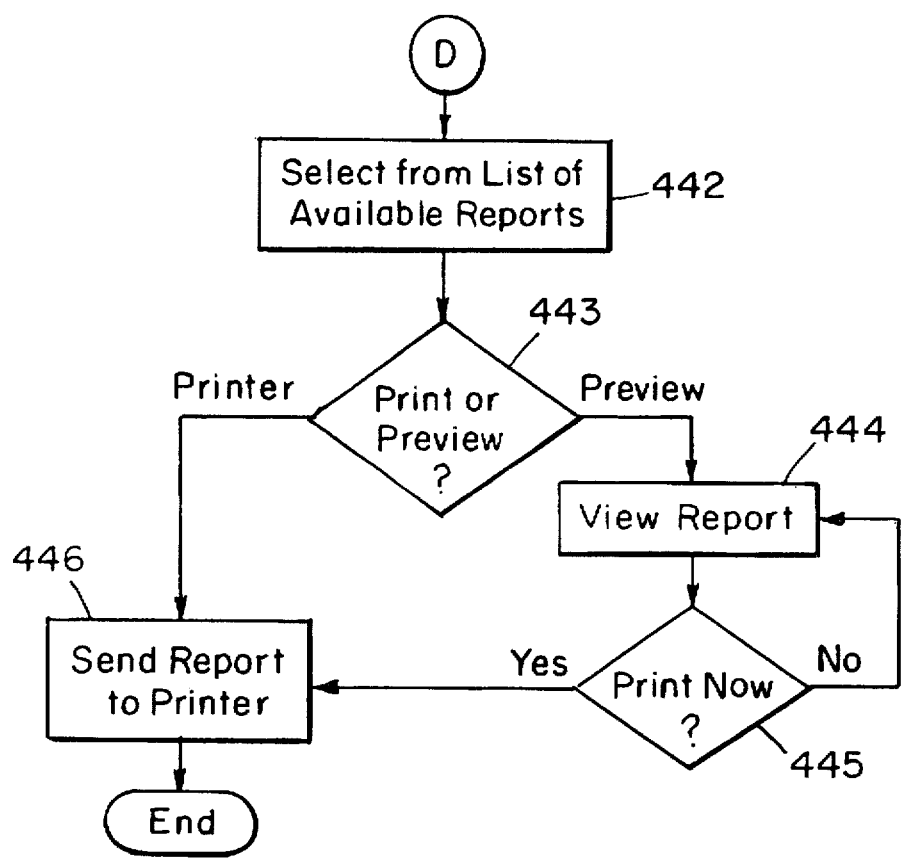

FIGS. 13A–13Q are flow diagrams representing the software operating on the remote pharmacist (RRPH) workstation 314. The system is accessible in a variety of configurations and on a variety of platforms including a pen computer 301, a laptop computer 302, and a workstation 314 accessing the system either at an on-site location or through a telephone network 305. The pharmacist can also access the system via telephone modem 305 from a remote location 304 anywhere in the world. The operating system is preferably a windows-based system, for example, OS/2™, Windows 95™ or Windows NT™. A programming language, for example, OS Visual Basic™, Borland Delphi™ and various tool kits such as OCX-VBX Library Kits and ButtonMaker by FarPoint Technologies™ provide the framework for supporting the Windows environment. The windows environment is preferably mouse-driven and may optionally employ voice-activated technology touch screen, or wireless hand-held terminals that remotely control the RRPH, such as a Zenith Data Systems Cruisepad™, for ease of use.

Upon entering the operating system 303, the program starts 306 at a main menu 307. The main menu 307 is referred to as a jump screen shown in FIG. 14A. At the jump screen 500, the operator can select from several options including: entering a new prescription 308, refilling a prescription 310, entering new patient information 311, generating reports 312, performing maintenance functions 315, or exiting the system 313. Each selection requires the operator to enter a password 309A–309E. The password function 309A–309E provides an appropriate level of security for each task. For example, generating a new prescription 308 may require a high level of security, for example, the pharmacist, while generating a report 312, may require a lower level of security, for example, a technician.

Figure 14A:
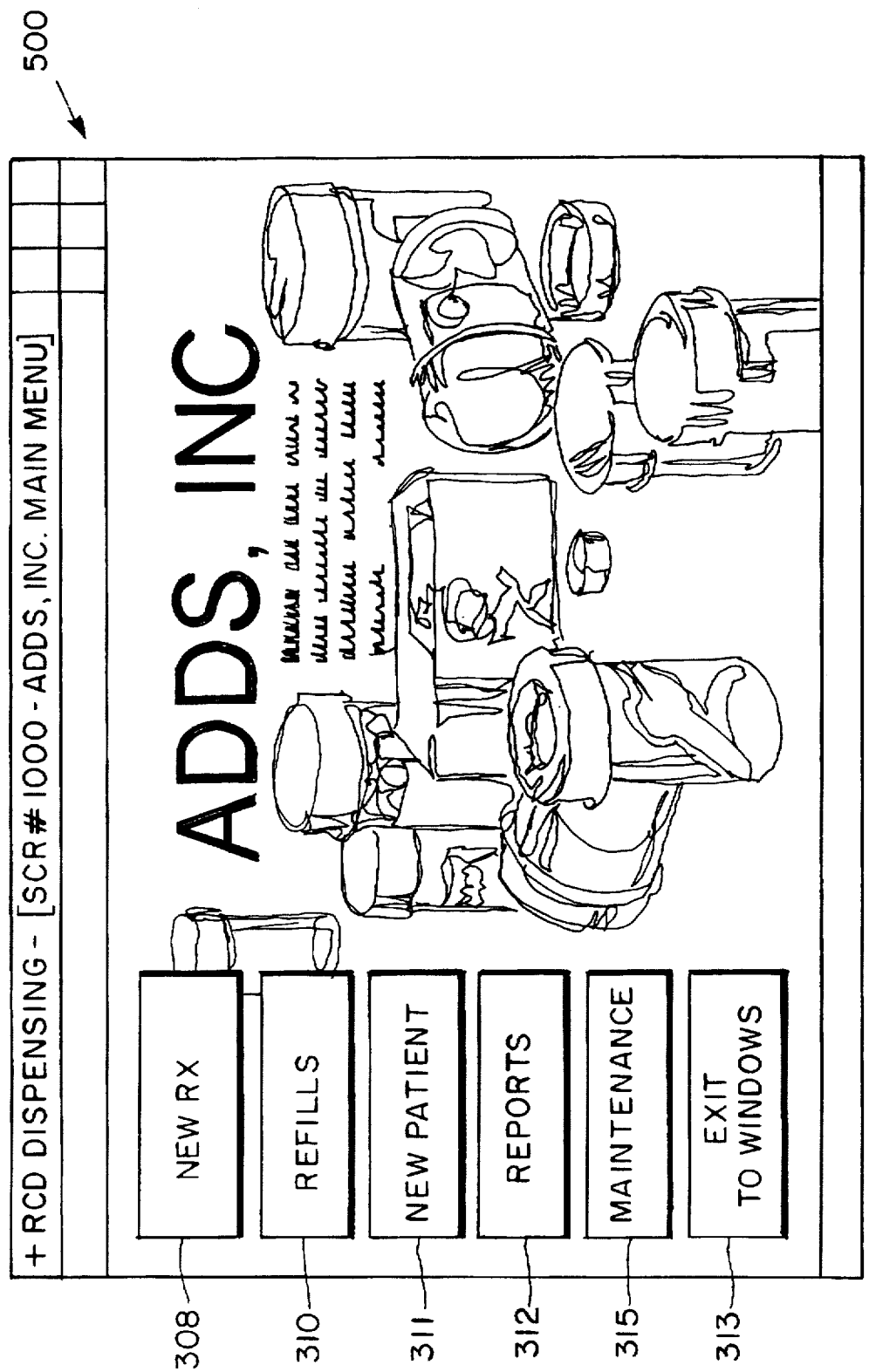
FIGS. 14A–14V are images of the user interface for the RPH workstation software.

The password gate task 309 is shown in FIG. 13B. Initially, the user is prompted to enter a user ID and password 318 which is checked against a database 319 of user IDs, passwords, and security levels. The screen for entering the username and password is shown in FIG. 14Q. If the user ID and password are verified 320, then the operator is permitted to proceed and the system is returned 322 to the operation where the password task was initially called. Otherwise, a login attempt is recorded 321 and the user is prompted again to enter his password 318. Security measures may be installed to prevent break-ins. For example, when a predetermined number of invalid login attempts 321 are recorded, the system may be disabled for a period of time.

Figure 14B:
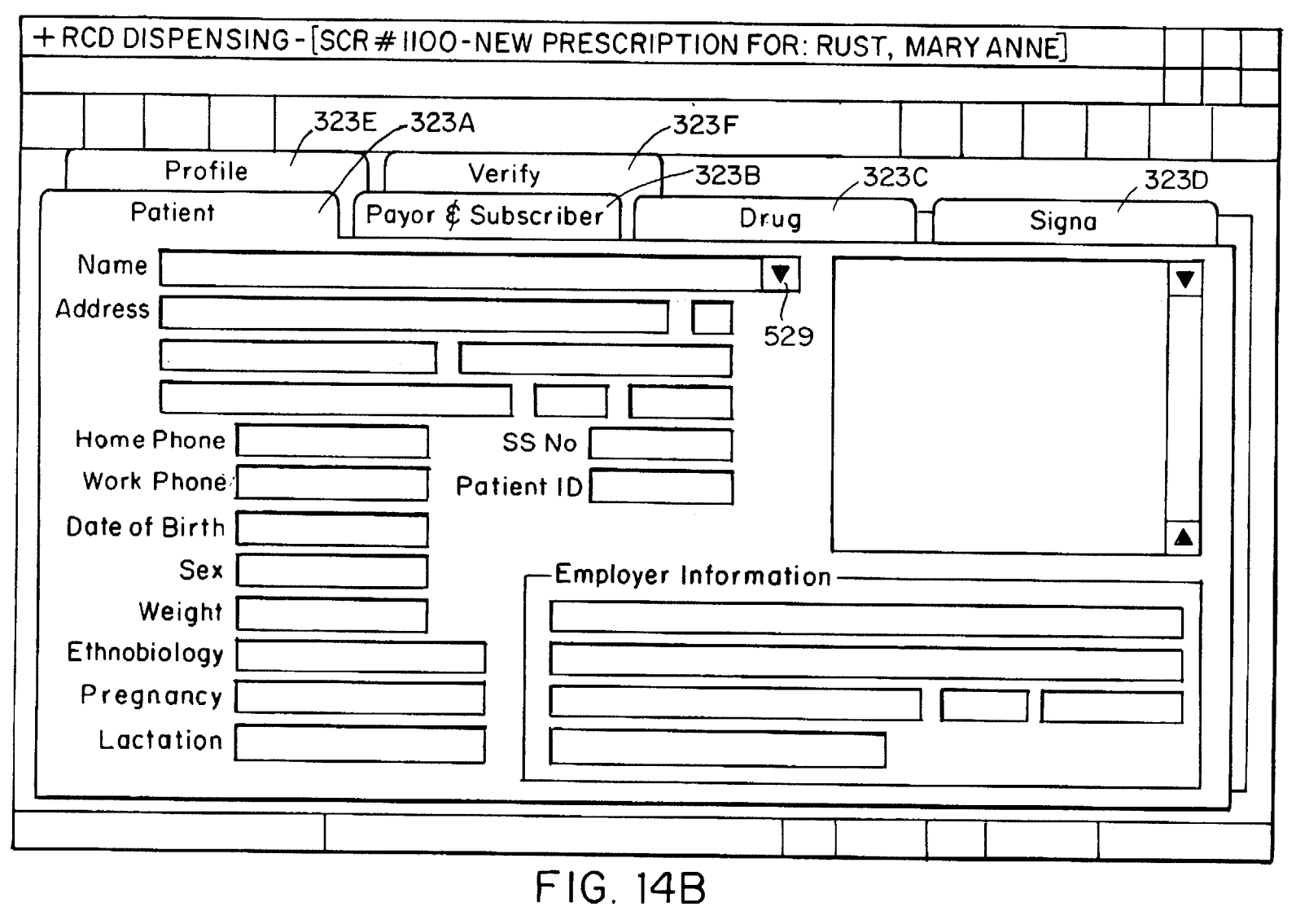

Returning to FIG. 13A, if the option to enter a new prescription 308 is selected and a proper password is entered 309A, then the operator is presented with a menu of selections shown in FIG. 14B. The menu is generated using a tab metaphor representing a plurality of files for the user to "thumb" through using the mouse. The tab selections include patient information 323A, payment 323B, drug 323C, signa 323D, patient medical profile 323E, and data verification 323F. In the patient window 323A shown in FIG. 14B, the operator is prompted to enter fundamental data concerning the patient including name, address, phone numbers, age, sex, weight, identification numbers, basic health information, and employer information. Alternatively, the operator may use the drop-down box 529 to select the patent name from a list. In which case the relevant data will automatically appear in the data windows.

Upon entering the above data, the operator next selects the payor and prescriber window 323B shown in FIG. 14C. In this window, the operator is prompted to enter information about the prescribing physician 501, the responsible pharmacist 502, and the person or insurance company responsible for payment 503. Pull-down menus indicated by arrows 504A, 504B are provided to allow the operator to select from a plurality of prescribers and pharmacists previously entered into the database. Upon selecting a prescribing physician from the pop-down menu 504A, the relevant data 501 will automatically appear in the data windows. This patient data can be required before an enabling command can be sent to the controller and/or printer to dispense the desired item or print the necessary labeling an/or patient instruction printout.

Figure 14D:
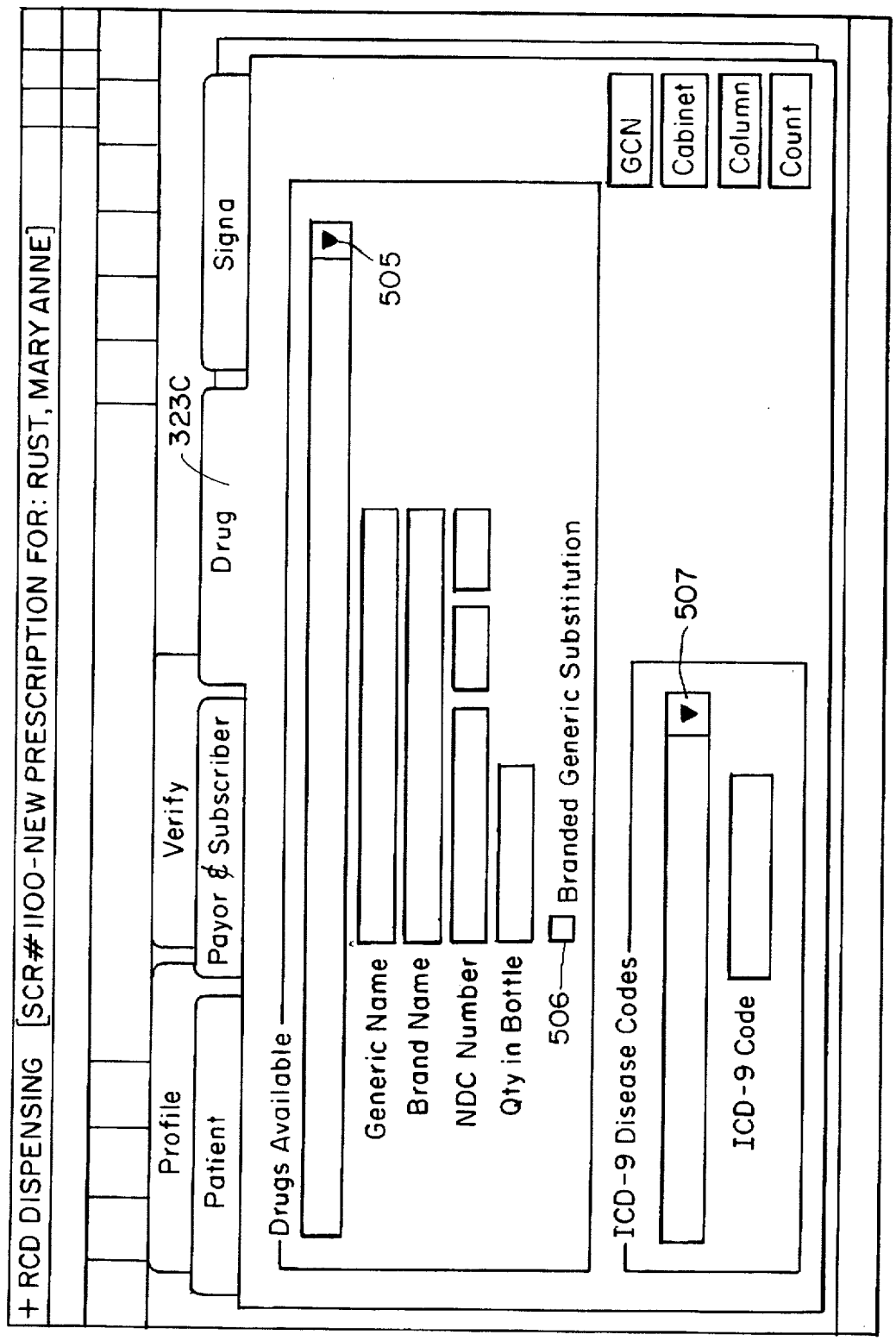

In the drug window 323C, shown in FIG. 14D, the operator is prompted to select from a pop-down menu 505 of drugs available in the RCD units. When a drug is selected, the generic name, brand name, and NDC number of the drug available in the RCD unit automatically appears in the window, along with the quantity of doses in each bottle. At this time, the operator is afforded an opportunity to select a generic substitution 506, as opposed to a brand name drug. A generic substitution generally saves money for the patient and tends to be a more current formula for the drug. Label data to be printed upon dispensing is automatically updated by the software to include the generic drug information. In addition, the software automatically maintains an inventory and keeps track of the drugs which have been dispensed and assures a first-in-first-out inventory process. This provides a round-robin dispensing system so that drugs are continually circulated and therefore, expiration dates will pass less frequently. In addition, this system averages out solenoid use for each column in the cabinet such that one column does not wear more quickly than other columns in the cabinet. The drug window 323C also requires the operator to select an ICD-9 disease code from a pop-down menu 507. The ICD-9 code is an industry standard code number for a variety of ailments known to physicians.

Figure 14E:
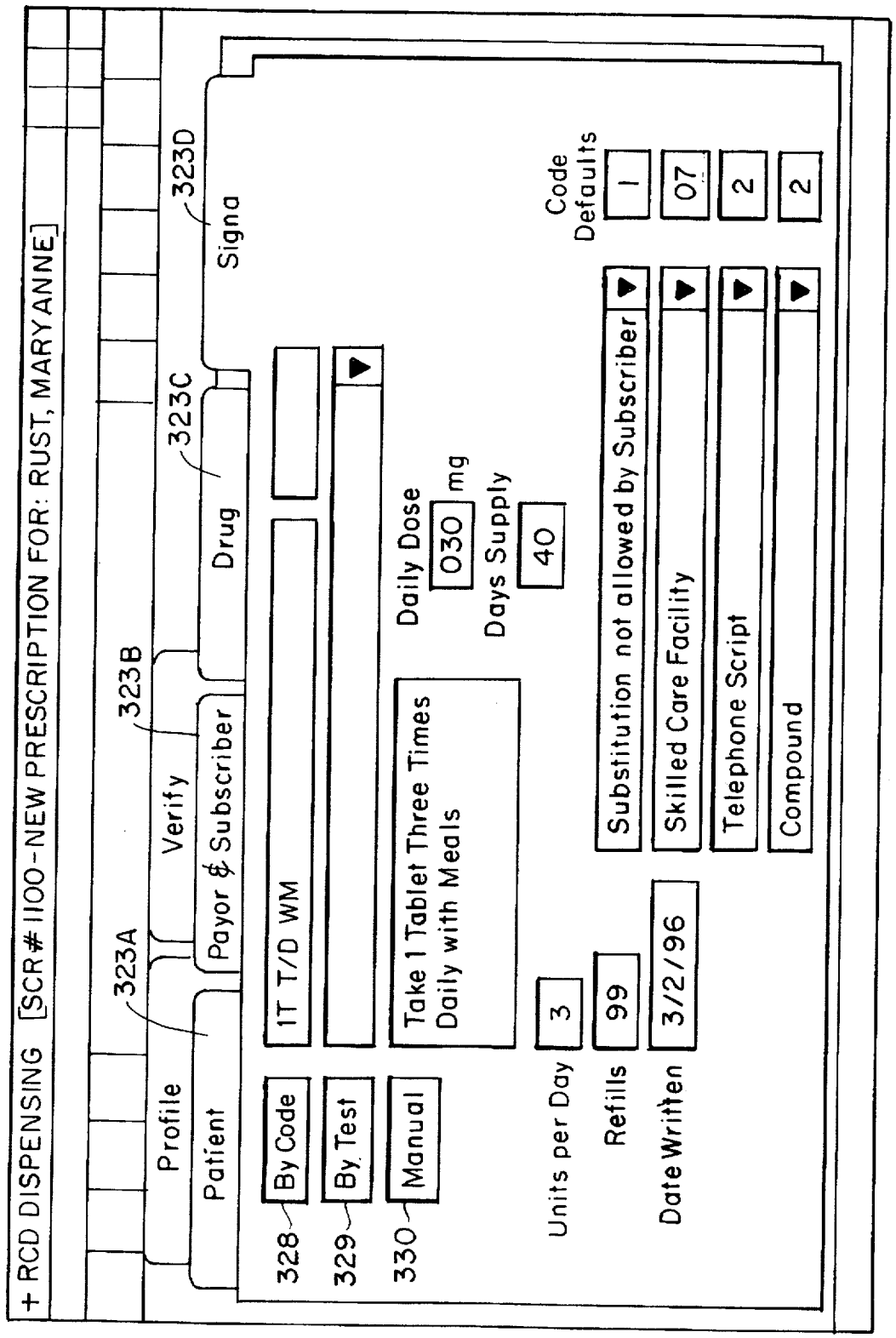
Figure 14F:
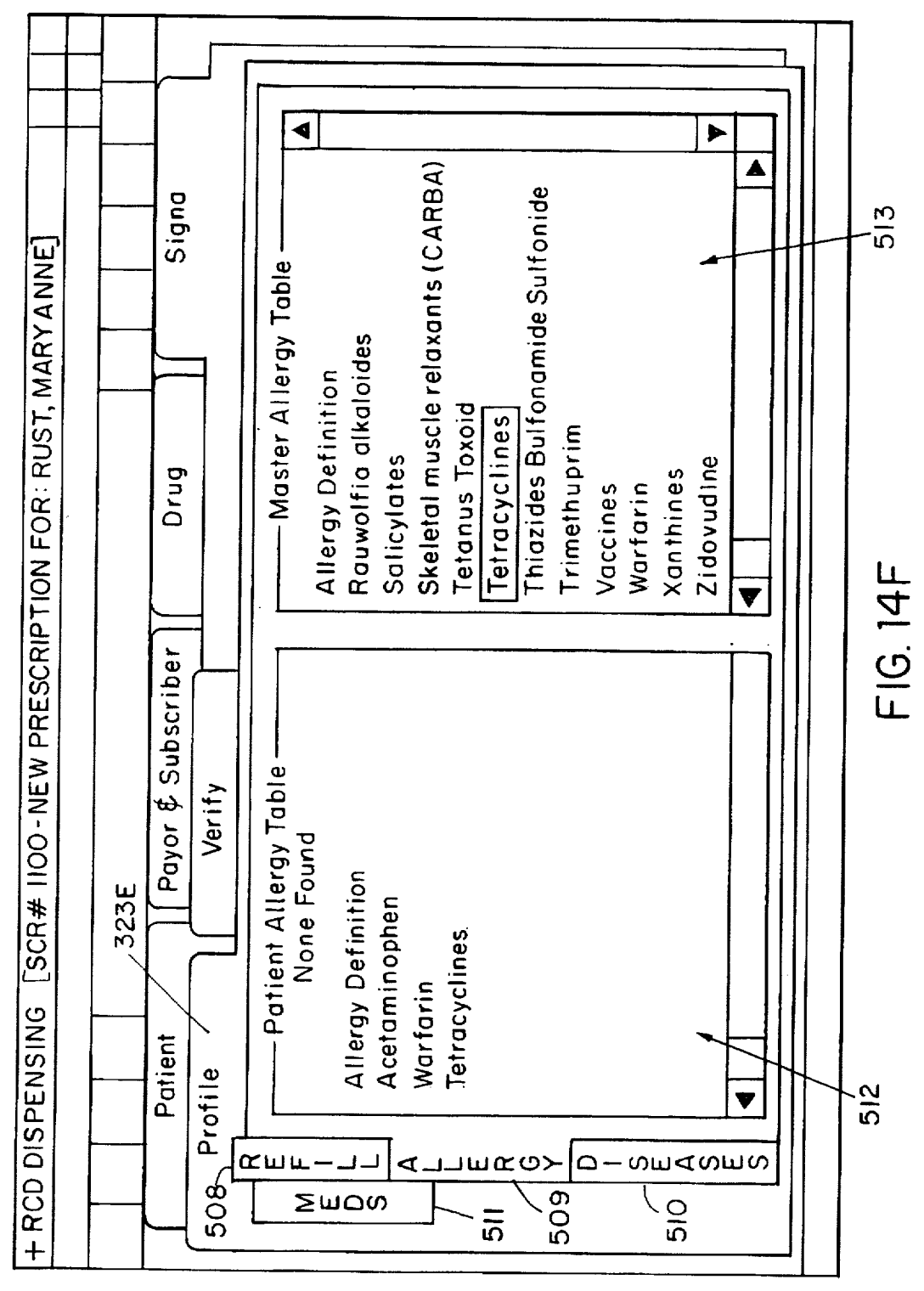
Figure 14G:
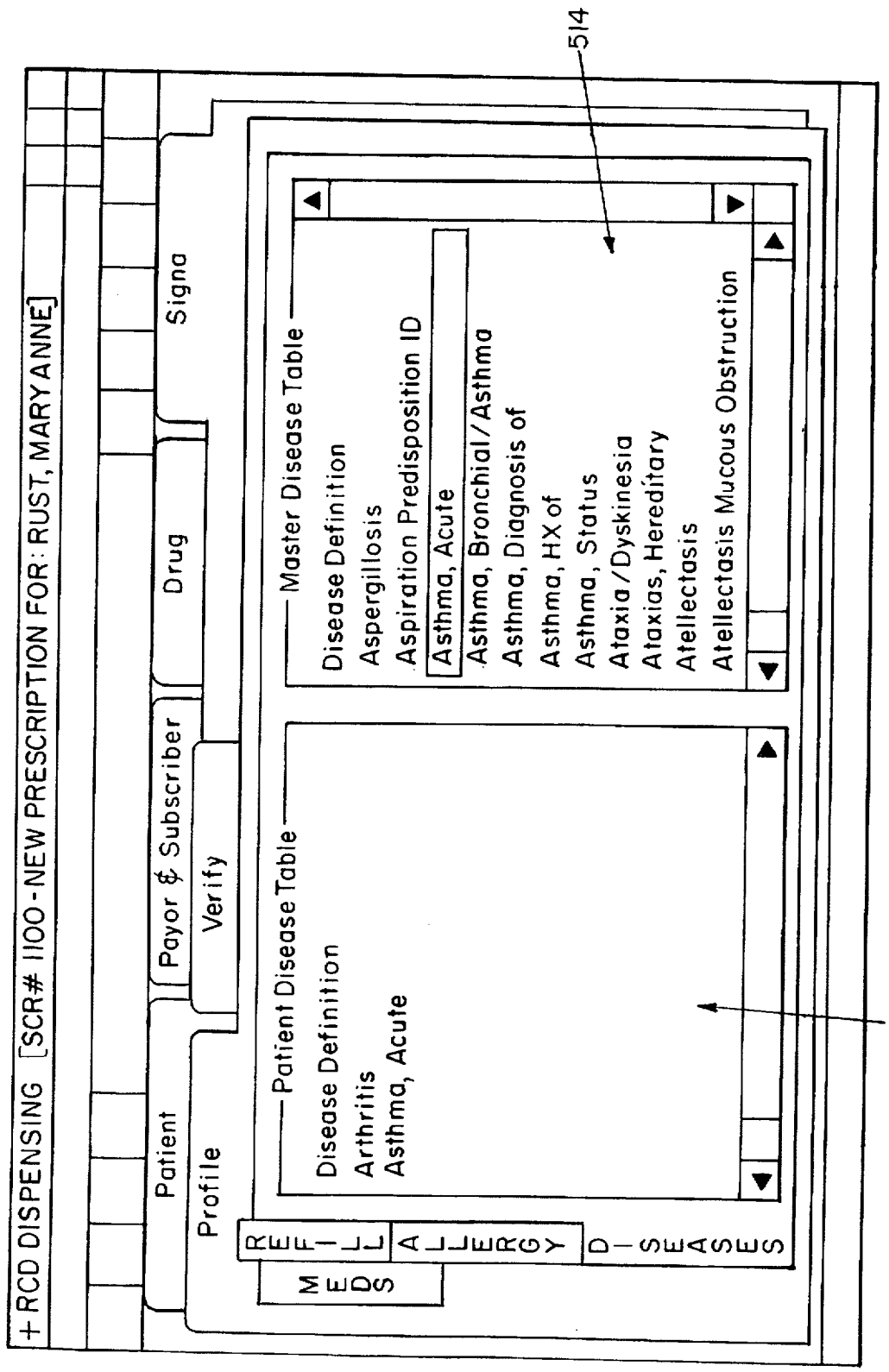

Returning to FIG. 13C, upon entering the required data in the patient 323A, payor and prescriber 232B and drug 323C windows, the operator selects the signa window 323D. In the signa selection task shown in FIG. 13D, corresponding to window FIG. 14E, the operator is prompted to enter a signa by code 328, by text look up, or manually 330. Signa codes are industry standard acronyms or codes used by pharmacists for providing instructions to the patient. If the operator enters a code 328, then the software determines whether the code is in the database 331 and whether it has been used before 332 in the system. If not, the computer is instructed to learn the new code 333 by adding it to the database 334. In addition, the computer questions whether the signa dosage amount is correct for the new signa, as shown in FIG. 14S. The newly learned code is then available to the non-technical user via the Signa by Text option 329. In this way, the commonly-used Signa combinations of a facility (i.e. regimen) are learned and more readily available. The properties of the signa code include 335 include the number of units per day, the day's supply, the daily dosage, and the refill date. These properties automatically determined by the software after the operator enters the signacode. Following this, the software returns to the point where the signa selection was called (see FIG. 13C).

Figure 14H:
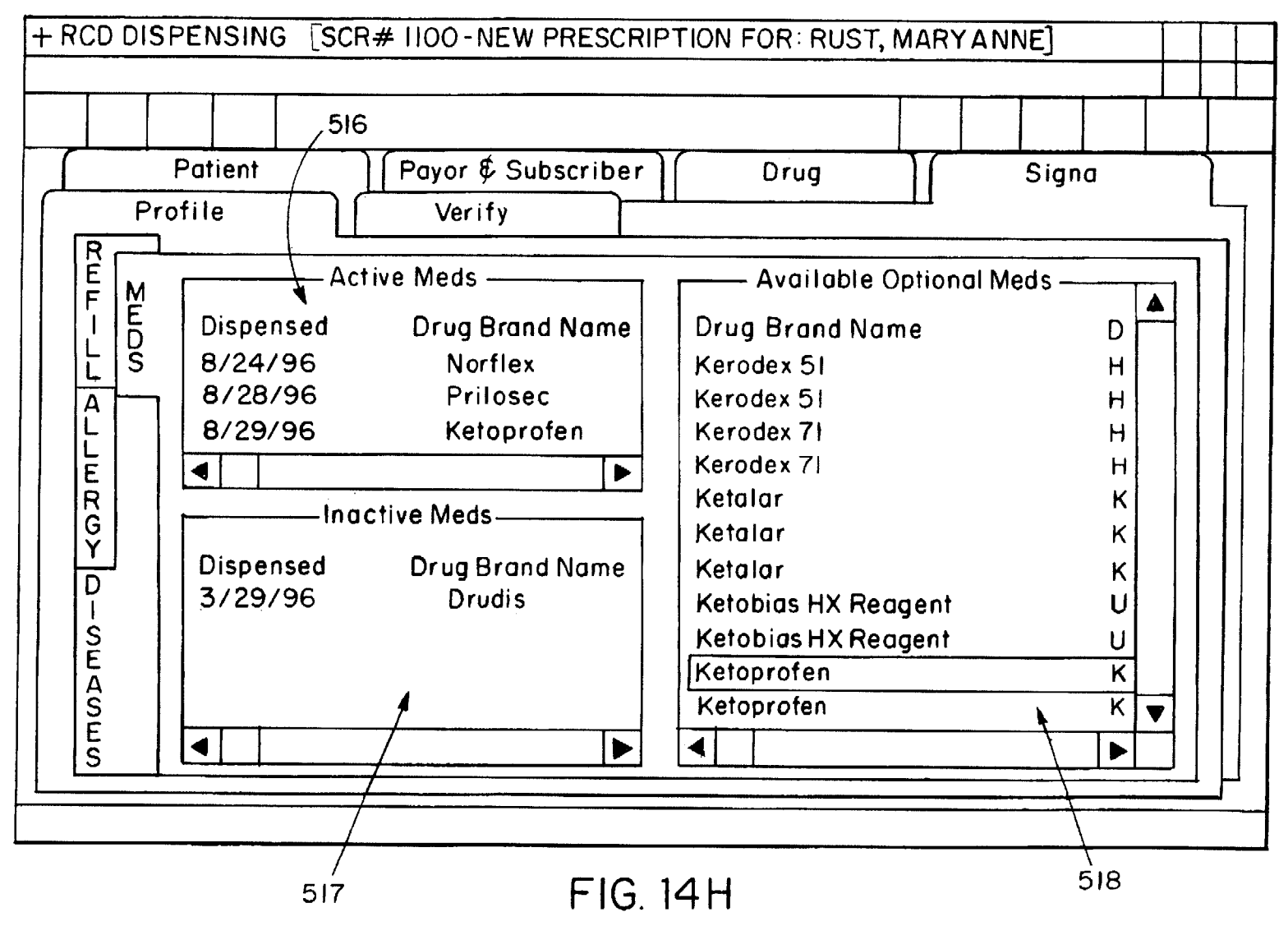

In the profile window 323E shown in FIG. 14F, a menu of sub-files are available to the operator for selecting various patient medical data including refill information 508, allergy information 509, disease information 510, and medication history 511. In the allergy window 509 shown in FIG. 14F, a patient allergy table 512 includes a list of known allergies for the patient. The patient allergies 512 are selected from a master allergy table 513 which includes all known pharmaceutical allergies. The operator scrolls through the master allergy list and selects the appropriate allergy. Using the drag-and-drop method, the allergy is copied from the master allergy table to the patient allergy table 512. The allergy information is used during the drug utilization review (DUR) to determine if there is a conflict between the patient's allergy history and the prescribed pharmaceutical or any pharmaceutical in the patent profile. In FIG. 14G, the patient's disease history is tracked in a similar manner. A disease history for the patient 515, is selected from a master disease table 514. In FIG. 14H, a medication history for the patient is tracked. The data tracked includes active medications 516 and inactive medications 517, including the date that the medication was dispensed, the brand name, and source of the pharmaceutical. Again, the tracked medications 516,517 are selected from a master medication window 518. The data includes the National Drug Code (NDC) for all prescriptions.

In the verify window 323F shown in FIG. 14K, the operator is given an opportunity to view all relevant prescription data. The data includes a synopsis of the patient information, payor, prescriber, ICD-9, drug, signa, and adjudication information. At this point 325 (see FIG. 13C), the software verifies that all relevant data has been captured. If it has not, the operator is prompted to enter those portions of the data which are missing. Upon verification, the continue button 519 is enabled. This is indicated by darkening of the letters which spell out the word "continue" and by the button 519 flashing when ready. If any information is missing, the computer directs the operator to the appropriate window for entering the missing information.

When the continue button 519 (see FIG. 14K) is selected by the user 327 (DUR), the software performs a drug utilization review 337 as shown in FIG. 13E. During a drug utilization review, the software analyzes the patient profile 336 compiled by the operator and performs a plurality of tests 337 to check for drug conflicts. The tests include: drug allergy, drug disease, drug interaction, dose check, duplicate therapy, drug food, pediatrics, geriatrics, pregnancy, lactation, disease additive, drug additive, drug induced, polypharmacy, side effects, and other standard DUR tests. Note that this process need not be sequential as shown in FIG. 14K. Threads may be used to obtain simultaneous occurrences of each test. In this manner, the patient profile can be simultaneously tested in the DUR to arrive at results faster.

Figure 14I:
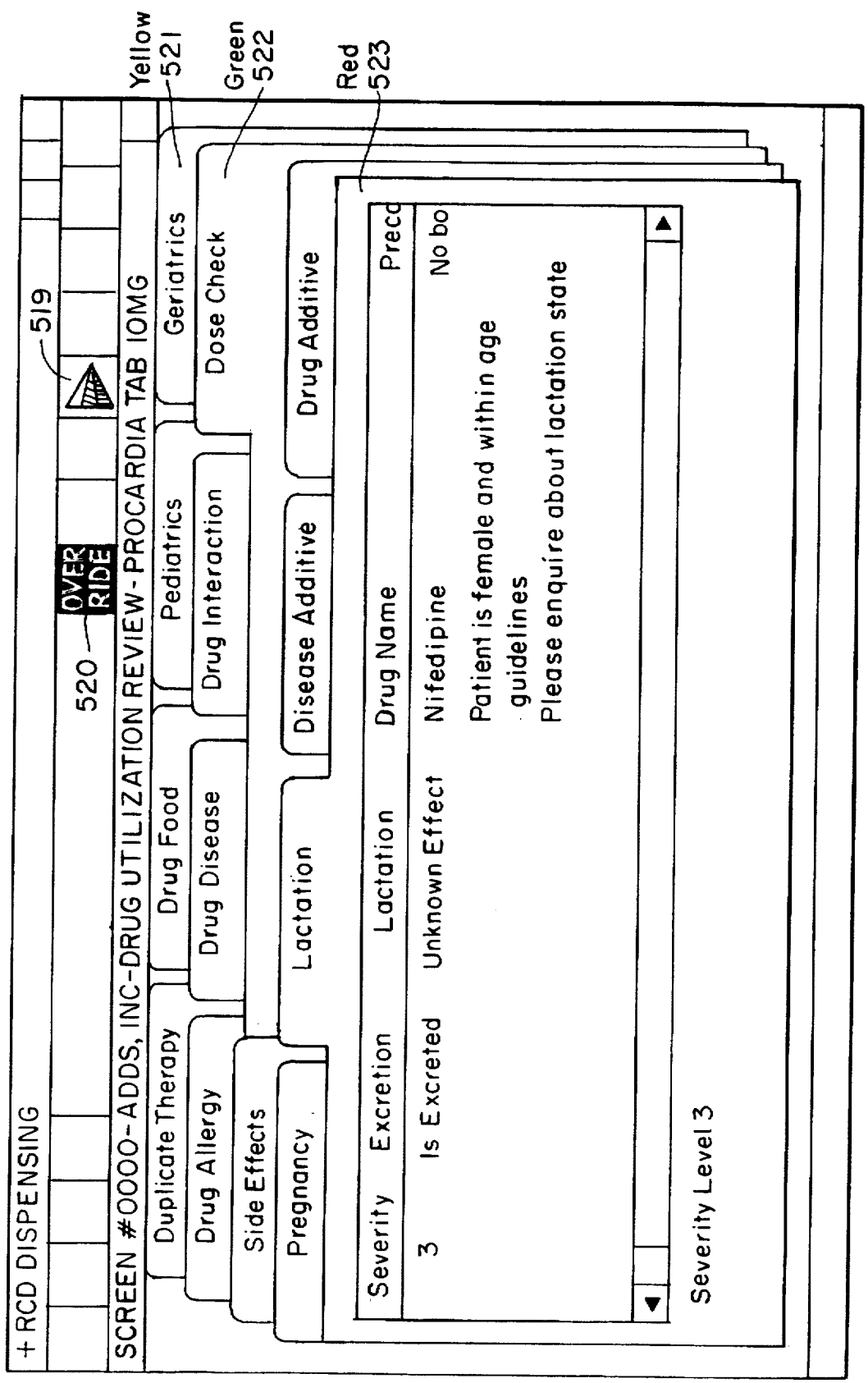
Figure 14J:
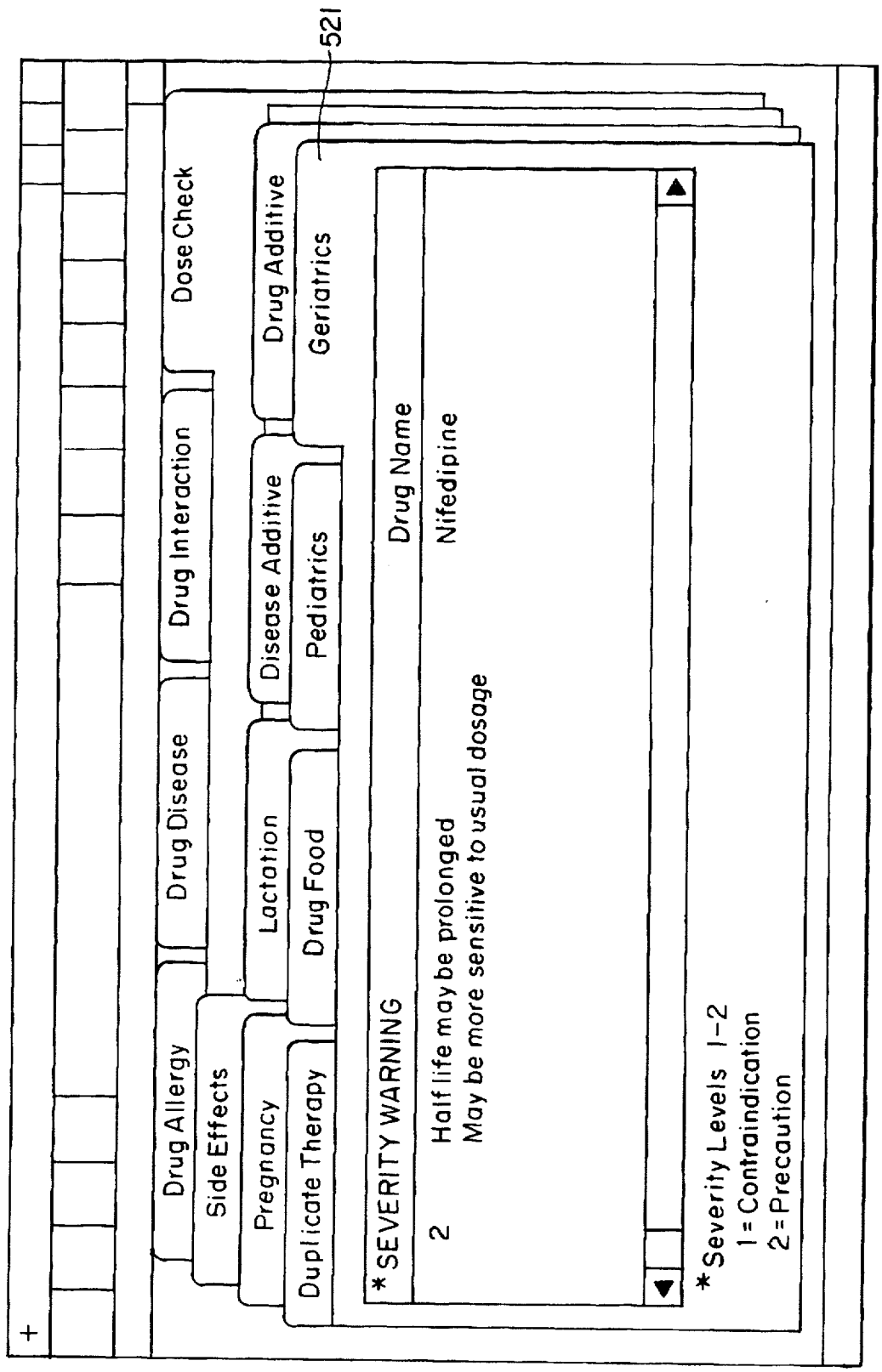

With reference to FIG. 13F, after a DUR test is completed, the user is provided with a drug utilization review window, as shown in FIG. 14I including a menu of tabs representing the various tests conducted. The DUR results are displayed as a series of tabbed folders of various colors as shown in FIG. 14I. Red folders 523, for example the "Lactation" folder of FIG. 14L, indicates a conflict with requires an override by the pharmacist. A red drug interaction field or has an additional feature of displaying a Drug Information Facts monograph for the user as shown in FIG. 14O. The user can additionally print the monograph for consultation with the responsible dispenser. In this manner on-line Drug Information is available for each drug interaction. A yellow folder 522, for example the "Duplicate Therapy" and "Drug Additive" folder, indicates that the tests should be checked by the pharmacist but does not require an override. A green folder, for example the "Geriatrics" folder 521, indicates that the tests passed without a conflict.

Returning to FIG. 13F, if the operator has selected a folder which is tabbed red, then the override button 520 is enabled 342 to allow the operator to override the flagged conflict. If no red tabs 339 are generated by the test, then the continue button 519 is enabled 340. When the continue button is selected 343 by the operator, the operator is prompted to enter a payment method 346. The payment method is selected in payor window 503 of FIG. 14C to determine which path to follow. If cash is selected, then a dispense subroutine is issued 377. If a third party payor is selected, then adjudication or payment confirmation takes place 347. The dispense and adjudication processes will be described below.

When the override command is selected 344, an override task 345 is called as shown in FIG. 13G. If the user is not authorized 349 to override the conflict, then a warning is displayed 358 and a remote or local pharmacist 359 is consulted. If a remote pharmacist is selected, the remote pharmacists key 361 is displayed and a connection is established 364 with encrypted data during the data exchange 367. Next, the computer performs an out dial to the remote pharmacist 368 who is given control of the dispensing process. As shown in FIG. 14V, during an override, the remote pharmacist will be required to enter a comment for dispensing to proceed.

Figure 14L:
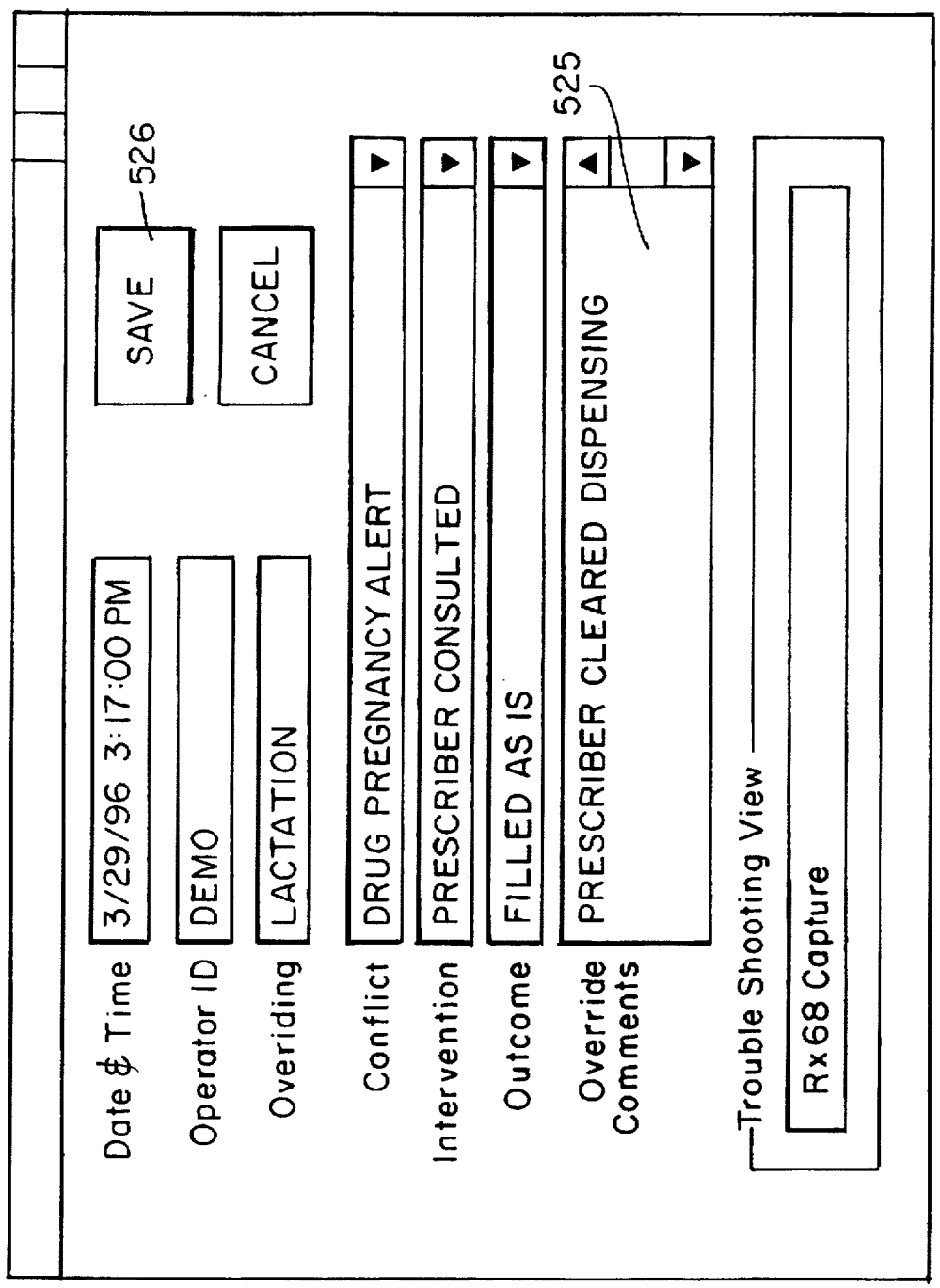
Figure 14M:
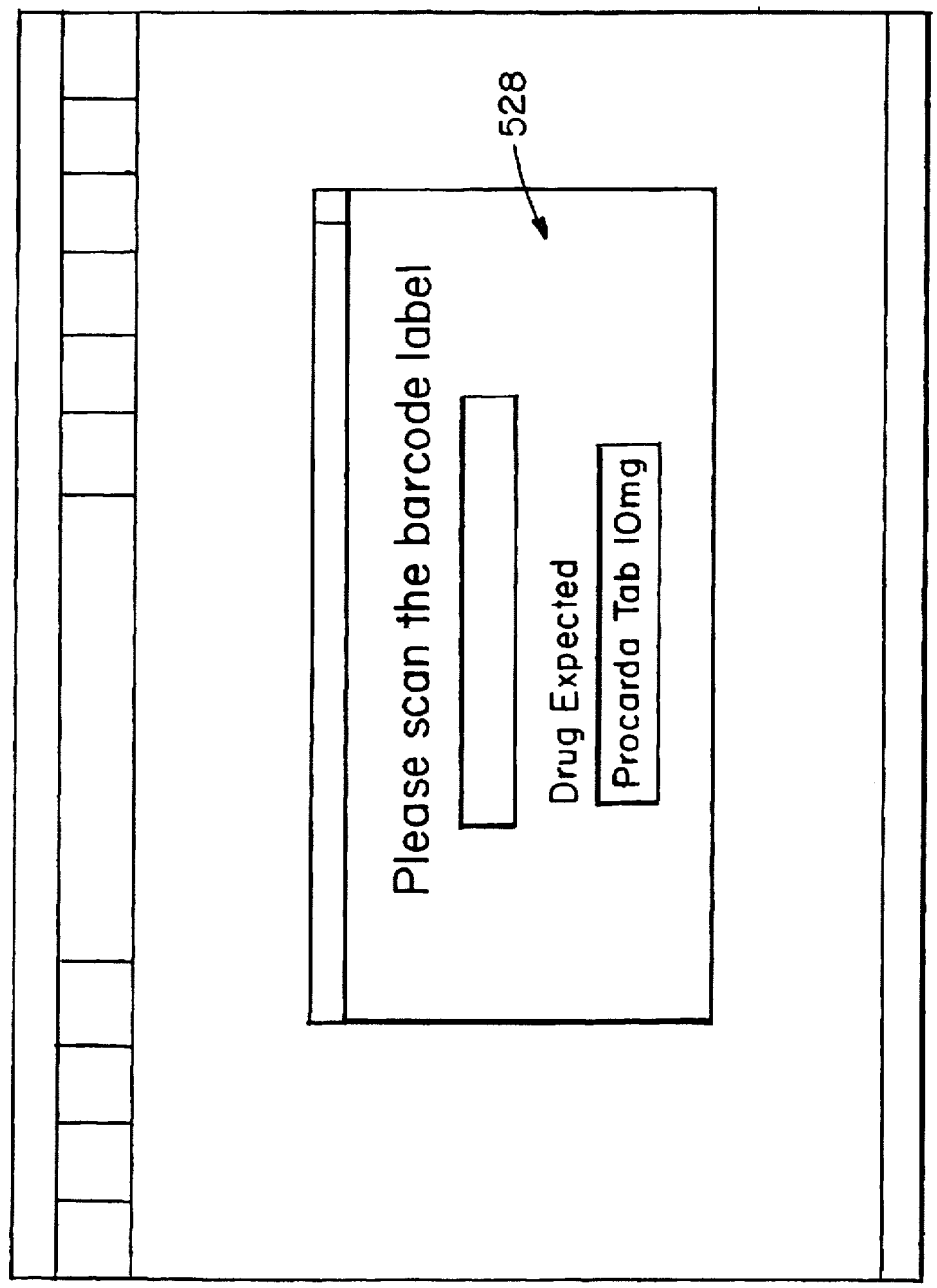
Figure 14N:
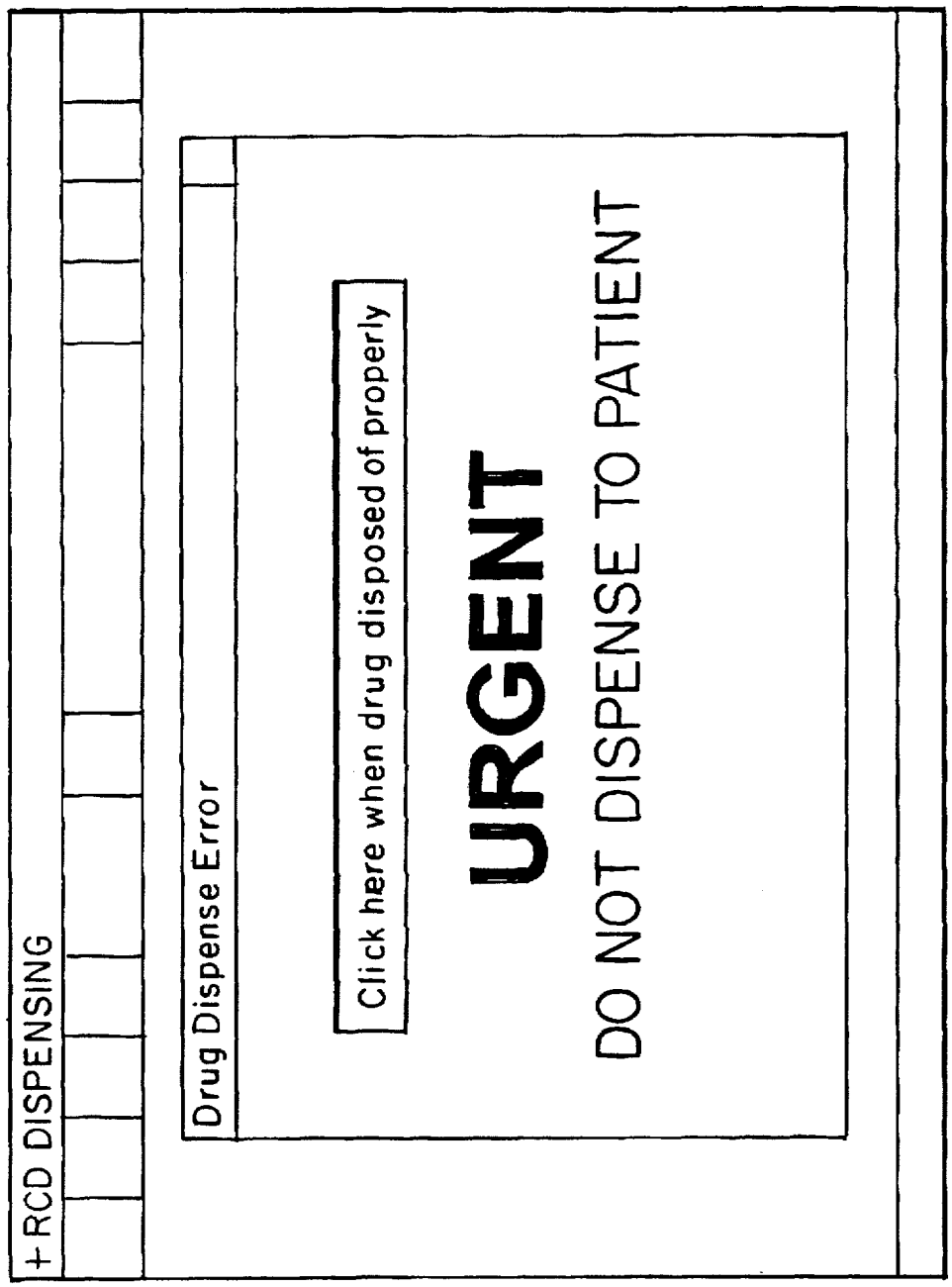
Figure 140:
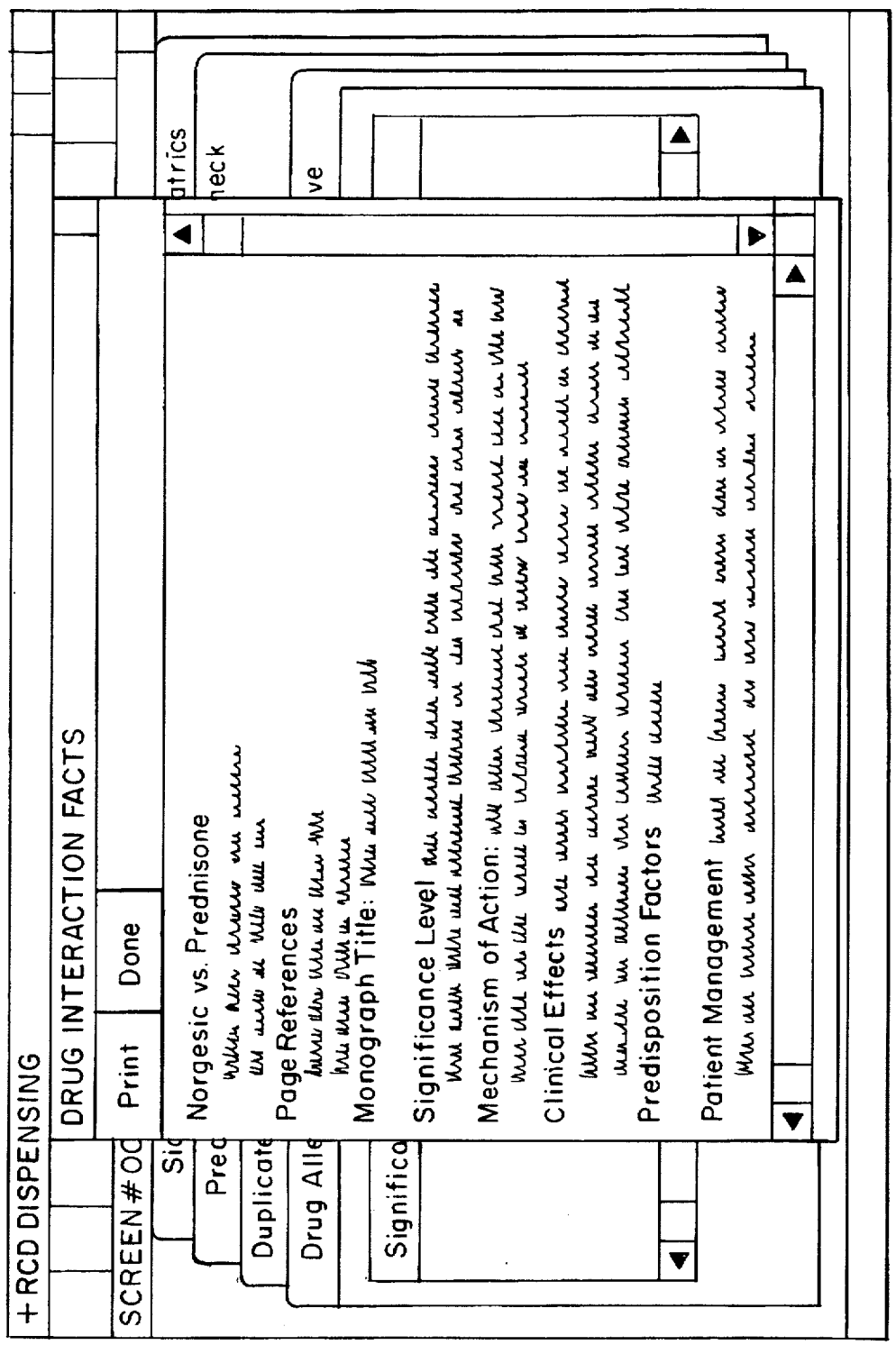

If a local pharmacist is selected 359, the authorized pharmacist is prompted for a password 360. If several invalid attempts are recorded 363, then the override is ended and the dispensing will not be allowed to take place. If the pharmacist password is authorized 362, or if the user is authorized 349, the an override window shown in FIG. 14L is presented to the operator. The override window identifies the operator and the conflict to be overridden 350. The user is prompted to enter a justification for the override and will not be allowed to leave this override screen without entering a comment in the comment window 525. After the appropriate data is entered, the data is captured to the database 355 by the operator clicking on the save button 526 and the program returns to the drug utilization review window shown in FIG. 14I. At this point, the previously red folder 523 will be given a new color, for example grey, to indicate that the conflict has been overridden.

Figure 14P:
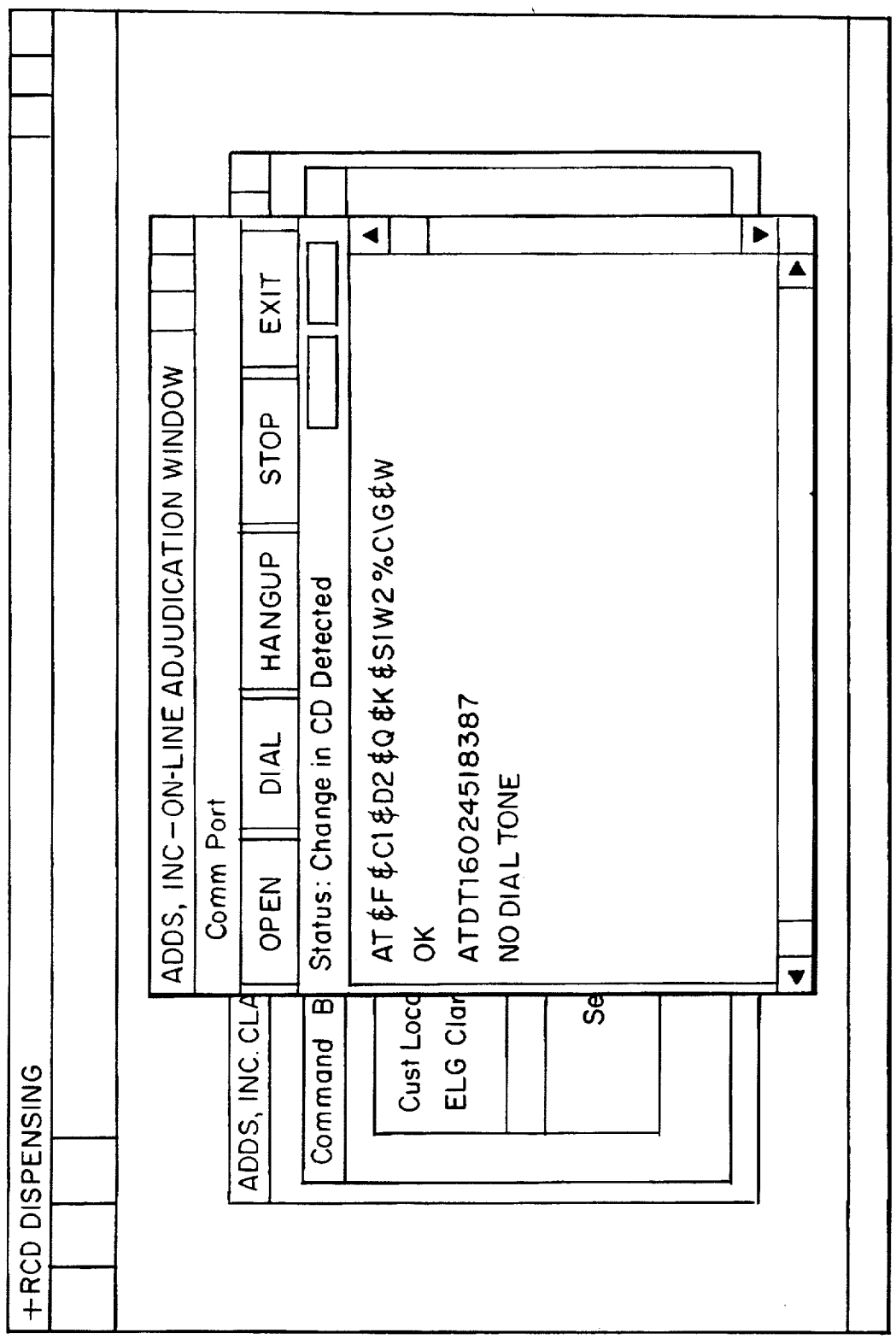
Figure 14Q:
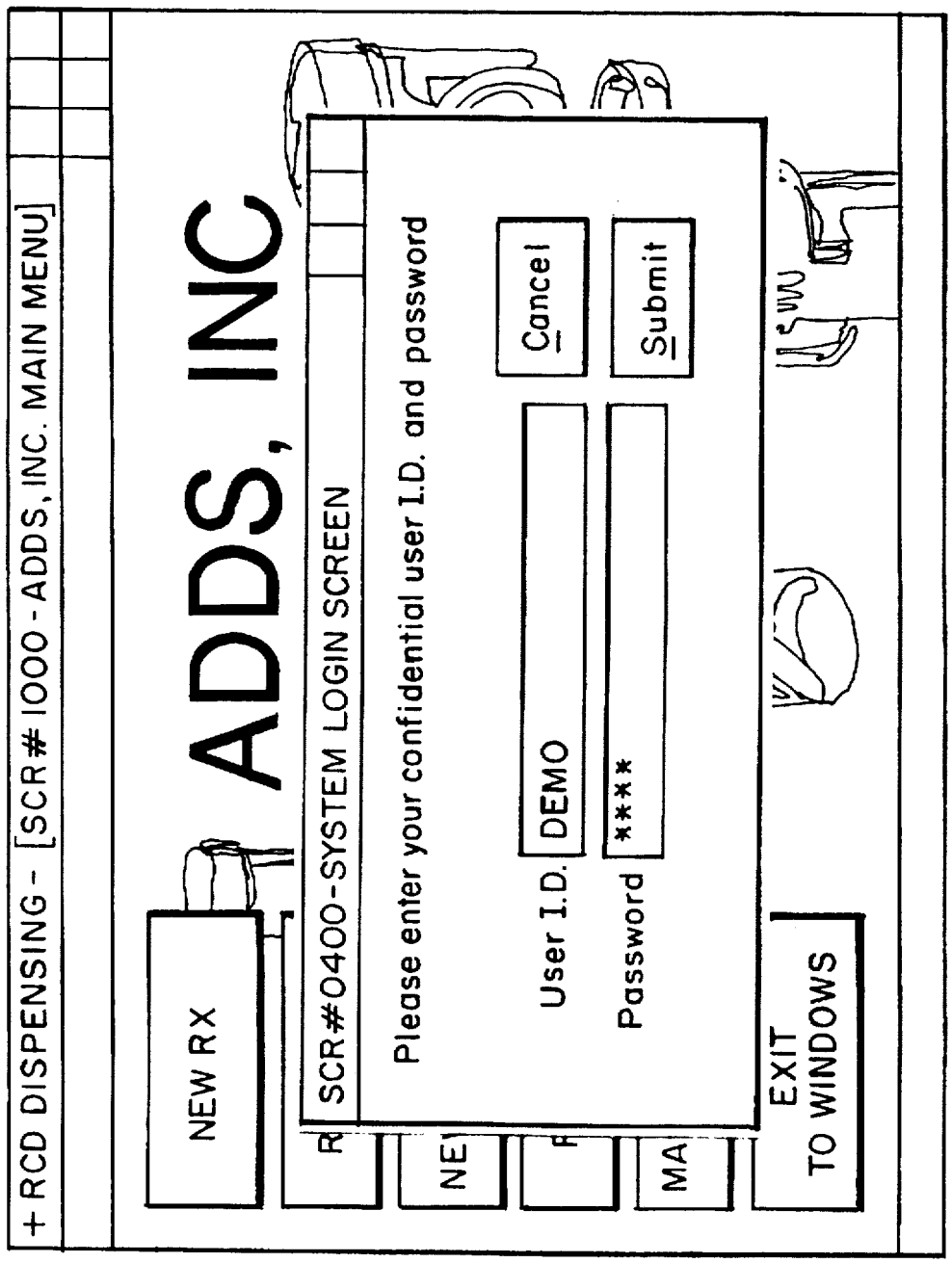

During an adjudication process shown in FIG. 13H, a data packet is initially prepared 369 and the modem is initialized 370 as shown in FIG. 14P. After initial handshaking 371, a determination is made whether transmission 372 is enabled. If transmission is not yet cleared, then the software waits for a predetermined period of time 373, and if a time out occurs 374, then the transaction is saved to disk for later use 376 so that the data does not have to be reentered and the pharmaceutical is dispensed 377. If transmission has been cleared 372, then data is transmitted 375 and the process waits for a response 378. If after a predetermined period of time 379, the software determines that it has waited too long 380, then the transaction is saved to the disk for later use 381 and the pharmaceutical is dispensed.

When a response is received 378, the returned data packet is parsed 383 as shown in FIG. 13I. If the payor has not authorized the transaction 384, then a rejection is displayed on the monitor 393 and the operator is queried to cancel 388, save the transaction for later 389, or resend the transaction 390 as shown in FIG. 14V. If cancel 388 is chosen, then the program ends and returns to the jump screen 500 shown in FIG. 14A. If "save for later" 389 is selected, then the transaction is saved to the disk for later use 392 and a dispense command is ordered 377. If resend 390 is selected, then the operator is given an opportunity to modify the outbound data packet 391 and adjudication is initiated again. If the payor authorizes the transaction 384, then an approval is displayed on the monitor 385 and the operator is queried whether he accepts the approval 386. If so, and the operator has to respond to a payor DUR 387, then adjudication is performed again. Otherwise, a dispense task 377 is performed.

Figure 14R:
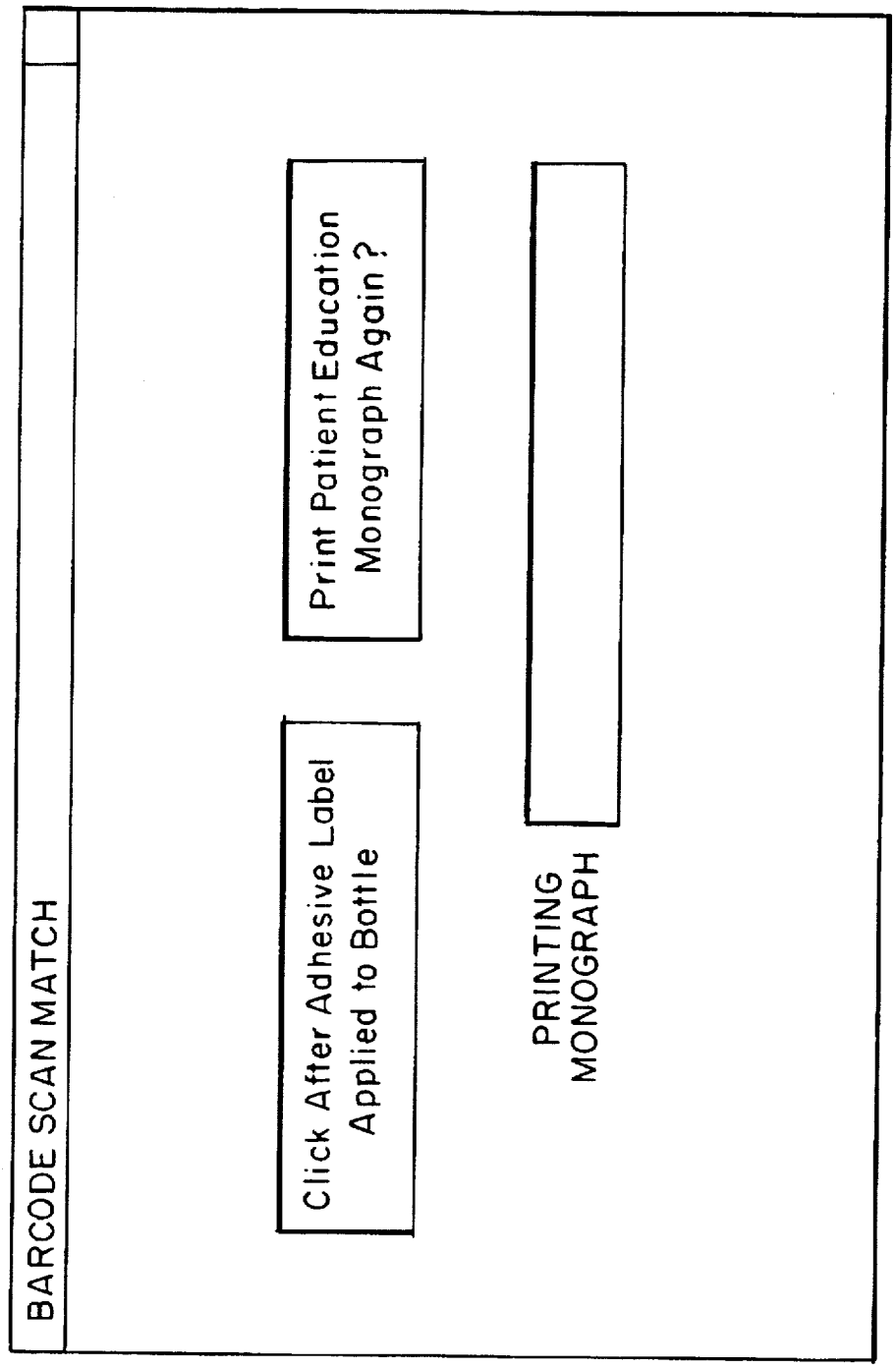
Figure 14S:
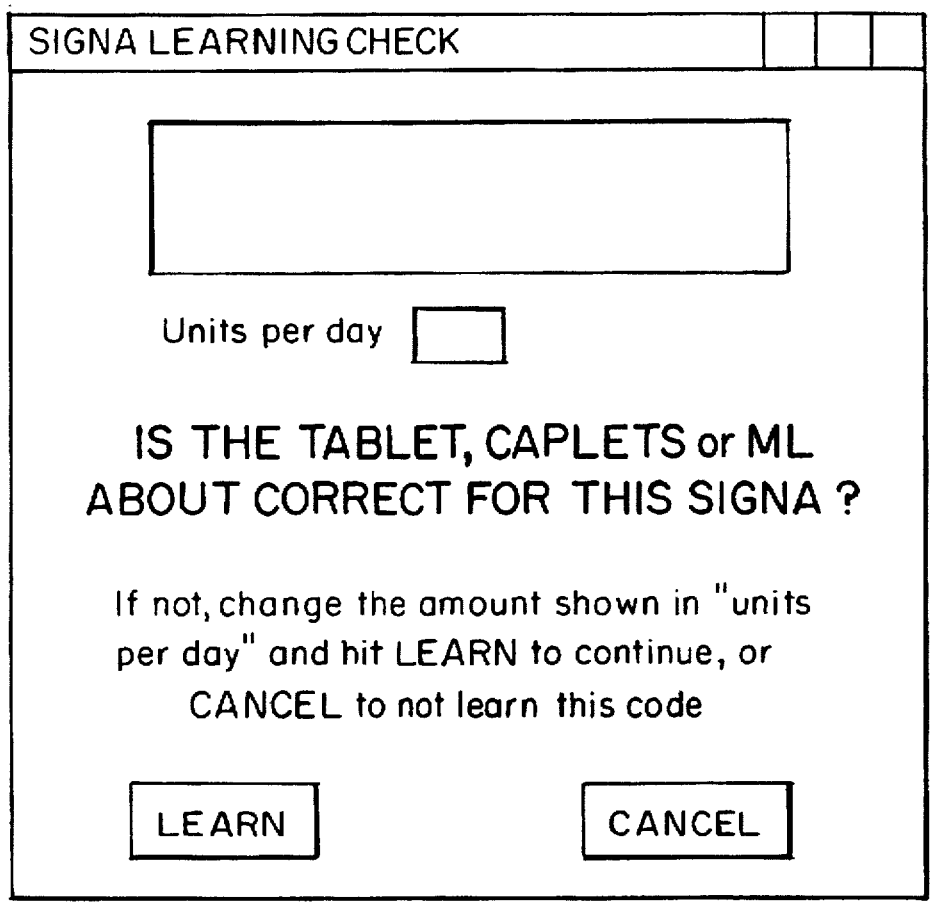

With reference to FIG. 13J, in a dispense task 377 the transaction is initially recorded in a transaction database 394 and a drop signal is sent to the dispenser 395. Upon receiving feedback from the dispenser 396, two barcoding safety options are possible 397. Under the first option, the barcode on the dispensed bottle is scanned 404 after a prompt by the software as shown in FIG. 14M. The prompt 528 requests the operator to scan the barcode label. After scanning, if the barcode matches that which the computer expects 405, then a patient monograph and bottle label is generated as shown in FIG. 15. The computer next prompts the user to report that the label has been applied to the bottle as shown in FIG. 14R.

The barcode applied to the dispensed package by the repackager may contain expiration date information which the computer automatically checks upon scanning the barcode. If the package has expired, the operator may be warned, and the label and monograph print function disabled. Also, the computer may check the package date against the ending date of the prescription period and disable the print function or otherwise warn the operator if this test fails.

Alternatively, if the second barcoding safety option is selected 397, then the printout is generated initially 398 and labels and safety barcodes from the printout are adhered to the bottle 399. The repackager barcode on the bottle and a prescription generated barcode are optically read or scanned 400 and the computer electronically compares the two codes to determine if they match 401.

Returning to FIG. 13J, if the bar codes fail to match 402, 403, then all data responsible for generating the error is captured 417 as shown in FIG. 13L and a warning is issued to the operator that the pharmaceutical or other item is not cleared for dispensing 418. Potential corrective measures are displayed 419, and the operator is given the option to lock the column generating the error 420. If so, the operator instructs the computer to lock the column 421. The server is automatically notified 422 by the computer via modem 423. After the server acknowledges receipt of the error 424, the program returns to the point where the dispense task was called.

Figure 14T:
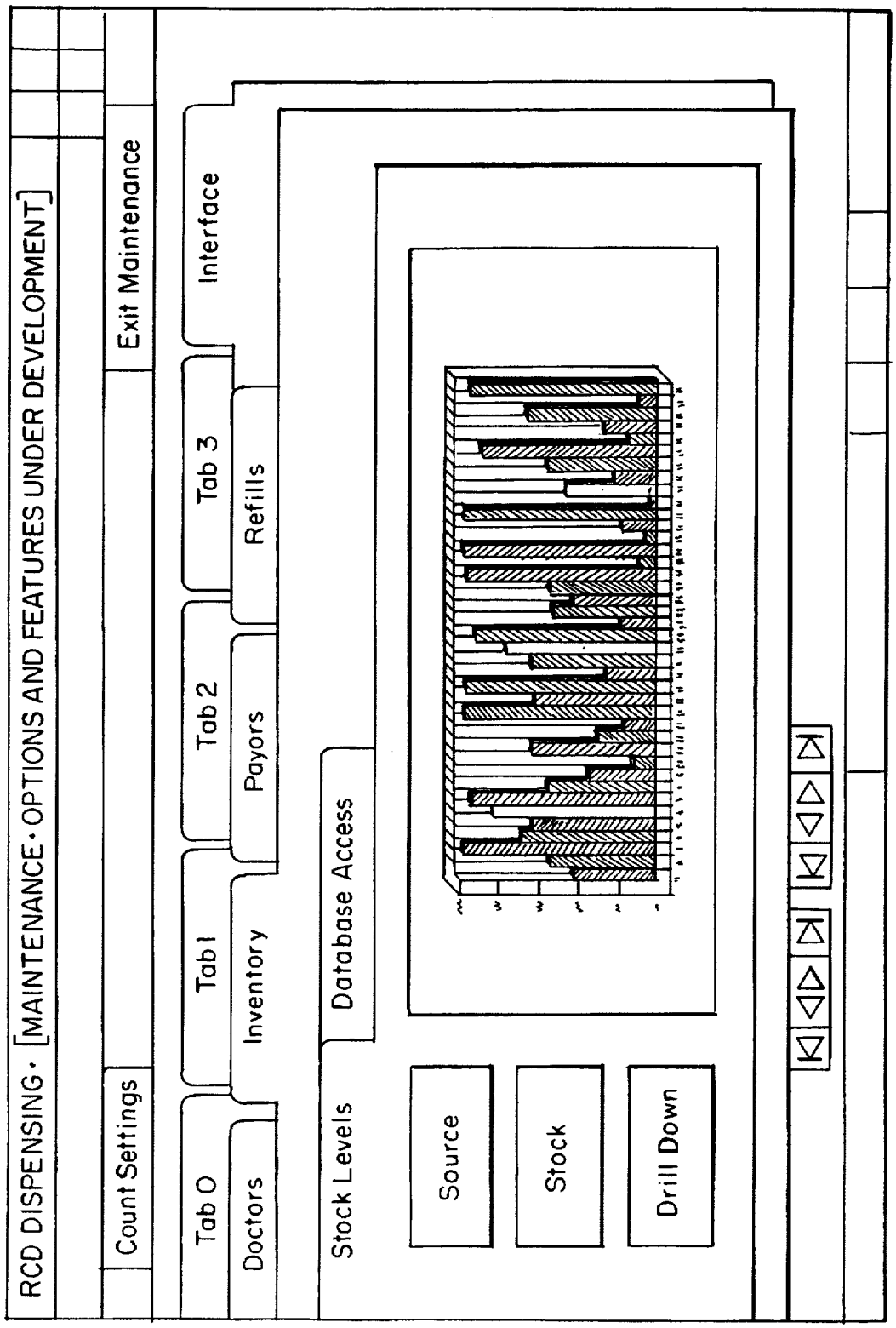
Figure 14U:
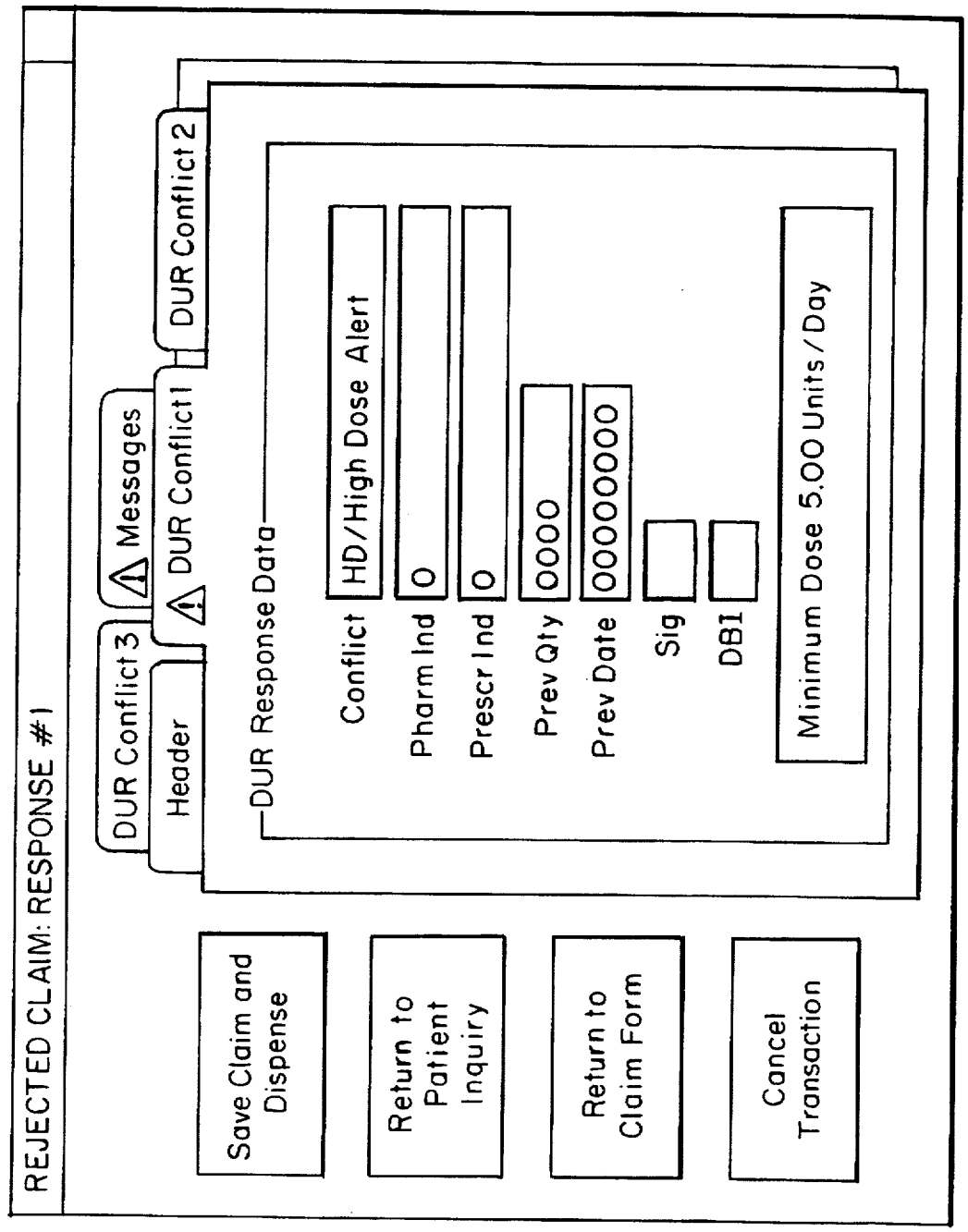

With reference to FIG. 13K, if a proper dispensing has occurred, then the transaction is recorded to the data base 407, and the computer determines whether inventory is at or below a predetermined restock value 408. If the inventory is at an appropriate value, the program returns to where the dispense task was called. Otherwise, an encryption program is activated 409 and an outdial to the server headquarters is performed 410 via modem 411. If the server acknowledges 412, then the files are marked as sent 413 and the software returns to the point where the dispense task was called. If the server fails to acknowledge within a limited number of attempts 414, then the operator is warned 415 that a communication problem exists and a command to start a timer for periodic low-inventory-dial-outs or "LIDOS" is initiated 416. A LIDO is a parallel background process for calling the distribution headquarter to replenish inventory. Following this, the computer returns to the point where the dispense task was called. In addition to the automated inventory processes described above, an operator may at any time monitor inventory in an RCD unit by selecting the "inventory" option shown in FIG. 14T. This image shows the number of bottles in each RCD bin or column.

During an override procedure shown in FIG. 13G, if a connection to a remote pharmacist 364 is established, at the remote pharmacist workstation as shown in FIG. 13M, the data received is decrypted 428, and the computer determines whether a share or package exchange 427 is occurring. In the case of a share exchange, the remote pharmacist assumes control of the system 429 and a remote pharmacist password is generated 426. In the case of a packet exchange 427, the data is displayed 425, and the remote pharmacist password is generated 426.

FIG. 13N is a flow diagram representing remote pharmacist password generation 426. Initially, a display key is transmitted from the remote system 431. The key is entered into the local program 432 and the local program decodes the key and generates a counter key 433. This counter-key is used as the remote pharmacists password 434. At this point, the program returns to the point where the remote pharmacist password generation task 426 was called.

With reference to FIG. 13O, if the refill option 310 is selected at jump screen 500 shown in FIG. 14A, then all relevant data should have already been entered into the database. At this point, the patient's name is selected 435 and a refill is selected for the patient 436. After a payment method is selected 437, a drug utilization review is performed, along with adjudication and dispensing as described above.

FIG. 13P is a flow diagram representing tasks performed when the new patient 311 option is selected at the jump screen. In this task, new patient demographics 438, allergy profile 439, disease profile 440, and medical profiles 441 are entered for the new patient. After this task is performed, control is returned to the jump screen of FIG. 14A.

With reference to FIG. 13Q, if the reports option 312 is selected at the jump screen, a list of available reports are presented to the operator. The operator is given a choice to print or preview a report 443. If the preview option is selected, then the report is generated on the monitor 444. After viewing the report 444, the operator is given a choice whether to print the report 445, and if so, the report is sent to the printer 446.

Figure 16:
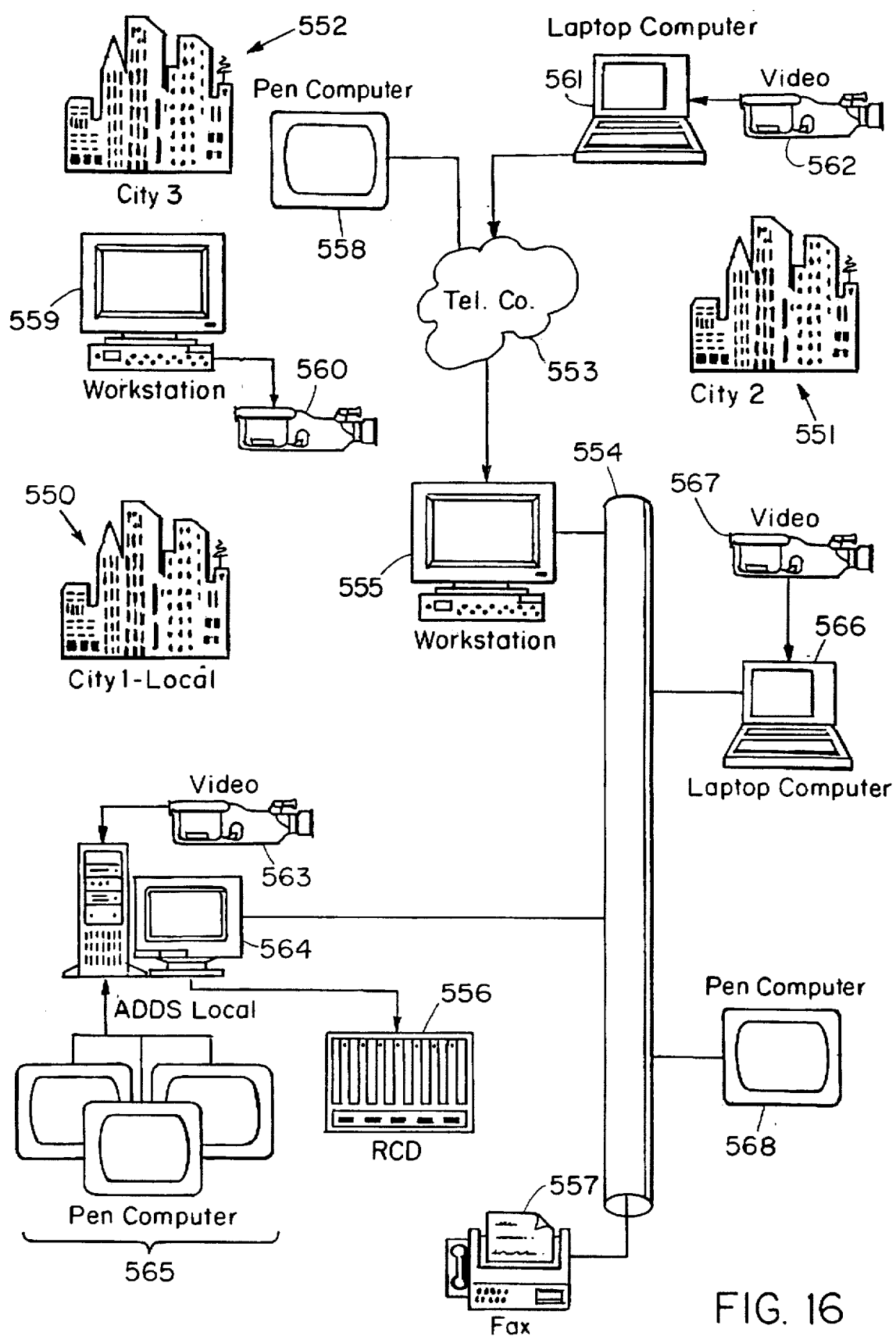
FIG. 16 is a block diagram representing a variety of remote drug dispensing configurations in accordance with the present invention.

FIG. 16 is a schematic diagram representing a typical remote drug dispensing configuration in accordance with the present invention. System access locations are shown in a first city 550, second city 551, and a third city 552. Pharmacists and physicians in the second 551 and third 552 cities communicate with physicians, pharmacists, and technicians in the first city 550 via telephone connections 553, for example, a telephone modem, or an ISDN connection. A gateway computer 555 in the first city 550 operates as a server to receive and transmit messages on the telephone lines 553. Access stations in the first city 550 are interconnected via an intranet 554 otherwise known as an ethernet or local area network (LAN). The LAN may be located in a hospital, an HMO, or a pharmacy. Hardware connected to the LAN 554 includes the gateway workstation 555, a laptop computer 566 with video teleconferencing capabilities 567, a pen computer 568, a facsimile 557, and an RCD host computer 564 operating an RCD unit 556. The RCD host computer 564 may also have video teleconferencing hardware 563 and a plurality of pen computers 565 connected thereto.

When a patient approaches a technician at an RCD unit 556, the technician initiates the dispensing process by entering relevant patent data into the RCT host computer 564. If the dispensing process requires the expertise of a pharmacists, then the technician at the host computer 564 issues a request to an available pharmacist operating the pen computer 568, laptop computer 566, or workstation 555 within the building in the first city 550, or may request the services of a pharmacist operating an RPH workstation 559 in the third city 552 or a pharmacist at the laptop computer 561 in the second city 551. Relevant data is exchanged and video teleconferencing is enabled between the technician and the pharmacist or prescribing physician if appropriate. Hand written scripts may be transferred to and from the first city 550 via facsimile 557. The facsimile image may be downloaded into the host computer 564 and stored with relevant patient data.

Figure 17:
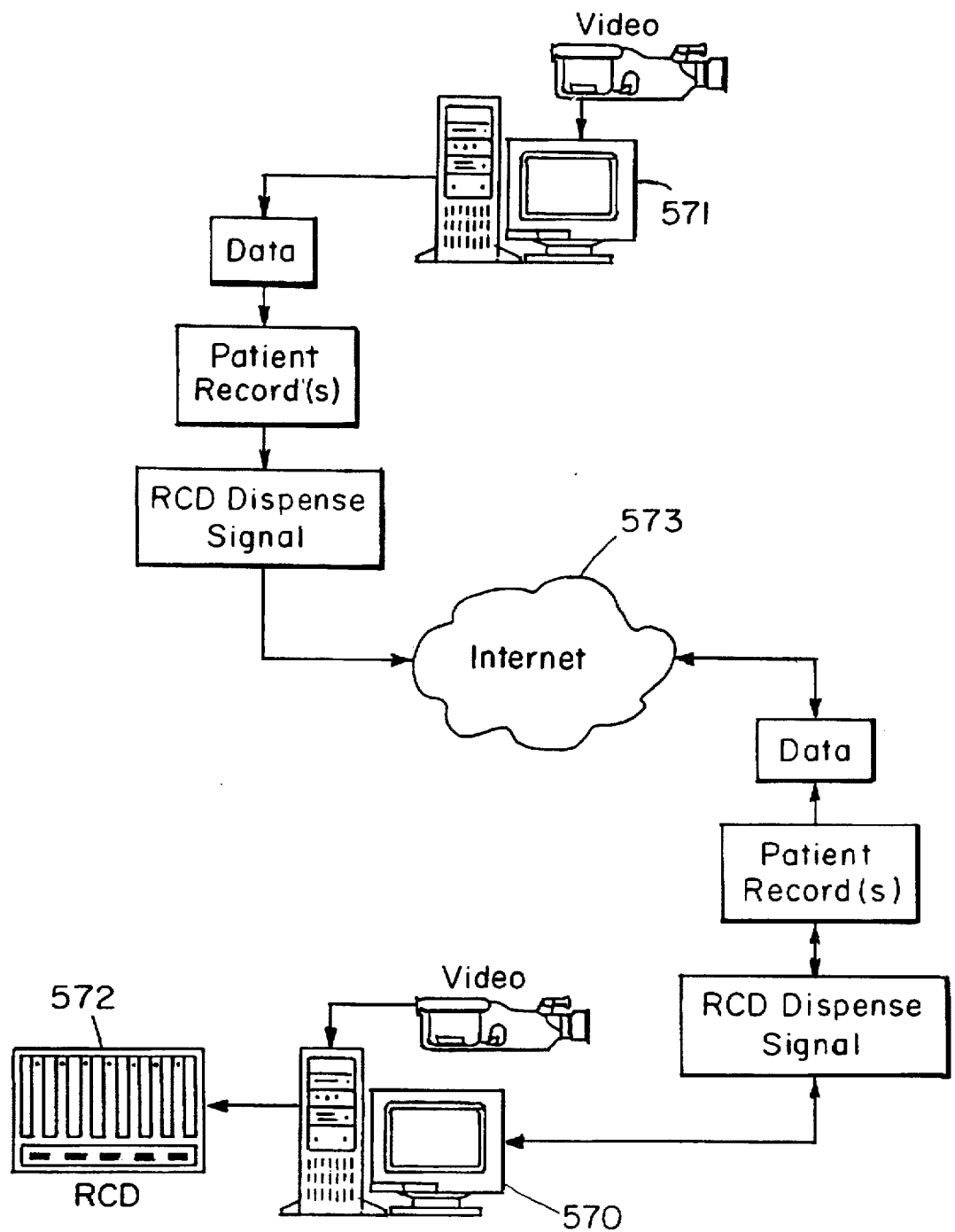
FIG. 17 is a schematic block diagram representing the transfer of data between an RCD host computer and a remote RPH workstation in accordance with the present invention.

FIG. 17 is a schematic block diagram representing the transfer of data between an RCD host computer 570 and a remote RPH workstation 571. A technician at the host computer 570 receives a request for a prescription from a patient at the RCD unit 572. The technician prepares the relevant data including the patient record, the prescription to be dispensed, and the adjudication information. The data is packed, encrypted and transmitted over the internet 573 to the RPH workstation 571 operated by a registered pharmacist. The pharmacist receives the data, conducts the relevant tests and makes a determination regarding dispensing the pharmaceutical. A packet of data is prepared with the patient's records, data, and any comments, along with a signal to cause the RCD unit 572 to dispense. This data packet is transmitted over the internet 573 as an Email message or other data file to the host computer 570. The host computer 570 receives the message, unpacks the data, and dispenses the pharmaceutical automatically, in real time. In this manner, a pharmacist operating a remote workstation 571 causes the RCD unit 572 to dispense the pharmaceutical in real time. Alternatively, the dispense commands may be issued in a batch process, requiring the technician at the host computer 570 to issue the dispense command to the RCD unit. Scripts from the host computer 570 generated by the technician may also be transmitted to the pharmacist at the RPH workstation 571 in batch form.

Figure 18:
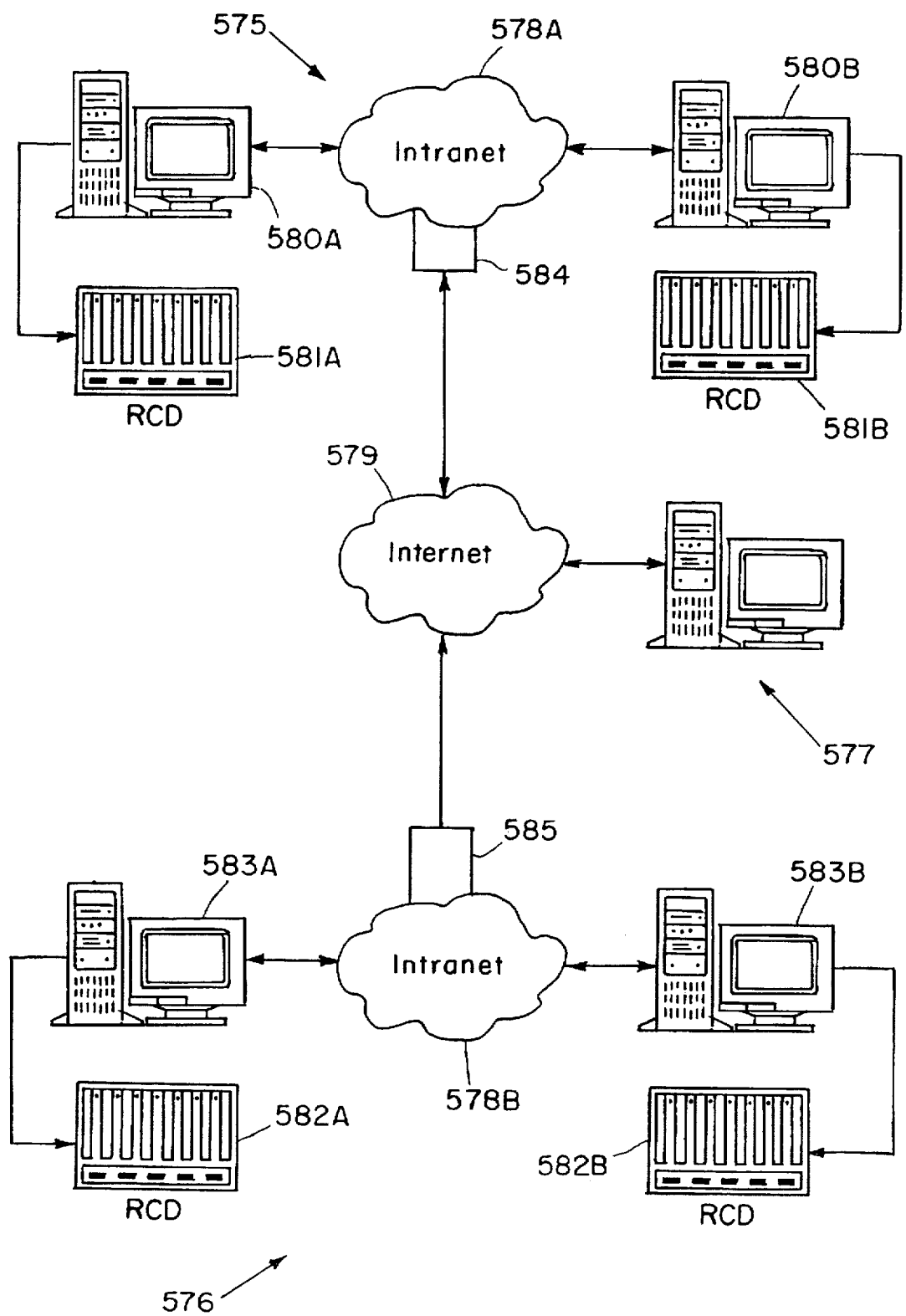
FIG. 18 is a schematic block diagram representing connectivity between RCD units at various sites in accordance with the present invention.

FIG. 18 is a schematic block diagram representing connectivity between RCD units at various sites. For example, a hospital site 575, may communicate with an HMO 576 via the internet 579. At the hospital site 575, two RCD units 581A, 581B are supported by two RCD host computers 580A, 580B respectively. The host computers communicate via intranet 578A, otherwise known an internal internet, or a LAN. A server 584 on the LAN 578A provides an interface between the LAN 578A and the internet 579. The RCD units 581A, 581B may serve two separate wards in the hospital. At the HMO office 576, a similar configuration employing two RCD units 582A, 582B hosted by host computers 583A, 583B are interconnected by a LAN 578B, and server 585. Distribution headquarters 577 also interfaces with the internet 579. In this manner, headquarters 577 can automatically keep track of stock levels, patient data, and other data warehousing functions.

Figure 19:
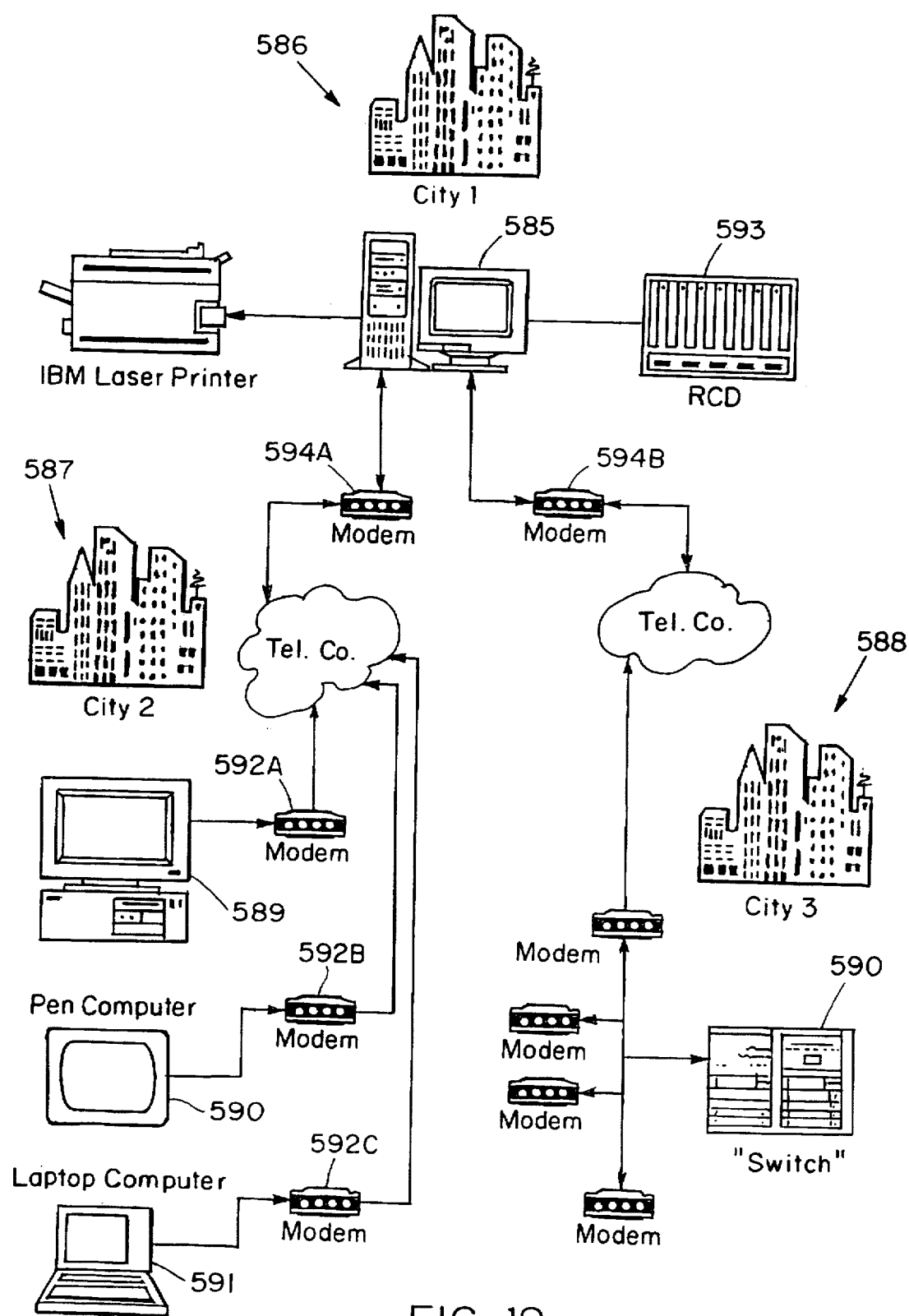
FIG. 19 is a schematic block diagram representing dual modem configuration in accordance with the present invention.

FIG. 19 is a schematic block diagram representing dual modem configuration. An RCD host computer 585 serving an RCD unit 593 in a first city 586 is configured to operate with a first and second modems 594A, 594B. Using the first modem 594A, the technician at the host computer 585 may solicit instructions from a pharmacist in a second city 587 operating a RPH workstation 589, a pen computer 590, or a laptop computer 591 each equipped with a modem 592A–C. A second modem 594B on the RCD host computer 585, allows for adjudication to take place with an adjudication switch 590 in a third city 588 while the link between the RPH workstation 589 and the RCD host computer 585 is maintained. In this manner, a pharmacist at a remote location in a second city 587 can access an RCD host computer 585 through a first modem 594A and perform adjudication between the RCD host computer 585 and an adjudication switch 590 in a third city 588 using the second modem 594B.

Alternatively, if the remote pharmacist at the RPH workstation 589 did not wish to remain online during adjudication, then the remote pharmacist could issue an adjudication batch command to be performed by the RCD host computer 585. After the batch command is issued, the link between the RPH workstation 589 and the host computer 585 is deactivated and the host computer performs adjudication. After adjudication is completed, the RCD host computer 585 reestablishes the link between the RCD host computer 585 and the RPH workstation 589 to inform the remote pharmacist that adjudication is completed. This batch process requires only a single modem at the RCD host computer 585 which is time-shared for script and adjudication processing.

While this invention has been particularly shown and described with references to preferred embodiments thereof, it will be understood by those skilled in the art that various changes in form and details may be made therein without departing from the spirit and scope of the invention as defined by the appended claims.

We claim:

1. A method for dispensing packages comprising:
   storing a plurality of coded packaged items in a housing;
   receiving request signals to dispense a package at a controller;
   generating dispense signals in response to the received request signals;
   displaying package information on a computer display;
   dispensing a package from the housing in response to the dispense signal;

delivering said dispensed pharmaceutical to a drop point with a ramp on the housing;

reading the code of a dispensed package with a code reader; and verifying that the requested package was dispensed.

2. The method of claim 1 wherein the step of dispensing further comprises dispensing a packaged pharmaceutical with a dual dispenser valve.

3. The method of claim 1 further comprising the step of printing a prescription label at a label printer for attaching to the dispensed package.

4. The method of claim 3 further comprising the step of printing a picture of a pharmaceutical pill on the label.

5. The method of claim 1 further comprising providing a plurality of multi-dose pills in each package.

6. The method of claim 1 further comprising providing each packaged item in a plastic bottle.

7. The method of claim 1 further comprising providing a fluid within each package.

8. The method of claim 1 further comprising providing a computer connected to the controller with a modem.

9. The method of claim 1 further comprising a method of loading packages in the housing comprising;

monitoring an amount of packages within the housing;

generating a reload signal;

opening the housing;

scanning packages with a bar code reader as the packages are loaded into the housing; and recording data in a memory regarding the loaded packages.

10. The method of claim 1 further comprising scanning the packages with a hand-held bar code reader.

11. The method of claim 1 further comprising monitoring the packages in a bin of the housing with a sensor.

12. The method of claim 1, further comprising printing a label having a second code, the label being attached to the dispensed package.

13. The method of claim 1 further comprising optically reading a first code on the dispensed package and optically reading a second code on a label attached to the dispensed package.

14. A method for dispensing a packaged item for medical treatment comprising:

storing a plurality of coded medical treatment packaged items in a housing;

dispensing a packaged item from the housing having a first code;

forming a second code;

optically reading the first code and the second code; and verifying the packaged item by electronically comparing the first code and the second code.

15. The method of claim 14 further comprising printing the second code on a label and attaching the label to the package.

16. The method of claim 14 further comprising displaying package information on a computer display and displaying an instruction not to deliver the package if the second code does not match the first code.

17. A method of dispensing packaged pharmaceuticals comprising:

storing a plurality of coded packaged pharmaceuticals in a housing;

displaying patient information on a computer display;

performing a plurality of required patient data entry operations; and automatically electronically enabling or disenabling a dispenser controller after completion of the patient data entry operations such that a package dispenser can dispense a coded package only upon receipt by the dispenser controller of an enabling command from the computer.

18. The method of claim 17 further comprising providing an override command such that a user can enable the dispenser control to dispense a package and recording an override command entry in a computer memory.

19. The method of claim 17 further comprising color encoding displayed patient data files on the display.

20. The method of claim 17 wherein the step of storing a plurality of coded packaged pharmaceuticals further comprises storing an encoded plurality of packaged pharmaceuticals in a bin, a plurality of bins being contained in the housing.

21. The method of claim 20 further comprising dispensing a packaged pharmaceutical from a bin in response to the enabling dispense signal.

22. The method of claim 20 further comprising dispensing a packaged pharmaceutical with a dual valve dispenser from a bin in response to the enabling dispense signal.

23. The method of claim 22 further comprising the step of reading the code of a dispensed package with a code reader; and verifying that the requested package was dispensed by comparison of the code read by the code reader to a reference code.

24. A method for dispensing packages and of loading packages in the housing comprising;

storing a plurality of coded packaged items in a housing;

receiving request signals to dispense a package at a controller;

generating dispense signals in response to the received request signals;

displaying package information on a computer display;

dispensing a package from the housing in response to the dispense signal;

reading the code of a dispensed package with a code reader;

verifying that the requested package was dispensed monitoring an amount of packages within the housing;

generating a reload signal;

opening the housing;

scanning packages with a bar code reader as the packages are loaded into the housing; and recording data in a memory regarding the loaded packages.

25. The method of claim 24 further comprising the step of printing a prescription label at a label printer for attaching to the dispensed package.

26. The method of claim 24 further comprising scanning the packages with a hand-held bar code reader during loading of the housing.

27. The method of claim 24 further comprising the step of delivering the dispensed pharmaceutical to a drop point with a ramp on the housing.

* * * * *